(12) United States Patent
Warne et al.

(10) Patent No.: US 7,635,473 B2
(45) Date of Patent: Dec. 22, 2009

(54) ANTI Aβ ANTIBODY FORMULATION

(75) Inventors: Nicholas W. Warne, Andover, MA (US); Donna Luisi, North Andover, MA (US); Angela Kantor, Pepperell, MA (US)

(73) Assignees: Janssen Alzheimer Immunotherapy, Little Island, County Cork (IE); Wyeth, Madison, NJ (US)

( * ) Notice: Subject to any disclaimer, the term of this patent is extended or adjusted under 35 U.S.C. 154(b) by 193 days.

(21) Appl. No.: 11/342,353

(22) Filed: Jan. 27, 2006

(65) Prior Publication Data

US 2006/0193850 A1    Aug. 31, 2006

Related U.S. Application Data

(60) Provisional application No. 60/648,631, filed on Jan. 28, 2005.

(51) Int. Cl.
  *A61K 39/395* (2006.01)
  *A61K 39/00* (2006.01)
(52) U.S. Cl. ................. 424/133.1; 424/152.1
(58) Field of Classification Search ........................ None
  See application file for complete search history.

(56) References Cited

U.S. PATENT DOCUMENTS

| | | | |
|---|---|---|---|
| 5,358,708 A | 10/1994 | Patel | |
| 5,385,887 A | 1/1995 | Yim et al. | |
| 5,688,651 A | 11/1997 | Solomon | |
| 5,744,132 A | 4/1998 | Warne et al. | |
| 5,770,700 A | 6/1998 | Webb et al. | |
| 5,786,180 A | 7/1998 | Konig et al. | |
| 6,267,958 B1 | 7/2001 | Andya et al. | |
| 6,270,757 B1 | 8/2001 | Warne | |
| 6,372,716 B1 | 4/2002 | Bush et al. | |
| 6,682,735 B2 | 1/2004 | Lowman et al. | |
| 6,710,226 B1 | 3/2004 | Schenk | |
| 6,743,427 B1 | 6/2004 | Schenk | |
| 6,750,324 B1* | 6/2004 | Schenk et al. | 530/387.1 |
| 6,761,888 B1 | 7/2004 | Schenk | |
| 6,787,138 B1 | 9/2004 | Schenk | |
| 6,787,139 B1 | 9/2004 | Schenk | |
| 6,787,140 B1 | 9/2004 | Schenk | |
| 6,787,143 B1 | 9/2004 | Schenk | |
| 6,787,144 B1 | 9/2004 | Schenk | |
| 6,787,523 B1 | 9/2004 | Schenk | |
| 6,787,637 B1 | 9/2004 | Schenk et al. | |
| 6,808,712 B2 | 10/2004 | Schenk | |
| 6,818,218 B2 | 11/2004 | Schenk | |
| 6,866,849 B2 | 3/2005 | Schenk | |
| 6,866,850 B2 | 3/2005 | Schenk | |
| 6,875,434 B1 | 4/2005 | Schenk | |
| 6,890,535 B1 | 5/2005 | Schenk | |
| 6,905,686 B1 | 6/2005 | Schenk | |
| 6,913,745 B1 | 7/2005 | Schenk | |
| 6,946,135 B2 | 9/2005 | Schenk | |
| 6,962,707 B2 | 11/2005 | Schenk | |
| 6,972,127 B2 | 12/2005 | Schenk | |
| 6,982,084 B2 | 1/2006 | Schenk | |
| 7,014,855 B2 | 3/2006 | Schenk | |
| 7,179,892 B2 | 2/2007 | Basi et al. | |
| 7,189,819 B2 | 3/2007 | Basi et al. | |
| 7,256,273 B2 | 8/2007 | Basi et al. | |
| 2003/0054484 A1* | 3/2003 | Fong et al. | 435/69.1 |
| 2003/0165496 A1 | 9/2003 | Basi et al. | |
| 2003/0171556 A1 | 9/2003 | Chae et al. | |
| 2003/0202972 A1 | 10/2003 | Andya et al. | |
| 2004/0081657 A1 | 4/2004 | Schenk | |
| 2004/0082762 A1 | 4/2004 | Basi et al. | |
| 2004/0087777 A1 | 5/2004 | Basi et al. | |
| 2004/0171815 A1 | 9/2004 | Schenk et al. | |
| 2004/0171816 A1 | 9/2004 | Schenk et al. | |
| 2004/0197324 A1 | 10/2004 | Liu et al. | |
| 2004/0213800 A1 | 10/2004 | Seubert et al. | |
| 2004/0219146 A1 | 11/2004 | Schenk | |
| 2004/0247590 A1 | 12/2004 | Schenk et al. | |
| 2004/0247591 A1 | 12/2004 | Schenk et al. | |
| 2004/0265301 A1 | 12/2004 | Schenk et al. | |

(Continued)

FOREIGN PATENT DOCUMENTS

| | | |
|---|---|---|
| EP | 0597101 | 5/1994 |
| EP | 0758248 B1 | 2/1997 |
| EP | 0758901 B1 | 2/1997 |
| EP | 1 033 998 B1 | 10/2005 |
| WO | WO 98/56418 A1 | 12/1998 |
| WO | WO 99/27944 A1 | 6/1999 |
| WO | WO 99/27949 A1 | 6/1999 |
| WO | WO 00/72876 A2 | 12/2000 |
| WO | WO 00/72876 A3 | 12/2000 |

(Continued)

OTHER PUBLICATIONS

U.S. Appl. No. 12/297,636, filed Jul. 2007, Lieberburg.*

(Continued)

*Primary Examiner*—Daniel E. Kolker
*Assistant Examiner*—Gregory S Emch
(74) *Attorney, Agent, or Firm*—Townsend and Townsend and Crew LLP

(57) ABSTRACT

The present invention provides formulations for maintaining the stability of Aβ binding polypeptides, for example, Aβ antibodies. Exemplary formulations include a tonicity agent such as mannitol and a buffering agent or amino acid such as histidine. Other exemplary formulations include an antioxidant in a sufficient amount as to inhibit by-product formation, for example, the formation of high molecular weight polypeptide aggregates, low molecular weight polypeptide degradation fragments, and mixtures thereof. The formulations of the invention optionally comprise a tonicity agent, such as mannitol, and a buffering agent or amino acid such as histidine. The formulations are suitable for several different routes of administration.

28 Claims, 11 Drawing Sheets

U.S. PATENT DOCUMENTS

| | | |
|---|---|---|
| 2004/0265308 A1 | 12/2004 | Schenk |
| 2005/0009150 A1 | 1/2005 | Basi et al. |
| 2005/0013815 A1 | 1/2005 | Schenk |
| 2005/0019328 A1 | 1/2005 | Schenk |
| 2005/0019330 A1 | 1/2005 | Schenk |
| 2005/0048049 A1 | 3/2005 | Schenk |
| 2005/0059591 A1 | 3/2005 | Schenk et al. |
| 2005/0059802 A1 | 3/2005 | Schenk et al. |
| 2005/0118651 A1 | 6/2005 | Basi et al. |
| 2005/0123544 A1 | 6/2005 | Schenk et al. |
| 2005/0142132 A1 | 6/2005 | Schenk et al. |
| 2005/0147613 A1 | 7/2005 | Raso |
| 2005/0158304 A1 | 7/2005 | Schenk et al. |
| 2005/0163788 A1 | 7/2005 | Schenk |
| 2005/0191292 A1 | 9/2005 | Schenk |
| 2005/0191314 A1 | 9/2005 | Schenk |
| 2005/0196399 A1 | 9/2005 | Schenk et al. |
| 2005/0249725 A1 | 11/2005 | Schenk et al. |
| 2005/0249727 A1 | 11/2005 | Schenk |
| 2005/0255122 A1 | 11/2005 | Schenk |
| 2006/0029611 A1 | 2/2006 | Schenk |
| 2006/0034858 A1 | 2/2006 | Schenk |
| 2006/0099206 A1 | 5/2006 | Sinacore |
| 2006/0153772 A1 | 7/2006 | Jacobsen |
| 2006/0160161 A1 | 7/2006 | Pavlikova et al. |
| 2006/0165682 A1 | 7/2006 | Basi et al. |
| 2006/0188512 A1 | 8/2006 | Yednock et al. |
| 2006/0193850 A1 | 8/2006 | Warne et al. |
| 2006/0198851 A1 | 9/2006 | Basi et al. |
| 2006/0210557 A1 | 9/2006 | Luisi et al. |
| 2006/0240486 A1 | 10/2006 | Johnson-Wood et al. |
| 2006/0257396 A1 | 11/2006 | Jacobsen |
| 2006/0280743 A1 | 12/2006 | Basi et al. |
| 2007/0082367 A1 | 4/2007 | Godavarti et al. |
| 2007/0134762 A1 | 6/2007 | Arumugham et al. |
| 2007/0154480 A1 | 7/2007 | Schenk et al. |
| 2007/0161088 A1 | 7/2007 | Arumugham et al. |
| 2007/0238154 A1 | 10/2007 | Basi et al. |
| 2008/0050367 A1 | 2/2008 | Basi et al. |
| 2008/0096818 A1 | 4/2008 | Schenk et al. |
| 2008/0145373 A1 | 6/2008 | Arumugham et al. |
| 2009/0155256 A1* | 6/2009 | Black et al. ............... 424/133.1 |

FOREIGN PATENT DOCUMENTS

| | | |
|---|---|---|
| WO | WO 00/72880 A2 | 12/2000 |
| WO | WO 00/72880 A3 | 12/2000 |
| WO | WO-01/05355 A2 | 1/2001 |
| WO | WO-01/62801 A2 | 8/2001 |
| WO | WO-02/46237 A2 | 6/2002 |
| WO | WO-02/088306 A2 | 11/2002 |
| WO | WO-02/088307 A2 | 11/2002 |
| WO | WO 02/096457 A2 | 12/2002 |
| WO | WO-03/009817 | 2/2003 |
| WO | WO-03/015691 A2 | 2/2003 |
| WO | WO-03/016466 | 2/2003 |
| WO | WO-03/039485 | 5/2003 |
| WO | WO-03/077858 A2 | 9/2003 |
| WO | WO-03/105894 | 12/2003 |
| WO | WO-2004/055164 | 7/2004 |
| WO | WO 2004/069182 A2 | 8/2004 |
| WO | WO 2004/080419 A2 | 9/2004 |
| WO | WO 2004/108895 A2 | 12/2004 |
| WO | WO 2005/058940 A2 | 6/2005 |
| WO | WO 2005/058941 A2 | 6/2005 |
| WO | WO 2006/081587 A2 | 8/2006 |
| WO | WO 2006/081587 A3 | 8/2006 |
| WO | WO 2006/083689 A2 | 8/2006 |

OTHER PUBLICATIONS

Bales, K.R. et al, "Administration of an Anti-Aβ Fab Fragment to APP$^{V717F}$ Transgenic Mice Reduces Neuritic Plaque," Abstract P4-396, p. S587, presented at Poster Session P4: Therapeutics and Therapeutic Strategies-Therapeutic Strategies, Amyloid-Based.

Bard, Frédérique et al, "Epitope and isotype specificities of antibodies to β-amyloid peptide for protection against Alzheimer's disease-like neuropathology," *PNAS*, vol. 100(4):2023-2028 (2003).

Bard, Frédérique et al, "Peripherally administered antibodies against amyloid β-peptide enter the central nervous system and reduce pathology in mouse model of Alzheimer disease," *Nature Medicine*, vol. 6(8):916-919 (2000).

Bussière, Thierry et al, "Morphological Characterization of Thioflavin-S-Positive Amyloid Plaques in Transgenic Alzheimer Mice and Effect of Passive Aβ Immunotherapy on Their Clearance," *American Journal of Pathology*, vol. 165(3):987-995 (2004).

Games, Dora et al, "Prevention and Reduction of AD-type Pathology in PDAPP Mice Immunized with Aβ$_{1-42}$," *Ann. NY Acad. Sci.*, vol. 920:274-284 (2000).

Kajkowski, Eileen M. et al, "β-Amyloid Peptide-induced Apoptosis Regulated by a Novel Protein Containing a G Protein Activation Module," *The Journal of Biological Chemistry*, vol. 276(22):18748-18756 (2001).

Zameer, Andleeb et al, "Single Chain Fv Antibodies against 25-35 Peptide Fragment of Amyloid-β: Potential Therapeutic for Alzheimer's Disease," *Abstract P4-420, p. S593, presented at Poster Session P4: Therapeutics and Therapeutic Strategies-Therapeutic Strategies, Amyloid-Based*.

Vidanovic, D. et al, "Effects of nonionic surfactants on the physical stability of immunoglobulin G in aqueous solution during mechanical agitation," *Die Pharmazie*, vol. 58(6):399-404 (2003).

Wang, W. et al, "Instability, stabilization, and formulation of liquid protein pharmaceuticals," *Int. J. Pharm.*, vol. 185(2):129-188 (1999).

International Search Report for Application No. PCT/US2006/002837, dated Aug. 11, 2006.

U.S. Appl. No. 12/106,206, filed Apr. 18, 2008, Schroeter.
U.S. Appl. No. 12/037,045, filed Feb. 25, 2008, Seubert.
U.S. Appl. No. 60/999,423, filed Oct. 17, 2007, Black.
U.S. Appl. No. 11/894,789, filed Aug. 20, 2007, Basi.
U.S. Appl. No. 11/894,754, filed Aug. 20, 2007.
U.S. Appl. No. 11/894,714, filed Aug. 20, 2007, Basi.
U.S. Appl. No. 11/894,665, filed Aug. 20, 2007, Schenk.
U.S. Appl. No. 11/893,123, filed Aug. 20, 2007.
U.S. Appl. No. 11/893,110, filed Aug. 20, 2007.
U.S. Appl. No. 11/893,103, filed Aug. 20, 2007.
U.S. Appl. No. 11/893,094, filed Aug. 20, 2007.
U.S. Appl. No. 11/842,120, filed Aug. 20, 2007, Schenk.
U.S. Appl. No. 11/842,116, filed Aug. 20, 2007, Schenk.
U.S. Appl. No. 11/842,113, filed Aug. 20, 2007, Schenk.
U.S. Appl. No. 11/842,101, filed Aug. 20, 2007, Schenk.
U.S. Appl. No. 11/842,056, filed Aug. 20, 2007, Basi.
U.S. Appl. No. 11/842,042, filed Aug. 20, 2007, Basi.
U.S. Appl. No. 11/842,023, filed Aug. 20, 2007, Basi.
U.S. Appl. No. 11/841,993, filed Aug. 20, 2007, Arumugham.
U.S. Appl. No. 11/841,950, filed Aug. 20, 2007, Arumugham.
U.S. Appl. No. 11/841,897, filed Aug. 20, 2007, Arumugham.
U.S. Appl. No. 11/841,882, filed Aug. 20, 2007, Arumugham.
U.S. Appl. No. 11/841,857, filed Aug. 20, 2007, Warne et al.
U.S. Appl. No. 11/841,849, filed Aug. 20, 2007, Arumugham.
U.S. Appl. No. 11/841,794, filed Aug. 20, 2007, Warne et al.
U.S. Appl. No. 11/841,832, filed Aug. 20, 2007, Warne et al.
U.S. Appl. No. 60/793,014, filed Apr. 18, 2006.
U.S. Appl. No. 11/396,417, filed Mar. 30, 2006, Schenk.
U.S. Appl. No. 11/396,391, filed Mar. 30, 2006, Schenk.
U.S. Appl. No. 11/358,951, filed Feb. 22, 2006, Solomon et al.
U.S. Appl. No. 11/342,252, filed Jan. 27, 2006, Luisi et al.
U.S. Appl. No. 60/736,119, filed Nov. 10, 2005, Jacobson.
U.S. Appl. No. 60/736,045, filed Nov. 10, 2005, Johnson-Wood.
U.S. Appl. No. 60/735,687, filed Nov. 10, 2005, Jacobson.
U.S. Appl. No. 11/245,524, filed Oct. 7, 2005, Schenk.

U.S. Appl. No. 11/245,916, filed Oct. 7, 2005, Schenk.
U.S. Appl. No. 60/691,821, filed Jun. 17, 2005, Godavarti.
U.S. Appl. No. 09/980,568, filed Mar. 12, 2005, Hirtzer.
U.S. Appl. No. 60/648,639, filed Jan. 28, 2005, Luisi et al.
U.S. Appl. No. 60/648,631, filed Jan. 28, 2005, Luisi et al.
U.S. Appl. No. 60/637,253, filed Dec. 16, 2004, Jacobson.
U.S. Appl. No. 60/637,138, filed Dec. 16, 2004, Jacobson.
U.S. Appl. No. 60/636,842, filed Dec. 15, 2004, Jacobson.
U.S. Appl. No. 60/636,810, filed Dec. 15, 2004, Jacobson.
U.S. Appl. No. 60/636,776, filed Dec. 15, 2004, Basi.
U.S. Appl. No. 60/636,687, filed Dec. 15, 2004, Johnson-Wood.
U.S. Appl. No. 60/636,684, filed Dec. 15, 2004, Basi.
U.S. Appl. No. 60/622,525, filed Oct. 26, 2004, Pavliakova.
U.S. Appl. No. 60/616,474, filed Oct. 5, 2004, Sinacore.
U.S. Appl. No. 60/530,481, filed Dec. 17, 2003, Arumugham.
U.S. Appl. No. 60/474,654, filed May 30, 2003, Basi.
U.S. Appl. No. 60/444,150, filed Feb. 1, 2003, Yednock.
U.S. Appl. No. 09/979,701, filed Mar. 13, 2002, Schenk.
U.S. Appl. No. 60/363,751, filed Mar. 12, 2002, Basi.
U.S. Appl. No. 60/251,892, filed Dec. 6, 2000, Basi et al.
U.S. Appl. No. 09/724,929, filed Nov. 28, 2000, Weiner.
U.S. Appl. No. 09/724,921, filed Nov. 28, 2000, Weiner.
U.S. Appl. No. 09/724,575, filed Nov. 28, 2000, Schenk.
U.S. Appl. No. 09/724,291, filed Nov. 28, 2000, Schenk.
U.S. Appl. No. 09/724,288, filed Nov. 28, 2000, Schenk.
U.S. Appl. No. 09/724,273, filed Nov. 28, 2000, Schenk.
U.S. Appl. No. 09/723,765, filed Nov. 28, 2000, Schenk.
U.S. Appl. No. 09/723,544, filed Nov. 28, 2000, Schenk.
U.S. Appl. No. 09/724,495, filed Nov. 27, 2000, Schenk.
U.S. Appl. No. 09/724,319, filed Nov. 27, 2000, Schenk.
U.S. Appl. No. 09/723,766, filed Nov. 27, 2000, Hirtzer.
U.S. Appl. No. 09/723,760, filed Nov. 27, 2000, Schenk.
U.S. Appl. No. 09/723,725, filed Nov. 27, 2000, Hirtzer.
U.S. Appl. No. 09/723,713, filed Nov. 27, 2000, Schenk.
U.S. Appl. No. 09/585,656.
U.S. Appl. No. 09/580,019, filed May 26, 2000, Schenk.
U.S. Appl. No. 09/580,015, filed May 26, 2000, Schenk.
U.S. Appl. No. 09/579,690, filed May 26, 2000, Brayden.
U.S. Appl. No. 09/497,553, filed Feb. 3, 2000, Schenk.
U.S. Appl. No. 60/139,408, filed Jun. 16, 1999, Raso.
U.S. Appl. No. 60/137,047, filed Jun. 1, 1999, Hirtzer.
U.S. Appl. No. 60/137,010, filed Jun. 1, 1999, Schenk.
U.S. Appl. No. 60/136,655, filed May 28, 1999, Brayden.
U.S. Appl. No. 09/322,289, filed May 28, 1999, Schenk.
U.S. Appl. No. 60/080,970, filed Jan. 11, 1999, Schenk.
U.S. Appl. No. 09/204,838, filed Dec. 3, 1998, Weiner.
U.S. Appl. No. 60/079,697, filed Mar. 27, 1998, Weiner et al.
U.S. Appl. No. 60/067,740, filed Dec. 2, 1997, Schenk.
U.S. Appl. No. 60/067,219, filed Dec. 3, 1997, Weiner et al.
U.S. Appl. No. 60/925,228.
Cleland et al., "A Specific Molar Ratio of Stabilizer to Protein is Required for Storage Stability of a Lyophilized Monoclonal Antibody," Journal of Pharmaceutical Sciences 90(30):310-321 (2001).
Daugherty et al., "Formulation and Delivery Issues For Monoclonal Antibody Therapeutics," Advanced Drug Delivery Reviews, 58: 5-6 (2006)/.
Lam et al., "Antioxidants for Prevention of Methioine Oxidation in Recombinant Monoclonal Antibody HER2," *J. Pharm. Sci.*, 86:1250-1255 (1997).
Mannitol MSDS, Material Safety Data Sheet, http://ScienceLab.com, p. 1-6, updated Nov. 6, 2008.
Patro et al., "Protein Formulation and Fill-Finish Operations," *Biotechnology Annual Review*, 8:55-84 (2002).
PCT International Preliminary Report on Patentability (Chapter II) of Dec. 21, 2006 for application PCT/US2006/002837.
PCT Written Opinion of Aug. 11, 2006 for application PCT/US2006/002837.
PCT International Preliminary Report on Patentability (Chapter I) of Jul. 31, 2007 with Written Opinion for application PCT/US2006/004741.
Wang et al., "Lyophilization and Development of Solid Protein Pharmaceuticals," *Int. J. Pharmaceutics*, 203:1-60 (2000).

\* cited by examiner

FIG. 2

Light Chain

```
  1  DVVMTQSPLS LPVTPGEPAS ISCKSSQSLL DSDGKTYLNW LLQKPGQSPQ
 51  RLIYLVSKLD SGVPDRFSGS GSGTDFTLKI SRVEAEDVGV YYCWQGTHFP
101  RTFGQGTKVE IKRTVAAPSV FIFPPSDEQL KSGTASVVCL LNNFYPREAK
151  VQWKVDNALQ SGNSQESVTE QDSKDSTYSL SSTLTLSKAD YEKHKVYACE
201  VTHQGLSSPV TKSFNRGEC
```
→ Heavy Chain

Heavy Chain

```
  1  EVQLLESGGG LVQPGGSLRL SCAASGFTFS NYGMSWVRQA PGKGLEWVAS
 51  IRSGGGRTYY SDNVKGRFTI SRDNSKNTLY LQMNSLRAED TAVYYCVRYD
101  HYSGSSDYWG QGTLVTVSSA STKGPSVFPL APSSKSTSGG TAALGCLVKD
151  YFPEPVTVSW NSGALTSGVH TFPAVLQSSG LYSLSSVVTV PSSSLGTQTY
201  ICNVNHKPSN TKVDKKVEPK SCDKTHTCPP CPAPELLGGP SVFLFPPKPK
251  DTLMISRTPE VTCVVVDVSH EDPEVKFNWY VDGVEVHNAK TKPREEQYNS
301  TYRVVSVLTV LHQDWLNGKE YKCKVSNKAL PAPIEKTISK AKGQPREPQV
351  YTLPPSREEM TKNQVSLTCL VKGFYPSDIA VEWESNGQPE NNYKTTPPVL
401  DSDGSFFLYS KLTVDKSRWQ QGNVFSCSVM HEALHNHYTQ KSLSLSPG(K)
```
→ Light Chain

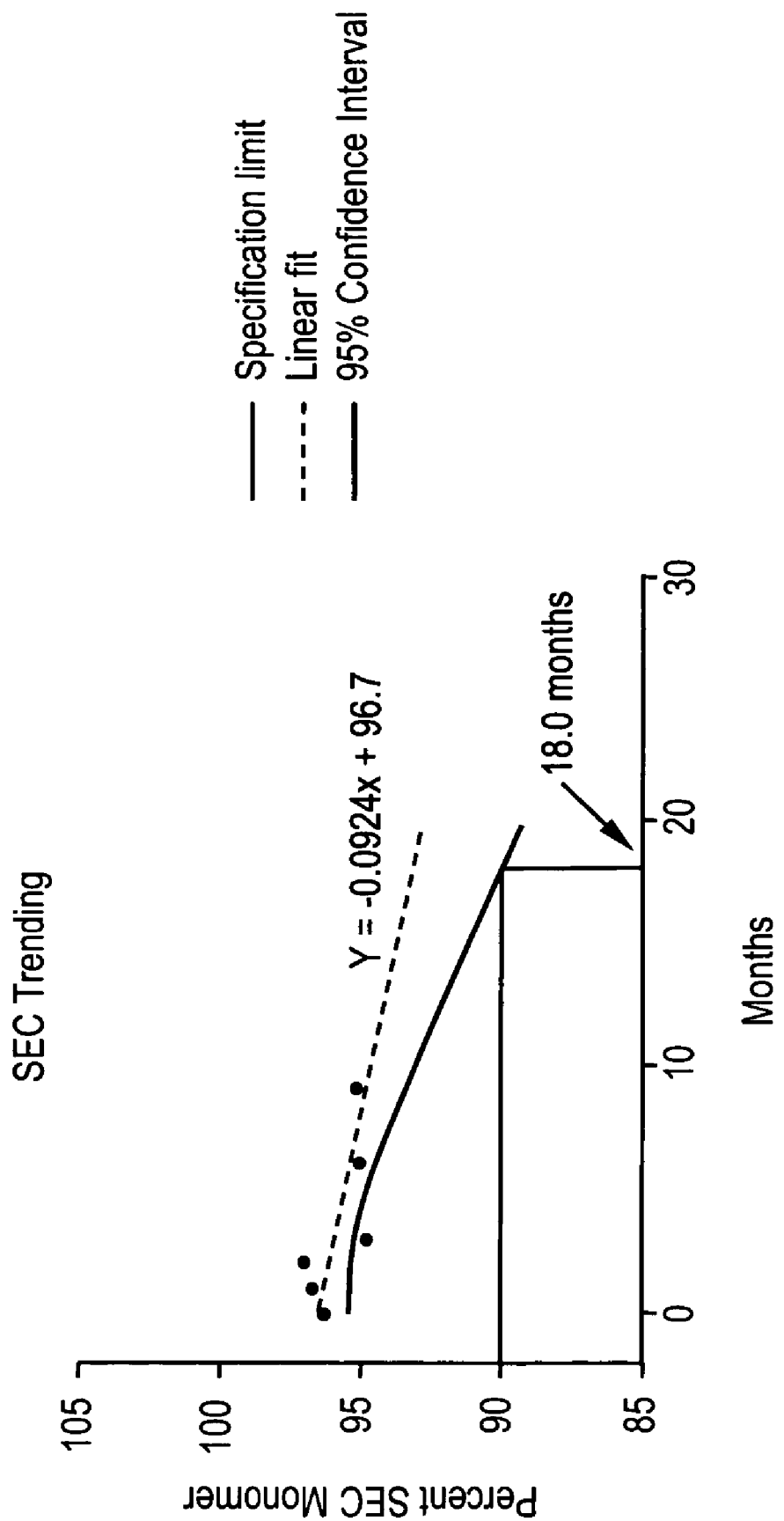

pH Study of IgG$_2$ Antibody 5°C 6 Weeks pH Study of IgG$_2$ Antibody 40°C 6 Weeks Buffer:      10 mM histidine, 150 mM NaCl
B+PS:        10 mM histidine, 150 mm NaCl, 0.01% PS80
B+Met:       10 mM histidine, 150 mm NaCl, 10 mM methionine
B+Met+PS:    10 mM histidine, 150 mm NaCl, 10 mM methionine, 0.01% PS80
Concentration 1 mg/mL

ANTI Aβ ANTIBODY FORMULATION

RELATED APPLICATIONS

This application claims the benefit of U.S. provisional patent application bearing Ser. No. 60/648,631 (filed Jan. 28, 2005), entitled "Anti A Beta Antibody Formulation". The entire content of the above-referenced application is incorporated herein by reference.

BACKGROUND OF THE INVENTION

Alzheimer's disease ("AD") is a neurodegenerative disorder characterized by the occurrence of amyloid plaques, neurofibrillary tangles and significant neuronal loss. β-Amyloid protein (also referred to as the Aβ peptide), the main component of senile plaques, has been implicated in the pathogenesis of Alzheimer's disease (Selkoe (1989) *Cell* 58:611-612; Hardy (1997) *Trends Neurosci.* 20:154-159). β-Amyloid has been shown to be both directly toxic to cultured neurons (Lorenzo and Yankner (1996) *Ann. NY Acad. Sci.* 777:89-95) and indirectly toxic through various mediators (Koh et al. (1990) *Brain Research* 533:315-320; Mattson et al. (1992) J. Neurosciences 12:376-389). Additionally, in vivo models, including the PDAPP mouse and a rat model have linked β-amyloid to learning deficits, altered cognitive function, and inhibition of long-term hippocampal potentiation (Chen et al. (2000) *Nature* 408:975-985; Walsh et al. (2002) *Nature* 416: 535-539). Therefore, a great deal of interest has focused on therapies that alter the levels of β-amyloid to potentially reduce the severity or even abrogate the disease itself.

One AD treatment strategy that has recently emerged in response to successful studies in PDAPP mouse and rat experimental models, is that of immunization of individuals to either provide immunoglobulins such as antibodies (as in the case of passive immunization, wherein therapeutic immunoglobulins are administered to a subject) or to generate immunoglobulins (active immunization, wherein the immune system of a subject is activated to produce immunoglobulins to an administered antigen) specific to β-amyloid. These antibodies would in turn help reduce the plaque burden by preventing β-amyloid aggregation (Solomon et al. (1997) *Neurobiology* 94:4109-4112) or stimulating microglial cells to phagocytose and remove plaques (Bard et al. (2000) *Nature Medicine* 6: 916-919). Further by way of example, a humanized anti Aβ peptide IgG1 monoclonal antibody (a humanized 3D6 antibody) can effectively treat AD by selectively binding human Aβ peptide.

For a protein, and in particular, an antibody, to remain biologically active, a formulation must preserve intact the conformational integrity of at least a core sequence of the protein's amino acids while at the same time protecting the protein's multiple functional groups from degradation. Degradation pathways for proteins can involve chemical instability (i.e., any process which involves modification of the protein by bond formation or cleavage resulting in a new chemical entity) or physical instability (i.e., changes in the higher order structure of the protein). Chemical instability can result from deamidation, racemization, hydrolysis, oxidation, beta elimination or disulfide exchange. Physical instability can result from denaturation, aggregation, precipitation or adsorption, for example. For a general review of stability of protein pharmaceuticals, see, for example, Manning, et al. (1989) *Pharmaceutical Research* 6:903-918. In addition, it is desirable to maintain stability when carrier polypeptides are not included in the formulation.

While the possible occurrence of protein instabilities is widely appreciated, it is impossible to predict particular instability issues for a particular protein. Any of these instabilities can potentially result in the formation of a polypeptide by-product or derivative having lowered activity, increased toxicity, and/or increased immunogenicity. Indeed, polypeptide precipitation can lead to thrombosis, non-homogeneity of dosage form and immune reactions. Thus, the safety and efficacy of any pharmaceutical formulation of a polypeptide is directly related to its stability.

Accordingly, there continues to exist a need for formulations that not only maintain the stability and biological activity of biological polypeptides, for example, Aβ binding polypeptides, upon storage and delivery, but are also suitable for various routes of therapeutic administration.

SUMMARY OF THE INVENTION

The present invention provides formulations designed to provide stability and to maintain the biological activity of an incorporated biologically active protein, in particular Aβ binding proteins or polypeptides, such as, for example, Aβ antibodies or fragments or portions thereof. The invention further provides polypeptide formulations, such as, for example, stabilized liquid polypeptide formulations that are resistant to the formation of undesired polypeptide by-products.

The integrity of antigen-binding polypeptides for therapeutic use is especially important because if the polypeptide forms by-products, for example, aggregates or degradation fragments during storage, bioactivity may be lost, thereby jeopardizing the therapeutic activity of the molecule per unit dose. In addition, there is an acute desire to stabilize therapeutic polypeptides intended for specialized functions, for delivery and use in certain biological indications, for example, treating neurodegenerative conditions, where a polypeptide must traverse the blood-brain-barrier (BBB) and bind a target antigen.

In one aspect, the present invention provides a stabilized formulation including at least one Aβ binding polypeptide, at least one tonicity agent, wherein the tonicity agent is present in an amount sufficient to render the formulation suitable for administration, and at least one buffering agent in an amount sufficient to maintain a physiologically suitable pH. The formulation can be a lyophilized or a liquid formulation. Some formulations include at least one antioxidant, such as, for example, an amino acid antioxidant, such as, for example, methionine. In some formulations, the tonicity agent is mannitol or NaCl. In some formulations, at least one buffering agent is succinate, sodium phosphate, or an amino acid such as histidine. Preferred formulations also include at least one stabilizer such as, for example, polysorbate 80. In some formulations, the stabilizer is polysorbate 80, the antioxidant is methionine, the tonicity agent is mannitol, sorbitol or NaCl, and the buffering agent is histidine. In some formulations, at least one Aβ binding polypeptide is selected from the group consisting of an anti Aβ antibody, an anti Aβ antibody Fv fragment, an anti Aβ antibody Fab fragment, an anti Aβ antibody Fab'(2) fragment, an anti Aβ antibody Fd fragment, a single-chain anti Aβ antibody (scFv), a single domain anti Aβ antibody fragment (Dab), a beta-pleated sheet polypeptide including at least one antibody complementarity determining region (CDR) from an anti Aβ antibody, and a non-globular polypeptide including at least one antibody CDR from an anti Aβ antibody. In some formulations, at least one Aβ binding polypeptide is an anti Aβ antibody, for example, that specifically binds to epitope within residues 1-7, 1-5, 3-7, 3-6, 13-28, 15-24, 16-24, 16-21, 19-22, 33-40, 33-42 of Aβ, or Fab, Fab'(2) or Fv fragment thereof. Exemplary anti Aβ antibodies specifically bind to an epitope within residues 1-10 of Aβ, such as, for example, within residues 1-7, 1-5, 3-7, or 3-6 of Aβ. Other exemplary anti Aβ antibodies specifically bind to an epitope within residues 13-28 of Aβ, such as, for example, within residues 16-21 or 19-22 of Aβ. Yet other exemplary anti Aβ antibodies specifically bind to a C terminal epitope of Aβ such as, for example, 33-40 or 33-42 of Aβ. Preferred anti Aβ antibodies include a humanized anti Aβ antibody, for example, a humanized 3D6 antibody, a humanized 10D5 antibody, a humanized 12B4 antibody, a humanized 266 antibody, a humanized 12A11 antibody, or a humanized 15C11 antibody.

In some formulations, the anti Aβ antibody binds a discontinuous epitope which includes residues within 1-7 and within 13-28 of Aβ. In some such formulations, the antibody is bispecific antibody or an antibody made by the process described in International Patent Publication No. WO03/070760. In some such formulations, the epitope is a discontinuous epitope. In preferred formulations, the anti Aβ antibody is a humanized 3D6 antibody, a humanized 10D5 antibody, a humanized 12B4 antibody, a humanized 266 antibody, a humanized 12A11 antibody, or a humanized 15C11 antibody.

The isotype of the antibody can be IgM, IgG1, IgG2, IgG3, IgG4 or any other pharmaceutically acceptable isotype. In preferred formulations, the isotype is human IgG1 or human IgG4. In some liquid formulations, the concentration of the anti Aβ antibody is about 0.1 mg/ml to about 60 mg/ml, about 40 mg/ml to about 60 mg/ml, about 50 mg/ml, about 30 mg/ml, about 17 mg/ml to about 23 mg/ml, about 20 mg/ml, about 17 mg/ml, about 10 mg/ml, about 5 mg/ml, about 2 mg/ml, or about 1 mg/ml, preferably about 17 mg/ml to about 23 mg/ml In some formulations, at least one tonicity agent is D-mannitol and is present at a concentration of about 1% w/v to about 10% w/v, about 2% w/v to about 6% w/v, or preferably about 4% w/v. In some formulations, at least one buffering agent is histidine and is present at a concentration of about 0.1 mM to about 25 mM, about 5 mM to about 15 mM, preferably about 5 mM or about 10 mM. In other formulations, at least one buffering agent is succinate and is present at a concentration of about 0.1 mM to about 25 mM, such as, for example, at about 10 mM. In some formulations, the antioxidant is methionine and is present at a concentration of about 0.1 mM to about 25 mM, about 5 mM to about 15 mM, or preferably about 10 mM. In preferred formulations, the stabilizer is polysorbate 80 and is present at a concentration of about 0.001% w/v to about 0.01% w/v, about 0.005% w/v to about 0.01% w/v, or about 0.005% w/v. The formulation can have a pH of about 5 to 7, about 5.5 to about 6.5, about 6.0 to about 6.5, about 6.2, about 6.0, or about 5.5, preferably about 6.0.

A preferred formulation has a pH of about 6.0 to about 6.5 and includes an anti Aβ antibody that specifically binds to an epitope within residues selected from the group consisting of 1-7, 1-5, 3-7, 3-6, 13-28, 15-24, 16-24, 16-21, 19-22, 33-40 and 33-42 of Aβ, for example D-mannitol at a concentration of about 2% w/v to about 6%, for example histidine at a concentration of about 0.1 mM to about 25 mM, methionine at a concentration of about 0.1 mM to about 25 mM, and a stabilizer. Preferably, the stabilizer is polysorbate 80 at a concentration of about 0.001% to about 0.01% w/v.

The formulation can be a stabilized liquid polypeptide formulation designed to provide stability and to maintain the biological activity of the incorporated polypeptide. The formulation includes a therapeutically active Aβ-binding polypeptide and an antioxidant in an amount sufficient to reduce the by-product formation of the polypeptide during storage of the formulation.

Some of the liquid polypeptide formulations are stabilized against the formation of undesired by-products such as high molecular weight polypeptide aggregates, low molecular weight polypeptide degradation products, or mixtures thereof.

In formulations wherein the therapeutic antigen-binding polypeptide is an antibody, the typical high molecular weight aggregates to be minimized are, for example, antibody:antibody complexes, antibody:antibody fragment complexes, antibody fragment:antibody fragment complexes, or mixtures thereof. In general, high molecular weight complexes or by-products have a molecular weight greater than a monomer of the antigen-binding polypeptide, for example, in the case of an IgG antibody, greater than about 150 kD. In such antibody formulations, the typical low molecular weight polypeptide degradation products to be minimized are, for example, complexes consisting of an antibody light chain, an antibody heavy chain, an antibody light chain and heavy chain complex, or mixtures thereof. In general, low molecular weight complexes or by-products have a molecular weight less than that of a monomer of the antigen-binding polypeptide, for example, in the case of an IgG antibody, less than about 150 kD.

A preferred stabilized formulation of an anti-Aβ antibody includes methionine as an antioxidant in an amount sufficient to inhibit the formation of undesired by-products, a tonicity agent for example in an amount sufficient to render the formulation suitable for administration, and an amino acid for example or derivative thereof in an amount sufficient to maintain a physiologically suitable pH.

Some formulations are stable when frozen. The formulation can be suitable for administering parenterally, intravenously, intramuscularly, subcutaneously, intracranially, or epidurally, preferably intravenously or subcutaneously. Some formulations can be suitable for targeted delivery to the brain or the spinal fluid of a subject. The formulation can be substantially free of preservatives. Some formulations are stable for at least about 12 months, at least about 18 months, at least about 24 months, or at least about 30 months. Some formulations are stable at about −80° C. to about 40° C., at about 0° C. to about 25° C., at about 0° C. to about 11° C., preferably at about −80° C. to about −50° C. or at about 2° C. to about 8° C.

Some formulations are stable for at least about 12 months at a temperature of above freezing to about 10° C. and has a pH of about 5.5 to about 6.5. Such formulation includes at least one Aβ antibody at a concentration of about 1 mg/ml to about 30 mg/ml, mannitol at a concentration of about 4% w/v or NaCl at a concentration of about 150 mM, histidine or succinate at a concentration of about 5 mM to about 10 mM, and 10 mM methionine. One such formulation has a pH of about 6.0, about 1 mg/ml Aβ antibody, about 10 mM histidine and about 4% w/v mannitol. Other formulations are stable for at least about 24 months at a temperature of about 2° C. to 8° C., and include polysorbate 80 at a concentration of about 0.001% w/v to about 0.01% w/v. Some of such formulations have a pH of about 6.0 to about 6.5 and include about 10 mM histidine, about 4% w/v mannitol and about 1 mg/ml, about 2 mg/ml or about 5 mg/ml Aβ antibody. Other such formulations include about 10 mM histidine, about 4% w/v mannitol, about 0.005% w/v polysorbate 80 and about 10 mg/ml, about 20 mg/ml or 30 mg/ml Aβ antibody, preferably at a pH of about 6.0 to about 6.2.

The anti Aβ antibody in such formulations is preferably a humanized 3D6 antibody, a humanized 10D5 antibody, a humanized 12B4 antibody, a humanized 266 antibody, a humanized 12A11 antibody, or a humanized 15C11 antibody. One such formulation has a pH of about 6.0 to 6.5 and includes about 10 mM histidine, about 4% w/v mannitol and about 2 mg/ml to about 20 mg/ml of an Aβ antibody selected from the group consisting of a humanized 3D6 antibody, a humanized 10D5 antibody, a humanized 12B4 antibody, and a humanized 12A11 antibody. Another such formulation has a pH of about 6.0 to 6.5 and includes about 10 mM histidine, about 150 mM NaCl and about 2 mg/ml to about 20 mg/ml of an Aβ antibody selected from the group consisting of a humanized 12B4 antibody and a humanized 12A11 antibody. Yet another such formulation has a pH of about 6.0 to 6.5 and includes about 10 mM histidine, about 4% w/v mannitol and about 2 mg/ml to about 20 mg/ml of an Aβ antibody selected from the group consisting of a humanized 266 antibody and a humanized 15C11 antibody.

A preferred formulation is stable for at least about 24 months at a temperature of about 2° C. to about 8° C., has a pH of about 5.5 to about 6.5, and includes about 2 mg/ml to about 23 mg/ml, preferably about 17 mg/ml to about 23 mg/ml, of a humanized 3D6 antibody, about 10 mM histidine and about 10 mM methionine. Preferably, the formulation further includes about 4% w/v mannitol. The formulation preferably includes polysorbate 80 at a concentration of about 0.001% w/v to about 0.01% w/v, more preferably about 0.005% w/v polysorbate 80. In such formulations, the humanized 3D6 antibody can be present at a concentration of about 20 mg/ml to about 23 mg/ml.

Another formulation is stable for at least about 24 months at a temperature of about 2° C. to about 8° C., has a pH of about 5.5 to about 6.5, and includes about 2 mg/ml to about 23 mg/ml of a humanized 3D6 antibody, about 10 mM succinate, about 10 mM methionine, about 4% w/v mannitol and about 0.005% w/v polysorbate 80. In some of such formulations, the humanized 3D6 antibody concentration is present at a concentration of about 17 mg/ml to about 23 mg/ml.

Another preferred formulation is stable for at least about 24 months at a temperature of about 2° C. to about 8° C., has a pH of about 6.0 to about 6.5, and includes about 2 mg/ml to about 30 mg/ml of a humanized 266 antibody, about 10 mM histidine and about 10 mM methionine. Some of such formulations further include about 4% w/v mannitol. Some of such formulations include polysorbate 80 at a concentration of about 0.001% w/v to about 0.01% w/v, for example, about 0.005% w/v polysorbate 80. In some of such formulations, the humanized 266 antibody is present at a concentration of about 17 mg/ml to about 23 mg/ml or about 20 mg/ml to about 23 mg/ml.

Yet another formulation is stable for at least about 24 months at a temperature of about 2° C. to about 8° C., has a pH of about 6.0 to about 6.5, and includes about 2 mg/ml to about 20 mg/ml of a humanized 266 antibody, about 10 mM succinate, about 10 mM methionine, about 4% w/v mannitol and about 0.005% w/v polysorbate.

Another preferred formulation is stable for at least about 24 months at a temperature of about 2° C. to about 8° C., has a pH of about 6.0 to about 6.5, and includes about 2 mg/ml to about 30 mg/ml of a humanized 12A11 antibody, about 10 mM histidine and about 10 mM methionine. Some of such formulations include about 150 mM NaCl. Such formulations can include polysorbate 80 at a concentration of about 0.001% w/v to about 0.01% w/v, such as, for example, about 0.005% w/v polysorbate 80. In some of the formulations, the human-ized 12A11 antibody is present at a concentration of about 17 mg/ml to about 23 mg/ml or about 20 mg/ml to about 23 mg/ml.

Yet another formulation is stable for at least about 24 months at a temperature of about 2° C. to about 8° C., has a pH of about 6.0 to about 6.5, and includes about 2 mg/ml to about 20 mg/ml of a humanized 12A11 antibody, about 5 mM histidine, about 10 mM methionine, about 4% w/v mannitol and about 0.005% w/v polysorbate 80.

The invention also provides a formulation that is stable when thawed from about −50° C. to about −80° C., has a pH of about 6.0 and includes about 40 to about 60 mg/ml of an anti Aβ antibody, about 1.0 mg/ml to about 2.0 mg/ml histidine, about 1.0 mg/ml to 2.0 mg/ml methionine and about 0.05 mg/ml polysorbate 80. Preferably, mannitol is excluded. Preferably, the Aβ antibody is a humanized 3D6 antibody or a humanized 266 antibody.

The present invention also provides a liquid formulation including an anti Aβ antibody, mannitol and histidine. In some of such formulations, the anti Aβ antibody is present from about 1 mg/ml to about 30 mg/ml. Preferably, the mannitol is present in an amount sufficient to maintain isotonicity of the formulation. Preferably, the histidine is present in an amount sufficient to maintain a physiologically suitable pH. One such formulation includes about 20 mg/mL anti Aβ antibody, about 10 mM L-histidine, about 10 mM methionine, about 4% mannitol and has a pH of about 6. Another such formulation includes about 30 mg/mL anti Aβ antibody, about 10 mM succinate, about 10 mM methionine, about 6% mannitol and has a pH of about 6.2. Yet another such formulation includes about 20 mg/mL anti Aβ antibody, about 10 mM L-histidine, about 10 mM methionine, about 4% mannitol, about 0.005% polysorbate 80, and has a pH of about 6. Another such formulation includes about 10 mg/mL anti Aβ antibody, about 10 mM succinate, about 10 mM methionine, about 10% mannitol, about 0.005% polysorbate 80, and has a pH of about 6.5.

Still another such formulation includes about 5 mg/mL to about 20 mg/mL anti Aβ antibody, about 5 mM to about 10 mM L-histidine, about 10 mM methionine, about 4% mannitol, about 0.005% polysorbate 80, and has a pH of about 6.0 to about 6.5. Yet another such formulation includes about 5 mg/mL to about 20 mg/mL anti Aβ antibody, about 5 mM to about 10 mM L-histidine, about 10 mM methionine, about 150 mM NaCl, about 0.005% polysorbate 80, and has a pH of about 6.0 to about 6.5.

The present invention also provides a formulation suitable for intravenous administration that includes about 20 mg/mL of an anti Aβ antibody, about 10 mM L-histidine, about 10 mM methionine, about 4% mannitol and has a pH of about 6. Preferably, such formulation includes about 0.005% polysorbate 80.

The invention provides a method for increasing the stability of an antigen-binding polypeptide, for example, an antibody, in a liquid pharmaceutical formulation, where the polypeptide would otherwise exhibit by-product formation during storage in a liquid formulation. Accordingly, the method comprises incorporating into the formulation an antioxidant, for example, methionine or an analog thereof, in an amount sufficient to reduce the amount of by-product formation.

The present invention also provides a method for maintaining the stability of a humanized anti Aβ antibody formulation to be stored at a temperature of about −50° C. to about −80° C. followed by storage at a temperature of about 2° C. to about 8° C., comprising (i) combining about 40 mg/ml to about 60 mg/ml humanized anti Aβ antibody, about 1 mg/ml to about 2 mg/ml L-histidine, about 1 mg/ml to about 2 mg/ml methionine and about 0.05 mg/ml polysorbate 80; (ii) adjusting the pH to about 6.0; (iii) filtering into a cryovessel and freezing; (iv) thawing; (v) adding mannitol or NaCl and diluent in amounts sufficient to result in a final concentration of about 4% mannitol or about 150 mM NaCl, about 2 mg/ml to about 20 mg/ml humanized anti Aβ antibody; about 5 mM to about 10 mM histidine; about 10 mM methionine and about 0.005% polysorbate 80; (vi) filtering; (vii) transferring to a glass vial and sealing; and (viii) storing at a temperature of about 2° C. to about 8° C.

The present invention also provides a kit including a container with a formulation described herein and instructions for use.

The present invention also provides a pharmaceutical unit dosage form, including a formulation of about 10 mg to about 250 mg of an anti Aβ antibody, about 4% mannitol or about 150 mM NaCl, about 5 mM to about 10 mM histidine or succinate, and about 10 mM methionine. Some of such pharmaceutical unit dosage forms include about 0.001% to about 0.1% of polysorbate 80. Some of such pharmaceutical unit dosage forms include about 40 mg to about 60 mg, about 60 mg to about 80 mg, about 80 mg to about 120 mg, about 120 mg to about 160 mg, or about 160 mg to about 240 mg of the anti Aβ antibody. Some of such formulations can be maintained in a glass vial at a temperature of about 2° C. to about 8° C. prior to administration to a patient.

In addition, the present invention provides a therapeutic product including a glass vial with a formulation including about 10 mg to about 250 mg of a humanized anti Aβ antibody, about 4% mannitol or about 150 mM NaCl, about 5 mM to about 10 mM histidine, and about 10 mM methionine. Some of suchhe therapeutic products further include a labeling for use including instructions to use the appropriate volume necessary to achieve a dose of about 0.15 mg/kg to about 5 mg/kg in a patient. Typically, the vial is a 1 mL, a 2 mL, a 5 mL, a 10 mL, a 25 mL or a 50 mL vial. The dose of some of such therapeutic products is about 0.5 mg/kg to about 3 mg/kg, preferably about 1 mg/kg to about 2 mg/kg. In some such therapeutic products, the anti Aβ antibody concentration is about 10 mg/ml to about 60 mg/ml, preferably about 20 mg/ml. The therapeutic product preferably includes about 0.005% polysorbate 80. The formulation of some such therapeutic products is for subcutaneous administration or intravenous administration.

The present invention also provides a method for prophylactically or therapeutically treating a disease characterized by Aβ deposits that includes intravenously or subcutaneously administering a pharmaceutical unit dosage as described herein.

Other features and advantages of the invention will be apparent from the following detailed description and claims.

BRIEF DESCRIPTION OF THE DRAWINGS

FIG. 2 shows the complete amino acid sequences of the humanized 3D6 version 2 (hu3D6.v2) anti Aβ antibody light and heavy chains, SEQ ID NO1 and SEQ ID NO:2, respectively. Light chain complementarity determining regions (CDR), i.e., CDR1, CDR2, and CDR3 are, respectively, at residue positions 24-39, 55-61, and 94-102 (upper panel). Heavy chain complementarity determining regions (CDR), i.e., CDR1, CDR2, and CDR3 are, respectively, at residue positions 40-44, 50-65, and 99-108 (lower panel). Predicted intramolecular disulfide bonds are illustrated by connections of the cysteine residues involved. Cysteines expected to form intermolecular disulfide bonds are underlined and the connectivity indicated. The N-linked glycosylation consensus site of the antibody heavy chain is indicated in italics at residue positions 299-301 (lower panel). The predicted heavy chain C-terminal lysine is shown in parenthesis.

FIG. 8 graphically depicts the degradation predictions of formulations without PS80 made in accordance with the present invention and stored at 5° C.

DETAILED DESCRIPTION OF THE INVENTION

Figure 1:
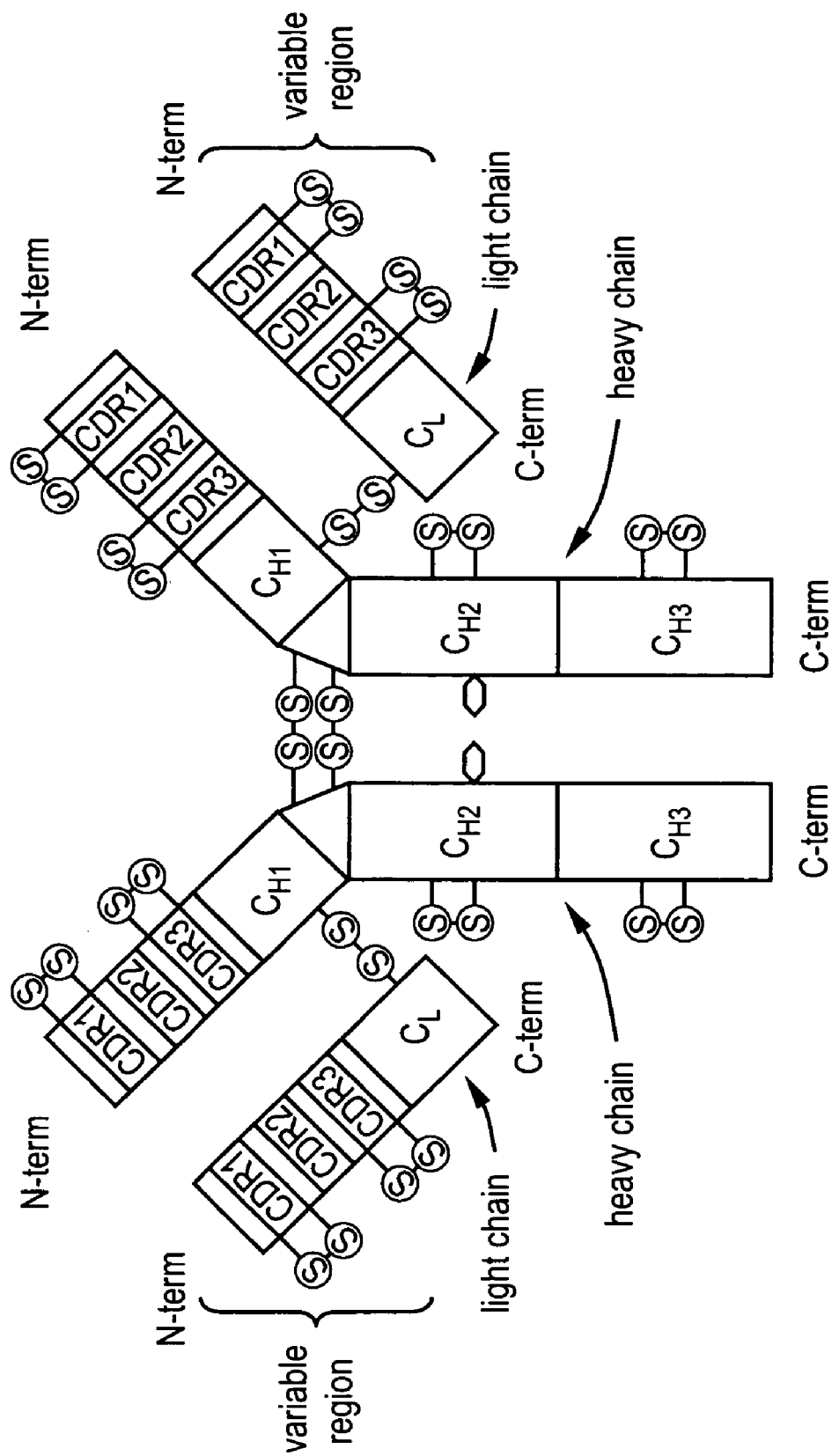
FIG. 1 depicts a schematic representation of the predicted structure of an IgG antibody and approximate positions of intra- and inter-chain disulfide bonds, glycosylation sites (hexagonal symbol), complementarity determining regions (CDRs), framework regions (shaded), and constant regions.

In order to provide a clear understanding of the specification and claims, the following definitions are conveniently provided below.

As used herein, the term "amyloidogenic disease" includes any disease associated with (or caused by) the formation or deposition of insoluble amyloid fibrils. Exemplary amyloidogenic diseases include, but are not limited to systemic amyloidosis, Alzheimer's disease, mature onset diabetes, Parkinson's disease, Huntington's disease, fronto-temporal dementia, and the prion-related transmissible spongiform encephalopathies (kuru and Creutzfeldt-Jacob disease in humans and scrapie and BSE in sheep and cattle, respectively). Different amyloidogenic diseases are defined or characterized by the nature of the polypeptide component of the fibrils deposited. For example, in subjects or patients having Alzheimer's disease, β-amyloid protein (for example, wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ", for example, in the brain of a subject or patient.

The terms "β-amyloid protein", "β-amyloid peptide", "β-amyloid", "Aβ" and "Aβ peptide" are used interchangeably herein.

The term "Aβ binding polypeptide" includes polypeptides capable of specifically binding to Aβ peptide(s) or to epitope(s) within said Aβ peptides. Typically, Aβ binding polypeptides comprise at least a functional portion of an immunoglobulin or immunoglobulin-like domain, for example, a receptor that comprises one or more variability regions or complementarity determining regions (CDRs) which impart a specific binding characteristic to the polypeptide. Preferred antigen-binding polypeptides include antibodies, for example, IgM, IgG1, IgG2, IgG3, or IgG4.

The term "antibody" refers to immunoglobulin molecules and immunologically active portions of immunoglobulin molecules (molecules that contain an antigen binding site which specifically binds an antigen), including monoclonal antibodies (including full length monoclonal antibodies), polyclonal antibodies, multispecific antibodies (for example, bispecific antibodies), chimeric antibodies, CDR-grafted antibodies, humanized antibodies, human antibodies, and single chain antibodies (scFvs). The term "monoclonal antibody" or "monoclonal antibody composition", as used herein, refers to a population of antibody molecules that contain only one species of an antigen binding site capable of recognizing and binding to a particular epitope of a target antigen, for example, an epitope(s) of Aβ. A monoclonal antibody composition thus typically displays a single binding specificity and affinity for a particular target antigen with which it immunoreacts. The term "single-chain antibody" refers to a protein having a two-polypeptide chain structure consisting of a heavy and a light chain, said chains being stabilized, for example, by interchain peptide linkers, which has the ability to specifically bind antigen. Techniques for producing single chain antibodies specific to target antigen are described, for example, in U.S. Pat. No. 4,946,778. The term "antibody fragment" includes F(ab')2 fragments, Fab fragments, Fab' fragments, Fd fragments, Fv fragments, and single domain antibody fragments (DAbs). Immunologically active portions of immunoglobulins include, for example, F(ab) and F(ab')2 fragments. Methods for the construction of Fab fragments are described, for example, Huse, et al. (1989) Science 246:1275 1281). Other antibody fragments may be produced by techniques known in the art including, but not limited to: (i) an F(ab')2 fragment produced by pepsin digestion of an antibody molecule; (ii) a Fab fragment generated by reducing the disulfide bridges of an F(ab')2 fragment; (iii) a Fab' fragment generated by the treatment of the antibody molecule with papain and a reducing agent and (iv) Fv fragments. Various fragments can also be produced by art-recognized recombinant engineering techniques. Non-human antibodies can be "humanized" by techniques described, for example, in U.S. Pat. No. 5,225,539. In one method, the non-human CDRs are inserted into a human antibody or consensus antibody framework sequence. Further changes can then be introduced into the antibody framework to modulate affinity or immunogenicity The term "domain" refers to a globular region of a heavy or light chain polypeptide comprising an immunoglobulin fold. The immunoglobulin fold is comprised of β-pleated sheet secondary structure and includes a single disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (for example, a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "anti Aβ antibody" includes antibodies (and fragments thereof) that are capable of binding epitopes(s) of the Aβ peptide. Anti Aβ antibodies include, for example, those antibodies described in U.S. Patent Publication No. 20030165496A1, U.S. Patent Publication No. 20040087777A1, International Patent Publication No. WO02/46237A3, and International Patent Publication No. WO04/080419A2. Other anti Aβ antibodies are described in, for example, International Patent Publication Nos. WO03/077858A2 and WO04/108895A2, both entitled "Humanized Antibodies that Recognize Beta Amyloid Peptide", International Patent Publication No. WO03/016466A2, entitled "Anti-Aβ Antibodies", International Patent Publication No. WO0162801A2, entitled "Humanized Antibodies that Sequester Amyloid Beta Peptide", and International Patent Publication No. WO02/088306A2, entitled "Humanized Antibodies" and International Patent Publication No. WO03/070760A2, entitled "Anti-Aβ Antibodies and Their Use."

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments. The term "antigen-binding fragment" refers to a polypeptide fragment of an immunoglobulin or antibody that binds antigen or competes with the intact antibody from which they were derived for specific antigen binding.

The term "conformation" refers to the tertiary structure of a protein or polypeptide, such as, for example, an antibody, antibody chain, domain or region thereof. For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "specific binding" of an antibody means that the antibody exhibits appreciable affinity for a particular antigen or epitope and, generally, does not exhibit significant cross-reactivity. In exemplary embodiments, the antibody exhibits no cross-reactivity (for example, does not cross-react with non-Aβ peptides or with remote or distant epitopes on Aβ). "Appreciable" or preferred binding includes binding with an affinity of at least $10^{-6}$, $10^{-7}$, $10^{-8}$, $10^{-9}$ M, or $10^{-10}$ M. Affinities greater than $10^{-7}$ M, preferably greater than $10^{-8}$ M are more preferred. Values intermediate of those set forth herein are also intended to be within the scope of the present invention and a preferred binding affinity can be indicated as a range of affinities, for example, $10^{-6}$ to $10^{-10}$ M, preferably $10^{-7}$ to $10^{-10}$ M, more preferably $10^{-8}$ to $10^{-10}$ M. An antibody that "does not exhibit significant cross-reactivity" is one that will not appreciably bind to an undesirable entity (for example, an undesirable protein, polypeptide, or peptide). For example, an antibody that specifically binds to Aβ will appreciably bind Aβ but will not significantly react with non-Aβ proteins or peptides (for example, non-Aβ proteins or peptides included in plaques). An antibody specific for a particular epitope will, for example, not significantly cross-react with remote or different epitopes on the same protein or peptide. Specific binding can be determined according to any art-recognized means for determining such binding. Preferably, specific binding is determined according to Scatchard analysis and/or competitive binding assays.

Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, for example, Songsivilai & Lachmann, *Clin. Exp. Immunol.* 79:315-321 (1990); Kostelny et al., *J. Immunol.* 148, 1547-1553 (1992).

An "antigen" is a molecule (for example, a protein, polypeptide, peptide, carbohydrate, or small molecule) containing an antigenic determinant to which an antibody specifically binds.

The term "epitope" or "antigenic determinant" refers to a site on an antigen to which an immunoglobulin or antibody (or antigen binding fragment thereof) specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, x-ray crystallography and 2-dimensional nuclear magnetic resonance. See, for example, *Epitope Mapping Protocols in Methods in Molecular Biology*, Vol. 66, G. E. Morris, Ed. (1996).

The term "stabilized formulation" or "stabilized liquid polypeptide formulation" includes formulations in which the polypeptide therein essentially retains its physical and chemical identity and integrity upon storage. Various analytical techniques for measuring protein stability are available in the art and are described herein (reviewed in, Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993)). Stability can be measured at a selected temperature for a selected time period. For rapid testing, the formulation may be kept at a higher or "accelerated" temperature, for example, 40° C. for 2 weeks to 1 month or more at which time stability is measured. In exemplary embodiments, the formulation is refractory to the formation of by-products of the component polypeptide, for example, high molecular weight aggregation products, low molecular weight degradation or fragmentation products, or mixtures thereof. The term "stability" refers to the length of time over which a molecular species such as an antibody retains its original chemical identity, for example, primary, secondary, and/or tertiary structure.

The term "by-product" includes undesired products, which detract, or diminish the proportion of therapeutic polypeptide in a given formulation. Typical by-products include aggregates of the therapeutic polypeptide, fragments of the therapeutic polypeptide (for example, produced by degradation of the polypeptide by deamidation or hydrolysis), or mixtures thereof.

The term "high molecular weight polypeptide aggregates" includes aggregates of the therapeutic polypeptide, fragments of the therapeutic polypeptide (for example, produced by degradation of the polypeptide by, for example, hydrolysis), or mixtures thereof, that then aggregate. Typically, high molecular weight aggregates are complexes which have a molecular weight which is greater than the therapeutic monomer polypeptide. In the case of an antibody, for example, an IgG antibody, such aggregates are greater than about 150 kD. However, in the case of other therapeutic polypeptides, for example, single-chain antibodies, which typically have a molecular weight of 25 kD, such aggregates would have a molecular weight greater than about 25 kD.

The term "low molecular weight polypeptide degradation product" includes, for example, fragments of the therapeutic polypeptide, for example, brought about by deamidation or hydrolysis. Typically, low molecular weight degradation products are complexes which have a molecular weight which is less than the therapeutic monomer polypeptide. In the case of an antibody, for example, an IgG antibody, such degradation products are less than about 150 kD. However, in the case of other therapeutic polypeptides, for example, single-chain antibodies, which typically have a molecular weight of 25 kD, such aggregates would have a molecular weight less than about 25 kD.

The term "administration route" includes art recognized administration routes for delivering a therapeutic polypeptide such as, for example, parenterally, intravenously, intramuscularly, subcutaneously, intracranially, or epidurally. For the administration of a therapeutic polypeptide for the treatment of a neurodegenerative disease, intravenous, epidural, or intracranial routes, may be desired.

The term "treatment" as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, delay, relieve, alter, remedy, ameliorate, improve or affect the disease, the symptoms of disease or the predisposition toward disease.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the patient's own immune system.

The term "patient" includes human and other mammalian subjects that receive either prophylactic or therapeutic treatment.

The term "dosage unit form" (or "unit dosage form") as used herein refers to a physically discrete unit suitable as unitary dosages for the patient to be treated, each unit containing a predetermined quantity of active compound calculated to produce the desired thereapeutic effect in association with the required pharmaceutical carrier, diluent, or excipient. The specification for the dosage unit forms of the invention are dictated by and directly dependent on the unique characteristics of the active compound and the particular therapeutic effect to be achieved, and the limitations inherent in the art of compounding such an active compound for the treatment of patients.

Actual dosage levels of the active ingredient (for example Aβ polypeptides) in the formulations of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The term "diluent" as used herein refers to a solution suitable for altering or achieving an exemplary or appropriate concentration or concentrations as described herein.

Overview

The present invention provides formulations for Aβ binding polypeptides, in particular, anti Aβ antibodies, as well as portions and/or fragments thereof. In certain aspects, the invention provides stabilized liquid polypeptide formulations for therapeutic use. In particular, the invention provides for the stabilization of Aβ binding polypeptides, for example, antibodies, and antigen-binding fragments thereof, for the use in treating amyloidogenic diseases and/or disorders. In particular, the invention provides formulations that are stabilized such that the active therapeutic polypeptide is stable over an extended period of time and can be administered through a variety of administration routes. This is especially critical for those Aβ binding polypeptides (for example, antibodies) destined for use in the treatment of amyloidogenic diseases and/or disorders. In other aspects, the invention provides a uniquely stable antibody formulation that, for example, is stable to various stresses such as freezing, lyophilization, heat and/or reconstitution. Moreover, exemplary formulations of the present invention are capable of maintaining the stability, biological activity, purity and quality of the antibody over an extended period of time (for example, a year or more during which time the formulation is stored) and even at unfavorable temperatures. In addition, exemplary formulations of the present invention are suitable for administration to a subject or patient (for example, intravenous administration to a subject or patient), for example, a human having or predicted to have an amyloidogenic disease or disorder.

Formulations

In one aspect, the present invention provides a stabilized formulation including an Aβ binding polypeptide, a tonicity agent, where the tonicity agent is present in an amount sufficient to render the stabilized formulation suitable for intravenous infusion, and an amino acid or derivative thereof, where the amino acid or derivative thereof is present in an amount sufficient to maintain a physiologically suitable pH. In an exemplary embodiment, the present invention provides a stabilized formulation including an anti Aβ antibody, mannitol and histidine.

In one embodiment, the present invention provides a stabilized formulation including an Aβ binding polypeptide, a tonicity agent, wherein the tonicity agent is present in an amount sufficient to render the formulation suitable for intravenous infusion, and an amino acid or derivative thereof, where the amino acid or derivative thereof is present in an amount sufficient to maintain a physiologically suitable pH. In an exemplary embodiment, the tonicity agent is mannitol. In another exemplary embodiment, the amino acid is histidine.

In another aspect, the present invention provides a stabilized formulation including an Aβ binding polypeptide. Aβ binding polypeptides suitable for stabilization in a formulation of the invention include antibodies and fragments thereof, and in particular, antibodies capable of binding a therapeutic target involved in amyloidogenic disease or disorder. Accordingly, the therapeutic polypeptides are stabilized according to the invention to avoid the formation of by-products, typically high molecular weight aggregates, low molecule weight degradation fragments, or a mixture thereof, by the addition of an antioxidant in a sufficient amount so as to inhibit the formation of such by-products. Antioxidant agents include methionine and analogs thereof, at concentrations sufficient to obtain the desired inhibition of undesired by-products as discussed below. Optionally, the stabilized polypeptide formulations of the invention further comprise a tonicity agent, where the tonicity agent is present in an amount sufficient to render the stabilized formulation suitable for several different routes of administration, for example, intravenous infusion, and an amino acid or derivative thereof, where the amino acid or derivative thereof is present in an amount sufficient to maintain a physiologically suitable pH. In an exemplary embodiment, the present invention provides a stabilized formulation including an anti Aβ antibody, methionine, mannitol and histidine.

In one embodiment, the present invention provides a stabilized liquid formulation including a therapeutically active Aβ binding polypeptide, wherein the polypeptide is capable of by-product formation during storage and an antioxidant, where the antioxidant is present in an amount sufficient to reduce by-product formation during storage of the formulation. In an exemplary embodiment, the anti-oxidant is methionine or an analog thereof.

In some embodiments of the invention, the Aβ binding polypeptide is selected from the group consisting of an antibody, an antibody Fv fragment, an antibody Fab fragment, an antibody Fab'(2) fragment, an antibody Fd fragment, a single-chain antibody (scFv), a single domain antibody fragment (Dab), a beta-pleated sheet polypeptide including at least one antibody complementarity determining region (CDR), and a non-globular polypeptide including at least one antibody complementarity determining region. In exemplary embodiments of the invention, the Aβ binding polypeptide is present from about 0.1 mg/ml to about 60 mg/ml. In other exemplary embodiments, formulations of the present invention include Aβ binding polypeptide at about 30 mg/ml. In yet other exemplary embodiments, formulations of the present invention include Aβ binding polypeptide at about 20 mg/ml. In further exemplary embodiments, formulations of the invention include Aβ binding polypeptide at about 17 mg/ml.

In exemplary embodiments of the invention, the Aβ binding polypeptide is an anti Aβ antibody. In some embodiments of the present invention, the anti Aβ antibody is selected from the group consisting of a humanized 3D6 antibody, a humanized 10D5 antibody, a humanized 12B4 antibody, a humanized 266 antibody, a humanized 12A11 antibody, and a humanized 15C11 antibody. In exemplary embodiments of the present invention, the anti Aβ antibody binds to an epitope including Aβ amino acid residues selected from the group consisting of 1-7, 1-5, 3-7, 3-6, 13-28, 16-21, 19-22, 33-40, and 33-42. In some embodiments of the present invention, the anti Aβ antibody is of a subtype selected from the group consisting of human IgG1, IgG2, IgG3, and IgG4. In a particular embodiment of the present invention, the anti Aβ antibody is of a human IgG1 subtype.

The Aβ polypeptide may be capable of forming a by-product selected from the group consisting of a high molecular weight polypeptide aggregate, a low molecular weight polypeptide degradation product, and combinations thereof. The high molecular weight aggregates may include antibody:antibody complexes, antibody:antibody fragment complexes, antibody fragment:antibody fragment complexes, and combinations thereof. The low molecular weight polypeptide degradation product may include an antibody light chain, an antibody heavy chain, an antibody light chain and heavy chain complex, an antibody fragment, and combinations thereof.

In one embodiment of the present invention, a liquid formulation according to the present invention includes an Aβ binding polypeptide, mannitol and histidine. In an exemplary embodiment of the present invention, the Aβ binding polypeptide is an anti Aβ antibody. In some exemplary embodiments of the present invention, the anti Aβ antibody is selected from the group consisting of a humanized 3D6 antibody, a humanized 10D5 antibody, a humanized 12B4 antibody, a humanized 266 antibody, a humanized 12A11 antibody, and a humanized 15C11 antibody. In other exemplary embodiments of the present invention, the anti Aβ antibody binds to an epitope including Aβ amino acid residues selected from the group consisting of 1-7, 1-5, 3-7, 3-6, 13-28, 16-21, 19-22, 33-40, and 33-42. In some embodiments of the present invention, the antibody is of a subtype selected from the group consisting of IgG1, IgG2, IgG3, and IgG4. In a particular embodiment of the present invention, the antibody is of an IgG1 subtype.

In exemplary embodiments of the present invention, the anti Aβ antibody is present from about 0.1 mg/ml to about 200 mg/ml. In other exemplary embodiments of the present invention, the anti Aβ antibody is present at about 20 mg/ml.

In some embodiments of the present invention, formulations of the present invention include mannitol in an amount sufficient to maintain isotonicity of the formulation. In exemplary embodiments of the present invention, mannitol is present from about 2% w/v to about 10% w/v. In other exemplary embodiments of the present invention, mannitol is present at about 4% w/v. In yet other exemplary embodiments, mannitol is present at about 6% w/v. In further exemplary embodiments, mannitol is present at about 10% w/v.

In some embodiments of the present invention, formulations of the present invention include histidine in an amount sufficient to maintain a physiologically suitable pH. In exemplary embodiments of the present invention, histidine is present from about 0.1 mM to about 25 mM. In other exemplary embodiments, histidine is present at about 10 mM.

In one embodiment of the present invention, formulations of the present invention include succinate from about 0.1 mM to about 25 mM. In an exemplary embodiment of the present invention, succinate is present at about 10 mM.

In some embodiments of the present invention, formulations of the present invention further include an anti-oxidant. In exemplary embodiments, the anti-oxidant is methionine or an analog thereof. In one embodiment of the present invention, the methionine or analog is present at about 0.1 mM to about 25 mM. In another embodiment, the methionine or analog is present at about 10 mM.

In some embodiments of the invention, the formulation further includes a stabilizer. In exemplary embodiments of the present invention, the stabilizer is polysorbate 80. In some embodiments, the polysorbate 80 is present from about 0.001% w/v to about 0.01% w/v. In other embodiments, the polysorbate 80 is present at about 0.005% w/v. In yet other embodiments of the present invention, the polysorbate 80 is present at about 0.01% w/v.

In some embodiments of the invention, the formulation has a pH of about 5 to about 7. In exemplary embodiments of the present invention, the formulation has a pH of about 5.5. In another exemplary embodiment, the formulation has a pH of about 6.0. In yet another exemplary embodiment, the formulation has a pH of about 6.2. In further exemplary embodiments, the formulation has a pH of about 6.5.

In some embodiments, the formulation is stable to freezing. In other embodiments of the present invention, the formulation is suitable for intravenous administration. In an exemplary embodiment of the present invention, the formulation is suitable for intramuscular or subcutaneous administration. In an exemplary embodiment, the formulation is suitable for delivery to the brain of a subject.

In some embodiments of the present invention, the formulation is suitable for delivery to the spinal fluid of a subject. In other embodiments, the formulation is substantially free of preservatives.

In some embodiments of the present invention, the formulation is stable for at least about 12 months. In some embodiments, the formulation is stable for at least about 18 months. In some embodiments of the present invention, the formulation is stable for at least about 24 months. In some embodiments of the present invention, the formulation is stable for at least about 30 months.

In exemplary embodiments of the present invention, the formulation is stable from about −80° C. to about 40° C. In some exemplary embodiments, the formulation is stable from about 0° C. to about 25° C. Preferably, the formulation is stable from about 2° C. to about 8° C.

In a particular embodiment of the present invention, a formulation suitable for intravenous administration includes about 20 mg/mL anti Aβ antibody, about 10 mM L-histidine, about 10 mM methionine, about 4% mannitol and has a pH of about 6. In another particular embodiment, a formulation suitable for intravenous administration includes about 30 mg/mL anti Aβ antibody, about 10 mM L-histidine, about 10 mM methionine, about 6% mannitol and has a pH of about 6.2. A preferred formulation suitable for intravenous administration includes about 20 mg/mL anti Aβ antibody, about 10 mM L-histidine, about 10 mM methionine, about 4% mannitol, about 0.005% polysorbate 80, and has a pH of about 6. In a further exemplary embodiment of the present invention, a formulation suitable for intravenous administration includes about 10 mg/mL anti Aβ antibody, about 10 mM L-histidine, about 10 mM methionine, about 10% mannitol, about 0.005% polysorbate 80, and has a pH of about 6.5.

In some embodiments of the foregoing formulations according to the present invention, the anti Aβ antibody is selected from the group consisting of a humanized 3D6 antibody, a humanized 10D5 antibody, a humanized 12B4 antibody, a humanized 266 antibody, a humanized 12A11 antibody, and a humanized 15C11 antibody. In exemplary embodiments, the anti Aβ antibody binds to an epitope within amino acid residues selected from the group consisting of 1-7, 1-5, 3-7, 3-6, 13-28, 16-21, 19-22, 33-40, and 33-42 of Aβ. In some formulations, the anti Aβ antibody binds a discontinuous epitope which includes residues within 1-7 within 13-28 of Aβ. In some such formulations, the antibody is a bispecific antibody or an antibody made by the process described in International Patent Publication No. WO03/070760. In some such formulations, the epitope is a discontinuous epitope.

In another aspect of the present invention, a pharmaceutical unit dosage form includes an effective amount of the formulation of any of the foregoing embodiments for treating disease in a patient via administration of the dosage form to the patient. In an exemplary embodiment, the pharmaceutical unit dosage form is a container containing a formulation according to the present invention. In an exemplary embodiment, the container is a vial containing about 1 mg to about 2000 mg of the Aβ binding polypeptide. In another exemplary embodiment, the vial contains about 50 mg to about 1500 mg of the Aβ binding polypeptide. In a further exemplary embodiment, the vial contains about 5 mg to about 50 mg of the Aβ binding polypeptide.

In exemplary embodiments, the vial has a volume of about 2 to about 100 ml. In yet other embodiments, the vial has a volume of about 2 to about 10 ml.

In some embodiments, a pharmaceutical unit dosage form according to the present invention is suitable for intravenous infusion to a patient.

Also described herein are kits including a pharmaceutical unit dosage form, as described herein, and instructions for use. In one embodiment of the present invention, a container including the pharmaceutical unit dosage form of is a container labeled for use. In an exemplary embodiment, the container is labeled for prophylactic use. In another exemplary embodiment, the container is labeled for therapeutic use.

The present invention provides a method for increasing the stability of an Aβ binding polypeptide in a liquid pharmaceutical formulation, where the polypeptide exhibits by-product formation during storage in a liquid formulation, which method includes incorporating into the formulation an antioxidant in an amount sufficient to reduce the amount of by-product formation of the polypeptide. In exemplary embodiments, the Aβ binding polypeptide component is selected from the group consisting of an antibody, an antibody Fv fragment, an antibody Fab fragment, an antibody Fab'(2) fragment, an antibody Fd fragment, a single-chain antibody (scFv), a single domain antibody fragment (Dab), a beta-pleated sheet polypeptide including at least one antibody complementarity determining region (CDR), and a non-globular polypeptide including at least one antibody complementarity determining region. In one embodiment, the by-product is selected from the group consisting of a high molecular weight polypeptide aggregate, a low molecular weight polypeptide degradation product, and combinations thereof. In another embodiment, the antioxidant is selected from the group consisting of methionine and an analog thereof.

In some embodiments, a method for preparing a formulation according to any of the foregoing embodiments of the present invention includes combining the excipients of the formulation. In an exemplary embodiment, a method for preparing the formulation according to any of the foregoing embodiments includes combining the Aβ binding polypeptide with one or more diluents, where the one or more diluents include the excipients of the formulation.

In an exemplary embodiment, a method for preparing a pharmaceutical unit dosage form includes combining the formulation of any of foregoing embodiments in a suitable container. In another exemplary embodiment, a method for preparing the formulation of any of the foregoing embodiments includes combining a solution including the Aβ binding polypeptide and a least a portion of the excipients of the formulation with a diluent including the remainder of the excipients.

Polypeptides for use in the Stabilized Formulations of the Invention

The polypeptide to be formulated according to the invention as described herein is prepared using techniques which are well established in the art and include, for example, synthetic techniques (such as recombinant techniques and peptide synthesis or a combination of these techniques), or may be isolated from an endogenous source of the polypeptide. In certain embodiments of the invention, the polypeptide of choice is an antigen-binding polypeptide, more preferably, an antibody, and in particular, an anti-Aβ antibody. Techniques for the production of an antigen-binding polypeptide, and in particular, antibodies, are described below.

Polyclonal Antibodies

Polyclonal antibodies can be prepared by immunizing a suitable subject with an immunogen. The antibody titer in the immunized subject can be monitored over time by standard techniques, such as with an enzyme linked immunosorbent assay (ELISA) using immobilized target antigen. If desired, the antibody molecules directed against the target antigen can be isolated from the mammal (for example, from the blood) and further purified by well known techniques, such as protein A Sepharose chromatography to obtain the antibody, for example, IgG, fraction. At an appropriate time after immunization, for example, when the anti-antigen antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75). For the preparation of chimeric polyclonal antibodies, see Buechler et al. U.S. Pat. No. 6,420,113.

Monoclonal Antibodies

Any of the many well known protocols used for fusing lymphocytes and immortalized cell lines can be applied for the purpose of generating a monoclonal antibody (see, for example, G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (for example, a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, for example, the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a target antigen, for example, Aβ, using a standard ELISA assay.

Recombinant Antibodies

Alternative to preparing monoclonal antibody-secreting hybridomas, a monoclonal antibody can be identified and isolated by screening a recombinant combinatorial immunoglobulin library (for example, an antibody phage display library) with a target antigen to thereby isolate immunoglobulin library members that bind the target antigen. Kits for generating and screening phage display libraries are commercially available (for example, the *Pharmacia Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Chimeric and Humanized Antibodies

Additionally, recombinant antibodies, such as chimeric and humanized monoclonal antibodies, comprising both human and non-human portions, which can be made using standard recombinant DNA techniques, are within the scope of the invention.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (for example, at least one CDR, preferably two CDRs, more preferably three CDRs) substantially from a non-human immunoglobulin or antibody, and further includes constant regions (for example, at least one constant region or portion thereof, in the case of a light chain, and three constant regions in the case of a heavy chain). The term "humanized variable region" (for example, "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90%, 90-95%, or 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably at least 90-95%, more preferably, 96%, 97%, 98%, or 99% identical to that of a non-human organism, for example, a non-human mammal.

Accordingly, all regions or residues of a humanized immunoglobulin or antibody, or of a humanized immunoglobulin or antibody chain, except the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

The term "significant identity" means that two polypeptide sequences, when optimally aligned, such as by the programs GAP or BESTFIT using default gap weights, share at least 50-60% sequence identity, preferably at least 60-70% sequence identity, more preferably at least 70-80% sequence identity, more preferably at least 80-90% sequence identity, even more preferably at least 90-95% sequence identity, and even more preferably at least 95% sequence identity or more (for example, 99% sequence identity or more). The term "substantial identity" means that two polypeptide sequences, when optimally aligned, such as by the programs GAP or BESTFIT using default gap weights, share at least 80-90% sequence identity, preferably 90-95% sequence identity, and more preferably at least 95% sequence identity or more (for example, 99% sequence identity or more). For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

Preferably, residue positions which are not identical differ by conservative amino acid substitutions. For purposes of classifying amino acids substitutions as conservative or non-conservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Preferably, humanized immunoglobulins or antibodies bind antigen with an affinity that is within a factor of three, four, or five of that of the corresponding non-humanized antibody. For example, if the nonhumanized antibody has a binding affinity of $10^{-9}$ M, humanized antibodies will have a binding affinity of at least $3\times10^{-8}$ M, $4\times10^{-8}$ M, $5\times10^{-8}$ M, or $10^{-9}$ M. When describing the binding properties of an immunoglobulin or antibody chain, the chain can be described based on its ability to "direct antigen (for example, Aβ) binding". A chain is said to "direct antigen binding" when it confers upon an intact immunoglobulin or antibody (or antigen binding fragment thereof) a specific binding property or binding affinity. A mutation (for example, a backmutation) is said to substantially affect the ability of a heavy or light chain to direct antigen binding if it affects (for example, decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (for example, decrease) the ability of a chain to direct antigen binding" if it affects (for example, decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Human Antibodies from Transgenic Animals and Phase Display

Alternatively, it is now possible to produce transgenic animals (for example, mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germline mutant mice results in the production of human antibodies upon antigen challenge. See, for example, U.S. Pat. Nos. 6,150,584; 6,114,598; and 5,770,429.

Fully human antibodies can also be derived from phage-display libraries (Hoogenboom et al., *J. Mol. Biol.*, 227:381 (1991); Marks et al., *J. Mol. Biol.*, 222:581-597 (1991)). Chimeric polyclonal antibodies can also be obtained from phage display libraries (Buechler et al. U.S. Pat. No. 6,420,113).

Bispecific Antibodies, Antibody Fusion Polypeptides, and Single-Chain Antibodies Bispecific antibodies (BsAbs) are antibodies that have binding specificities for at least two different epitopes. Such antibodies can be derived from full length antibodies or antibody fragments (for example F(ab)'2 bispecific antibodies). Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of different antibody molecules (see, WO 93/08829 and in Traunecker et al., EMBO J., 10:3655-3659 (1991)).

Bispecific antibodies also include cross-linked or "heteroconjugate" antibodies. For example, one of the antibodies in the heteroconjugate can be coupled to avidin, the other to biotin or other payload. Heteroconjugate antibodies may be made using any convenient cross-linking methods. Suitable cross-linking agents are well known in the art, and are disclosed in U.S. Pat. No. 4,676,980, along with a number of cross-linking techniques.

In yet another embodiment, the antibody can be fused, chemically or genetically, to a payload such as a reactive, detectable, or functional moiety, for example, an immunotoxin to produce an antibody fusion polypeptide. Such payloads include, for example, immunotoxins, chemotherapeutics, and radioisotopes, all of which are well-known in the art.

Single chain antibodies are also suitable for stabilization according to the invention. The fragments comprise a heavy-chain variable domain (VH) connected to a light-chain variable domain (VL) with a linker, which allows each variable region to interface with each other and recreate the antigen binding pocket of the parent antibody from which the VL and VH regions are derived. See Gruber et al., J. Immunol., 152: 5368 (1994).

It is understood that any of the foregoing polypeptide molecules, alone or in combination, are suitable for preparation as stabilized formulations according to the invention.

Anti Aβ Antibodies

Generally, the formulations of the present invention include a variety of antibodies for treating amyloidogenic diseases, in particular, Alzheimer's Disease, by targeting Aβ peptide.

The terms "Aβ antibody", "anti Aβ antibody" and "anti Aβ" are used interchangeably herein to refer to an antibody that binds to one or more epitopes or antigenic determinants of the human amyloid precursor protein (APP), Aβ protein, or both. Exemplary epitopes or antigenic determinants can be found within APP, but are preferably found within the Aβ peptide of APP. Multiple isoforms of APP exist, for example APP$^{695}$, APP$^{751}$ and APP$^{770}$. Amino acids within APP are assigned numbers according to the sequence of the APP$^{770}$ isoform (see for example, GenBank Accession No. P05067). Examples of specific isotypes of APP which are currently known to exist in humans are the 695 amino acid polypeptide described by Kang et. al. (1987) *Nature* 325:733-736 which is designated as the "normal" APP; the 751 amino acid polypeptide described by Ponte et al. (1988) *Nature* 331:525-527 (1988) and Tanzi et al. (1988) *Nature* 331:528-530; and the 770-amino acid polypeptide described by Kitaguchi et. al. (1988) *Nature* 331:530-532. As a result of proteolytic processing of APP by different secretase enzymes in vivo or in situ, Aβ is found in both a "short form", 40 amino acids in length, and a "long form", ranging from 42-43 amino acids in length. The short form, Aβ$_{40}$, consists of residues 672-711 of APP. The long form, for example, Aβ$_{42}$ or Aβ$_{43}$, consists of residues 672-713 or 672-714, respectively. Part of the hydrophobic domain of APP is found at the carboxy end of Aβ, and may account for the ability of Aβ to aggregate, particularly in the case of the long form. Aβ peptide can be found in, or purified from, the body fluids of humans and other mammals, for example cerebrospinal fluid, including both normal individuals and individuals suffering from amyloidogenic disorders.

The terms "β-amyloid protein", "β-amyloid peptide", "β-amyloid", "Aβ" and "Aβ peptide" are used interchangeably herein. Aβ peptide (for example, Aβ39, Aβ40, Aβ41, Aβ42 and Aβ43) is a ~4-kDa internal fragment of 39-43 amino acids of APP. Aβ40, for example, consists of residues 672-711 of APP and Aβ42 consists of residues 672-713 of APP. Aβ peptides include peptides resulting from secretase cleavage of APP and synthetic peptides having the same or essentially the same sequence as the cleavage products. Aβ peptides can be derived from a variety of sources, for example, tissues, cell lines, or body fluids (for example sera or cerebrospinal fluid). For example, an Aβ can be derived from APP-expressing cells such as Chinese hamster ovary (CHO) cells stably transfected with APP$_{717V \rightarrow F}$, as described, for example, in Walsh et al., (2002), *Nature*, 416, pp 535-539. An Aβ preparation can be derived from tissue sources using methods previously described (see, for example, Johnson-Wood et al., (1997), *Proc. Natl. Acad. Sci. USA* 94:1550). Alternatively, Aβ peptides can be synthesized using methods which are well known to those in the art. See, for example, Fields et al., Synthetic Peptides: A User's Guide, ed. Grant, W.H. Freeman & Co., New York, N.Y., 1992, p 77). Hence, peptides can be synthesized using the automated Merrifield techniques of solid phase synthesis with the α-amino group protected by either t-Boc or F-moc chemistry using side chain protected amino acids on, for example, an Applied Biosystems Peptide Synthesizer Model 430A or 431. Longer peptide antigens can be synthesized using well known recombinant DNA techniques. For example, a polynucleotide encoding the peptide or fusion peptide can be synthesized or molecularly cloned and inserted in a suitable expression vector for the transfection and heterologous expression by a suitable host cell. Aβ peptide also refers to related Aβ sequences that results from mutations in the Aβ region of the normal gene.

Exemplary epitopes or antigenic determinants to which an Aβ antibody binds can be found within the human amyloid precursor protein (APP), but are preferably found within the Aβ peptide of APP. Exemplary epitopes or antigenic determinants within Aβ are located within the N-terminus, central region, or C-terminus of Aβ. An "N-terminal epitope", is an epitope or antigenic determinant located within or including the N-terminus of the Aβ peptide. Exemplary N-terminal epitopes include residues within amino acids 1-10 or 1-12 of Aβ, preferably from residues 1-3, 1-4, 1-5, 1-6, 1-7, 2-6, 2-7, 3-6, or 3-7 of Aβ42. Other exemplary N-terminal epitopes start at residues 1-3 and end at residues 7-11 of Aβ. Additional exemplary N-terminal epitopes include residues 2-4, 5, 6, 7 or 8 of Aβ, residues 3-5, 6, 7, 8 or 9 of Aβ, or residues 4-7, 8, 9 or 10 of Aβ42. "Central epitopes" are epitopes or antigenic determinants comprising residues located within the central or mid-portion of the Aβ peptide. Exemplary central epitopes include residues within amino acids 13-28 of Aβ, preferably from residues 14-27, 15-26, 16-25, 17-24, 18-23, or 19-22 of Aβ. Other exemplary central epitopes include residues within amino acids 16-24, 16-23, 16-22, 16-21, 18-21, 19-21, 19-22, 19-23, or 19-24 of Aβ. "C-terminal" epitopes or antigenic determinants are located within or including the C-terminus of the Aβ peptide and include residues within amino acids 33-40, 33-41, or 33-42 of Aβ. "C-terminal epitopes" are epitopes or antigenic determinants comprising residues located within the C-terminus of the Aβ peptide (for example, within about amino acids 30-40 or 30-42 of Aβ. Additional exemplary C-terminal epitopes or antigenic determinants include residues 33-40 or 33-42 of Aβ.

When an antibody is said to bind to an epitope within specified residues, such as Aβ 3-7, what is meant is that the antibody specifically binds to a polypeptide containing the specified residues (i.e., Aβ 3-7 in this an example). Such an antibody does not necessarily contact every residue within Aβ

3-7. Nor does every single amino acid substitution or deletion within Aβ 3-7 necessarily significantly affect binding affinity. In various embodiments, an Aβ antibody is end-specific. As used herein, the term "end-specific" refers to an antibody which specifically binds to the N-terminal or C-terminal residues of an Aβ peptide but that does not recognize the same residues when present in a longer Aβ species comprising the residues or in APP. In various embodiments, an Aβ antibody is "C-terminus-specific." As used herein, the term "C terminus-specific" means that the antibody specifically recognizes a free C-terminus of an Aβ peptide. Examples of C terminus-specific Aβ antibodies include those that: recognize an Aβ peptide ending at residue 40 but do not recognize an Aβ peptide ending at residue 41, 42, and/or 43; recognize an Aβ peptide ending at residue 42 but do not recognize an Aβ peptide ending at residue 40, 41, and/or 43; etc.

In one embodiment, the Aβ antibody may be a 3D6 antibody or variant thereof, or a 10D5 antibody or variant thereof, both of which are described in U.S. Patent Publication No. 20030165496A1, U.S. Patent Publication No. 20040087777A1, International Patent Publication No. WO02/46237A3 and International Patent Publication No. WO04/080419A2. Description of 3D6 and 10D5 antibodies can also be found, for example, in International Patent Publication No. WO02/088306A2 and International Patent Publication No. WO02/088307A2. Additional 3D6 antibodies are described in U.S. patent application Ser. No. 11/303,478 and International Application No. PCT/US05/45614. 3D6 is a monoclonal antibody (mAb) that specifically binds to an N-terminal epitope located in the human β-amyloid peptide, specifically, residues 1-5. By comparison, 10D5 is a mAb that specifically binds to an N-terminal epitope located in the human β-amyloid peptide, specifically, residues 3-6. A cell line producing the 3D6 monoclonal antibody (RB96 3D6.32.2.4) was deposited with the American Type Culture Collection (ATCC), Manassas, Va. 20108, USA on Apr. 8, 2003 under the terms of the Budapest Treaty and has deposit number PTA-5130. A cell line producing the 10D5 monoclonal antibody (RB44 10D5.19.21) was deposited with the ATCC on Apr. 8, 2003 under the terms of the Budapest Treaty and has deposit number PTA-5129.

Exemplary variant 3D6 antibodies are those having, for example, a humanized light chain comprising variable region amino acid sequences set forth as SEQ ID NO:3 or SEQ ID NO:5 and a humanized heavy chain comprising variable region amino acid sequences set forth as SEQ ID NO:4 or SEQ ID NO:6. Other exemplary variant 3D6 antibodies are those having, for example, a humanized light chain amino acid sequence set forth as SEQ ID NO:7 and a humanized heavy chain amino acid sequence set forth as SEQ ID NO:8.

Exemplary variant 10D5 antibodies are those having, for example, a humanized light chain comprising variable region amino acid sequences set forth as SEQ ID NO:9 or SEQ ID NO:11 and a humanized heavy chain comprising variable region amino acid sequences set forth as SEQ ID NO:10 or SEQ ID NO:12. Other exemplary variant 10D5 antibodies are those having, for example, a humanized light chain amino acid sequence set forth as SEQ ID NO:13 and a humanized heavy chain amino acid sequence set forth as SEQ ID NO:14. Such variant antibodies are further described in WO02/088306A2.

In another embodiment, the antibody may be a 12B4 antibody or variant thereof, as described in U.S. Patent Publication No. 20040082762A1 and International Patent Publication No. WO03/077858A2. 12B4 is a mAb that specifically binds to an N-terminal epitope located in the human β-amyloid peptide, specifically, residues 3-7.

Exemplary variant 12B4 antibodies are those having, for example, a humanized light chain (or light chain) comprising variable region amino acid sequences set forth as SEQ ID NO:15 or SEQ ID NO:17 and a humanized heavy chain comprising variable region amino acid sequences set forth as SEQ ID NO:16, SEQ ID NO:18 or SEQ ID NO:19.

In yet another embodiment, the antibody may be a 12A11 antibody or a variant thereof, as described in U.S. Patent Publication No. 20050118651A1, U.S. patent application Ser. No. 11/303,478, International Patent Publication No. WO04/108895A2, and International Patent Application Serial No. PCT/US05/45614. 12A11 is a mAb that specifically binds to an N-terminal epitope located in the human β-amyloid peptide, specifically, residues 3-7. A cell line producing the 12A11 monoclonal antibody was deposited with the ATCC on Dec. 12, 2005 under the terms of the Budapest Treaty and has deposit number PTA-7271.

Exemplary variant 12A11 antibodies are those having, for example, a humanized light chain comprising the variable region amino acid sequence set forth as SEQ ID NO:20 and a humanized heavy chain comprising variable region amino acid sequences set forth as SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41.

In yet another embodiment, the antibody may be a 6C6 antibody, or a variant thereof, as described in a U.S. patent application Ser. No. 11/304,986 and International Patent Application No. PCT/US05/45515 entitled "Humanized Antibodies that Recognize Beta Amyloid Peptide." 6C6 is a mAb that specifically binds to an N-terminal epitope located in the human β-amyloid peptide, specifically, residues 3-7. A cell line producing the antibody 6C6 was deposited on Nov. 1, 2005, with the ATCC under the terms of the Budapest Treaty and assigned accession number PTA-7200.

In yet another embodiment, the antibody may be a 2H3 antibody as described in U.S. patent application Ser. No. 11/304,986 and International Patent Application No. PCT/US05/45515 entitled "Humanized Antibodies that Recognize Beta Amyloid Peptide.". 2H3 is a mAb that specifically binds to an N-terminal epitope located in the human β-amyloid peptide, specifically, residues 2-7.

In yet another embodiment, the antibody may be a 3A3 antibody as described in U.S. patent application Ser. No. 11/305,899. 3A3 is a mAb that specifically binds to an N-terminal epitope located in the human β-amyloid peptide, specifically, residues 3-7.

Cell lines producing the antibodies 2H3 and 3A3, having the ATCC accession numbers PTA-7267 and PTA-7269, respectively, were deposited on Dec. 12, 2005 under the terms of the Budapest Treaty.

In yet another embodiment, the antibody may be a 15C11 antibody or variant thereof, as described in U.S. patent application No. 11/304,986 and International Patent Application No. PCT/US05/45515 entitled "Humanized Antibodies that Recognize Beta Amyloid Peptide." 15C11 is a mAb that specifically binds to a central epitope located in the human β-amyloid peptide, specifically, residues 19-22. A cell line producing the 15C11 monoclonal antibody was deposited with the ATCC on Dec. 12, 2005 under the terms of the Budapest Treaty and has deposit number PTA-7270.

In yet another embodiment, the antibody may be a 266 antibody as described in U.S. Patent Publication No. 20050249725A1, and International Patent Publication No.

WO01/62801A2. 266 is a mAb that specifically binds to a central epitope located in the human β-amyloid peptide, specifically, residues 16-24. A cell line producing the 266 monoclonal antibody was deposited with the ATCC on Jul. 20, 2004 under the terms of the Budapest Treaty and has deposit number PTA-6123.

Exemplary variant 266 antibodies are those having, for example, a humanized light chain comprising variable region amino acid sequences set forth as SEQ ID NO:42 or SEQ ID NO:44 and a humanized heavy chain comprising variable region amino acid sequences set forth as SEQ ID NO:43 or SEQ ID NO:45. Other exemplary variant 266 antibodies are those having, for example, a humanized light chain amino acid sequence set forth as SEQ ID NO:46 and a humanized heavy chain amino acid sequence set forth as SEQ ID NO:47. Such variant antibodies are further described in U.S. Patent Publication No. 20050249725A1, and International Patent Publication No. WO01/62801A2.

In yet another embodiment, the antibody may be a 2B1 antibody, or a variant thereof, as described in a U.S. patent application Ser. No. 11/304,986 and International Patent Application No. PCT/US05/45515 entitled "Humanized Antibodies that Recognize Beta Amyloid Peptide." 2B1 is a mAb that specifically binds to a central epitope located in the human β-amyloid peptide, specifically, residues 19-23.

In yet another embodiment, the antibody may be a 1C2 antibody, or a variant thereof, as described in a U.S. patent application Ser. No. 11/304,986 and International Patent Application No. PCT/US05/45515 entitled "Humanized Antibodies that Recognize Beta Amyloid Peptide." 1C2 is a mAb that specifically binds to a central epitope located in the human β-amyloid peptide, specifically, residues 16-23.

In yet another embodiment, the antibody may be a 9G8 antibody, or a variant thereof, as described in a U.S. patent application Ser. No. 11/304,986 and International Patent Application No. PCT/US05/45515 entitled "Humanized Antibodies that Recognize Beta Amyloid Peptide.". 9G8 is a mAb that specifically binds to a central epitope located in the human β-amyloid peptide, specifically, residues 16-21.

Cell lines producing the antibodies antibodies 2B1, 1C2 and 9G8 were deposited on Nov. 1, 2005, with the ATCC under the terms of the Budapest Treaty and were assigned accession numbers PTA-7202, PTA-7199 and PTA-7201, respectively.

Antibodies that specifically bind to C-terminal epitopes located in human β-amyloid peptide, for use in the present invention include, but are not limited to, 369.2B, as described in U.S. Pat. No. 5,786,180, entitled "Monoclonal antibody 369.2B specific for β A4 peptide." Further description of antibodies for use in the present invention can be found in, for example, Bussiere et al., (Am. J. Pathol. 165(3):987-95 (2004)) Bard et al. (PNAS 100(4):2023-8 (2003)), Kajkowski et al. (J. Biol. Chem. 276(22):18748-56 (2001)), Games et al. (Ann. NY Acad. Sci. 920:274-84 (2000)), Bard et al. (Nat. Med. 6(8):916-9 (2000)), and in International Patent Application No. WO03015691A2 entitled "Effecting rapid improvement of cognition in a subject having Alzheimer's disease, Down's syndrome, cerebral amyloid angiopathy, or mild cognitive impairment, comprises administering anti-A beta antibody". Further description of antibody fragments for use in the present invention can be found in, for example, Bales et al. (Abstract P4-396, page S587, presented at Poster Session P4: Therapeutics and Therapeutic Strategies-Therapeutic Strategies, Amyloid-Based) and Zameer et al. (Abstract P4-420, page S593, presented at Poster Session P4: Therapeutics and Therapeutic Strategies-Therapeutic Strategies, Amyloid-Based).

Antibodies for use in the present invention may be recombinantly or synthetically produced. For example, the antibody may be produced by a recombinant cell culture process, using, for example, CHO cells, NIH 3T3 cells, PER.C6® cells, NS0 cells, VERO cells, chick embryo fibroblasts, or BHK cells. In addition, antibodies with minor modifications that retain the primary functional property of binding Aβ peptide are contemplated by the present invention. In a particular embodiment, the antibody is a humanized anti Aβ peptide 3D6 antibody that selectively binds Aβ peptide. More specifically, the humanized anti Aβ peptide 3D6 antibody is designed to specifically bind to an $NH_2$-terminal epitope, for example, amino acid residues 1-5, located in the human β-amyloid 1-40 or 1-42 peptide found in plaque deposits in the brain (for example, in patients suffering from Alzheimer's disease).

FIG. 1 provides a schematic representation of the predicted structure of an exemplary humanized anti Aβ peptide antibody. The complete amino acid sequences of the h3D6v2 light and heavy chains predicted from the DNA sequences of the corresponding expression vectors are shown in FIG. 2 (where the residues are numbered starting with the $NH_2$-terminus of light and heavy chains as residue number 1) and in SEQ ID NO: 1 and SEQ ID NO:2, respectively. The last amino acid residue encoded by the heavy chain DNA sequence, $Lys^{449}$, has not been observed in the mature, secreted form of h3D6v2 and, without wishing to be bound to any particular theory, is presumably removed during intracellular processing by CHO cellular proteases. Therefore, the COOH-terminus of the h3D6v2 heavy chain is optionally $Gly^{448}$. COOH-terminal lysine processing has been observed in recombinant and plasma-derived antibodies and does not appear to impact their function (Harris (1995) *J. Chromatogr. A.* 705:129-134). Purified h3D6v2 is post-translationally modified by addition of N-linked glycans to the Fc portion of heavy chain, which is known to contain a single N-glycosylation consensus site. The N-glycosylation site displays three major complex biantennary neutral oligosaccharide structures commonly observed at the analogous N-glycosylation site of mammalian IgG proteins.

Another exemplary humanized anti Aβ peptide antibody is humanized 3D6 version 1 (hu3D6v1) having the sequence set forth in FIG. 2 but for a D→Y substitution at position 1 of the light chain.

In various embodiments of the present invention, the anti Aβ antibody (for example, a humanized anti Aβ peptide 3D6 antibody) is present from about 0.1 mg/ml to about 100 mg/ml, from about 0.1 mg/ml to about 75 mg/ml, from about 0.1 mg/ml to about 50 mg/ml, from about 0.1 mg/ml to about 40 mg/ml, from about 0.1 mg/ml to about 30 mg/ml, from about 10 mg/ml to about 20 mg/ml, from about 20 mg/ml to 30 mg/ml, or higher, for example, up to about 100 mg/ml, about 200 mg/ml, about 500 mg/ml, or about 1000 mg/ml or more. Preferably the anti Aβ antibody is present in a concentration of about 17 mg/ml to about 23 mg/ml. In various embodiments, the anti Aβ antibody is present at about 1, 2, 5, 10, 15, 16, 17, 18, 19, 20, 21, 22, 23, 24, 25 or 30 mg/ml. In a particular embodiment, the antibody (for example, a humanized anti Aβ peptide 3D6 antibody) is present at about 17 mg/ml. In another particular embodiment, the antibody (for example, a humanized anti Aβ peptide 3D6 antibody) is present at about 20 mg/ml. In another particular embodiment, the antibody (for example, a humanized anti Aβ peptide 3D6 antibody) at about 30 mg/ml. Ranges intermediate to the above recited concentrations, for example, about 12 mg/ml to about 17 mg/ml, are also intended to be part of this invention.

For example, ranges of values using a combination of any of the above recited values as upper and/or lower limits are intended to be included.

Excipients

In various embodiments, the present invention provides a formulation that may include various excipients, including, but not limited to, buffer, anti-oxidant, a tonicity agent, and a stabilizer. In addition, the formulations may contain an additional agent for pH adjustment (for example, HCl) and a diluent (for example, water). In other embodiment, different forms of histidine can be used for pH adjustment. In part, the excipients serve to maintain the stability and the biological activity of the antibody (for example, by maintaining the proper conformation of the protein), and/or to maintain pH.

Buffering Agent

In various aspects of the present invention, the formulation includes a buffering agent (buffer). The buffer serves to maintain a physiologically suitable pH. In addition, the buffer can serve to enhance isotonicity and chemical stability of the formulation. Generally, the formulation should have a physiologically suitable pH. In various embodiments of the present invention, the formulation has a pH of about 5 to about 7, about 5.5 to about 6.5, preferably about 6.0 to about 6.5. In a particular embodiment, the formulation has a pH of about 6. Ranges intermediate to the above recited pH levels, for example, about pH 5.2 to about pH 6.3, preferably 6.0 or pH 6.2), are also intended to be part of this invention. For example, ranges of values using a combination of any of the above recited values as upper and/or lower limits are intended to be included. The pH may be adjusted as necessary by techniques known in the art. For example, HCl may be added as necessary to adjust the pH to desired levels or different forms of histidine may be used to adjust the pH to desired levels.

The buffer may include, but is not limited to, succinate (sodium or phosphate), histidine, phosphate(sodium or potassium), Tris(tris(hydroxymethyl)aminomethane), diethanolamine, citrate, other organic acids and mixtures thereof. In a preferred embodiment, the buffer is histidine (for example, L-histidine). In another particular embodiment, the buffer is succinate. In another embodiment, the formulation includes an amino acid such as histidine that is present in an amount sufficient to maintain the formulation at a physiologically suitable pH. Histidine is an exemplary amino acid having buffering capabilities in the physiological pH range. Histidine derives its buffering capabilities spanning from its imidazole group. In one exemplary embodiment, the buffer is L-histidine (base) (for example $C_6H_9N_3O_2$, FW: 155.15). In another embodiment, the buffer is L-histidine monochloride monohydrate (for example $C_6H_9N_3O_2 \cdot HCl \cdot H_2O$, FW: 209.63). In another exemplary embodiment, the buffer is a mixture of L-histidine (base) and L-histidine monochloride monohydrate.

In one embodiment, the buffer (for example, L-histidine or succinate) concentration is present from about 0.1 mM to about 50 mM, from about 0.1 mM to about 40 mM, from about 0.1 mM to about 30 mM, about 0.1 mM to about 25 mM, from about 0.1 mM to about 20 mM, or from about 5 mM to about 15 mM, preferably 5 mM or 10 mM. In various embodiments, the buffer may be present at about 6 mM, 7 mM, 8 mM, 9 mM, 11 mM, 12 mM, 13 mM, 14 mM, or 15 mM. In a particular embodiment, the buffer is present at about 10 mM. Ranges intermediate to the above recited concentrations, for example, about 12 mM to about 17 mM, are also intended to be part of this invention. For example, ranges of values using a combination of any of the above recited values as upper and/or lower limits are intended to be included. In certain embodiments, the buffer is present in an amount sufficient to maintain a physiologically suitable pH.

Tonicity Agent

In various aspects of the present invention, the formulation includes a tonicity agent. In part, the tonicity agent contributes to maintaining the isotonicity of the formulation, and to maintaining protein levels. In part, the tonicity agent contributes to preserving the level, ratio, or proportion of the therapeutically active polypeptide present in the formulation. As used herein, the term "tonicity" refers to the behavior of biologic components in a fluid enviornment or solution. Isotonic solutions possess the same osmotic pressure as blood plasma, and so can be intravenously infused into a subject without changing the osmotic pressure of the subject's blood plasma. Indeed, in one embodiment according to the invention, tonicity agent is present in an amount sufficient to render the formulation suitable for intravenous infusion. Often, the tonicity agent serves as a bulking agent as well. As such, the agent may allow the protein to overcome various stresses such as freezing and shear.

The tonicity agent may include, but is not limited to, $CaCl_2$, NaCl, $MgCl_2$, lactose, sorbitol, sucrose, mannitol, trehalose, raffinose, polyethylene glycol, hydroxyethyl starch, glycine and mixtures thereof. In a preferred embodiment, the tonicity agent is mannitol (for example, D-mannitol, for example, $C_6H_{14}O_6$, FW: 182.17).

In one embodiment, the tonicity agent is present at about 2% to about 6% w/v, or about 3% to about 5% w/v. In another embodiment, the tonicity agent is present at about 3.5% to about 4.5% w/v. In another embodiment, the tonicity agent is precent at about 20 mg/ml to about 60 mg/ml, at about 30 mg/ml to about 50 mg/ml, or at about 35 mg/ml to about 45 mg/ml. Preferably, the tonicity agent is present at about 4% w/v or at about 40 mg/ml. In another particular embodiment, the tonicity agent is present at about 6% w/v. In yet another particular embodiment, the tonicity agent is present at about 10% w/v.

Ranges intermediate to the above recited concentrations, for example, about 3.2% to about 4.3% w/v or about 32 to about 43 mg/ml, are also intended to be part of this invention. For example, ranges of values using a combination of any of the above recited values as upper and/or lower limits are intended to be included. The tonicity agent should be present in a sufficient amount so as to maintain tonicity of the formulation.

Anti-Oxidant

In various aspects of the present invention, the formulation includes an anti-oxidant so as to, in part, preserve the formulation (for example, by preventing oxidation).

The anti-oxidant may include, but is not limited to, GLA (gamma-linolenic acid)-lipoic acid, DHA (docosahexaenoic acid)-lipoic acid, GLA-tocopherol, di-GLA-3,3'-thiodipropionic acid and in general any of, for example, GLA, DGLA (dihomo-gamma-linolenic acid), AA (arachidonic acid), SA (salicylic acid), EPA (eicosapentaenoic acid) or DHA (docosahexaenoic acid) with any natural or synthetic antioxidant with which they can be chemically linked. These include phenolic anti-oxidants (for example, eugenol, carnosic acid, caffeic acid, BHT (butylated hydroxyanisol), gallic acid, tocopherols, tocotrienols and flavenoid anti-oxidants (such as myricetin and fisetin)), polyenes (for example, retinoic acid), unsaturated sterols (for example, $\Delta^5$-avenosterol), organosulfur compounds (for example, allicin), terpenes (for example, geraniol, abietic acid) and amino acid antioxidants (for example, methionine, cysteine, carnosine). In one embodiment, the anti-oxidant is ascorbic acid. Preferably, the anti-oxidant is methionine, or an analog thereof, for example, selenomethionine, hydroxy methyl butanoic acid, ethionine, or trifluoromethionine.

In one embodiment, the anti-oxidant (for example, a methionine such as L-methionine, for example $CH_3SCH_2CH_2CH(NH_2)CO_2H$, FW=149.21) is present from about 0.1 mM to about 50 mM, from about 0.1 mM to about 40 mM, from about 0.1 mM to about 30 mM, from about 0.1 mM to about 20 mM, or from about 5 mM to about 15 mM. In various embodiments, the anti-oxidant may be present at about 5 mM, 6 mM, 7 mM, 8 mM, 9 mM, 10 mM, 11 mM, 12 mM, 13 mM, 14 mM, or 15 mM. Preferably, the anti-oxidant is present at about 10 mM. In another particular embodiment, the anti-oxidant is present at about 15 mM. Ranges intermediate to the above recited concentrations, for example, about 12 mM to about 17 mM, are also intended to be part of this invention. For example, ranges of values using a combination of any of the above recited values as upper and/or lower limits are intended to be included. In certain embodiments, the anti-oxidant should be present in a sufficient amount so as to preserve the formulation, in part, by preventing oxidation.

Stabilizer

In various aspects of the present invention, the formulation includes a stabilizer, also known as a surfactant. Stabilizers are specific chemical compounds that interact and stabilize biological molecules and/or general pharmaceutical excipients in a formulation. In certain embodiments, stabilizers may be used in conjunction with lower temperature storage. Stabilizers generally protect the protein from air/solution interface induced stresses and solution/surface induced stresses, which may otherwise result in protein aggregation.

The stabilizer may include, but is not limited to, glycerin, polysorbates such as polysorbate 80, dicarboxylic acids, oxalic acid, succinic acid, adipic acid, fumaric acid, phthalic acids, and combinations thereof. In a preferred embodiment the stabilizer is polysorbate 80.

In one embodiment, the stabilizer (for example, polysorbate 80) concentration is about 0.001% w/v to about 0.01% w/v, about 0.001% w/v to about 0.009% w/v, or about 0.003% w/v to about 0.007% w/v. Preferably, the stabilizer concentration is about 0.005% w/v. In another particular embodiment, the stabilizer is present at about 0.01% w/v. Ranges intermediate to the above recited concentrations, for example, about 0.002% w/v to about 0.006% w/v, are also intended to be part of this invention. For example, ranges of values using a combination of any of the above recited values as upper and/or lower limits are intended to be included. The stabilizer should be present in a sufficient amount so as to stabilize the Aβ binding polypeptide (for example, anti Aβ antibody).

Other pharmaceutically acceptable carriers, excipients or stabilizers such as those described in Remington's Pharmaceutical Sciences 16$^{th}$ edition, Osol, A. Ed. (1980) may be included in the formulation provided that they do not adversely affect the desired characteristics of the formulation. In a particular embodiment, the formulation is substantially free of preservatives, although, in alternative embodiments, preservatives may be added as necessary. For example, cryoprotectants or lyoprotectants may be included, for example, should the formulation be lyophilized.

In various aspects of the present invention, the formulations optionally include some or all of the classes of excipients described above. In one aspect, the formulations of the present invention include Aβ binding polypeptide (for example, anti Aβ antibody), mannitol and histidine. In particular embodiments, the formulations may include an anti-oxidant such as methionine, and/or a stabilizer such as polysorbate 80. In certain embodiments, the formulations have a pH of about 6. In another aspect, the formulation includes an Aβ binding polypeptide (for example, an anti Aβ antibody), mannitol, histidine and methionine. In yet another aspect, the formulation includes an Aβ binding polypeptide (for example, an anti Aβ antibody), mannitol, histidine, methionine and polysorbate 80. In a particular aspect of the invention, the formulation includes about 20 mg/ml an Aβ binding polypeptide (for example, an anti Aβ antibody), about 10 mM histidine, about 10 mM methionine, about 4% mannitol and has a pH of about 6. In another aspect of the invention, the formulation includes about 20 mg/ml Aβ binding polypeptide (for example, anti Aβ antibody), 10 mM histidine, 10 mM methionine, 4% w/v mannitol, 0.005% w/v polysorbate 80 and has a pH of about 6. A preferred formulation includes about 17 mg/ml to about 23 mg/ml of a humanized 3D6 antibody, about 10 mM histidine, about 10 mM methionine, about 4% w/v mannitol, about 0.005% polysorbate 80 and has a pH of about 5.5 to about 6.5. Another preferred formulation includes about 10 mg/ml to about 30 mg/ml of a humanized 266 antibody, about 10 mM histidine or succinate, about 10 mM methionine, about 4% w/v mannitol or sorbitol and has a pH of about 5.5 to about 6.5. Yet another preferred formulation includes about 10 mg/ml to about 30 mg/ml of a humanized 12A11 antibody, about 5 mM histidine, about 10 mM methionine, about 4% mannitol or 150 mM NaCl, and has a pH of about 5.5 to about 6.5. Another formulation is stable for at least about 12 months at a temperature of above freezing to about 10° C., has a pH of about 5.5 to about 6.5, and includes at least one anti Aβ antibody at a concentration of about 1 mg/ml to about 30 mg/ml, mannitol at a concentration of about 4% w/v or NaCl at a concentration of about 150 mM, about 5 mM to about 10 mM histidine or succinate, and 10 mM methionine. Preferably, the formulation also includes polysorbate at a concentration of about 0.001% w/v to about 0.01% w/v.

Exemplary embodiments of the present invention provide concentrated preparations of Aβ binding polypeptide (for example, anti Aβ antibody), often useful as bulk drug product. Furthermore, exemplary embodiments of the present invention are stable to freezing, lyophilization and/or reconstitution. Moreover, exemplary embodiments of the present invention are stable over extended periods of time. For example, the formulations of the present invention are stable for at least about 6, 7, 8, 9, 10, 11, 12, 13, 14, 15, 16, 17, 18, 19, 20, 21, 22, 23, 24, 25, 26, 27, 28, 29, or 30 months. In particular embodiments, the formulations of the present invention are stable for at least about 12 months, for at least about 18 months, for at least about 24 months, or for at least about 30 months.

According to the invention, the formulation may be stored at temperatures from about −80° C. to about 40° C., from about 0° C. to about 25° C., from about 0° C. to about 15° C., or from about 0° C. to about 10° C., preferably from about 2° C. to about 8° C. In various embodiments, the formulation may be stored at about 0° C., 1° C., 2° C., 3° C., 4° C., 5° C., 6° C., 7° C., 8° C., 9° C. or 10° C. In a particular embodiment, the formulation is stored at about 5° C. Generally, the formulation is stable and retains biological activity at these ranges. Ranges intermediate to the above recited temperatures, for example, from about 2° C. to about 17° C., are also intended to be part of this invention. For example, ranges of values using a combination of any of the above recited values as upper and/or lower limits are intended to be included.

The formulations of the present invention are suitable for delivery by a variety of techniques. In certain embodiments, the formulation is administered parenterally, such as intravenously or intramuscularly. Additionally, one may target delivery of the formulation to the brain (for example, so that the antibody may cross the blood brain barrier) or the spinal fluid. In a particular embodiment, the formulation is administered intravenously.

Effective doses of the formulations of the present invention vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages need to be titrated to optimize safety and efficacy.

For passive immunization with an antibody, exemplary dosages are from about 0.0001 mg/kg to about 100 mg/kg, about 0.01 mg/kg to about 5 mg/kg, about 0.15 mg/kg to about 3 mg/kg, 0.5 mg/kg to about 2 mg/kg, preferably about 1 mg/kg to about 2 mg/kg of the host body weight. In some exemplary embodiments, dosages can be about 0.5, 0.6, 0.7, 0.75, 0.8, 0.9, 1.0, 1.2, 1.25, 1.3, 1.4, 1.5, 1.6, 1.7, 1.75, 1.8, 1.9, or 2.0 mg/kg. Other exemplary dosages for passive immunization are from about 1 mg/kg to about 20 mg/kg. In some exemplary embodiments, dosages can be about 5, 10, 15 or 20 mg/kg. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. Intervals can also be irregular as indicated by measuring blood levels of antibody to Aβ in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, formulations containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In some therapeutic applications, a relatively high dosage (for example, from about 0.5 or 1 to about 200 mg/kg of antibody per dose (for example 0.5, 1, 1.5, 2, 5, 10, 20, 25, 50, or 100 mg/kg), with dosages of from 5 to 25 mg/kg being more commonly used) at relatively short intervals is sometimes required until progression of the disease is reduced or terminated, and preferably until the patient shows partial or complete amelioration of symptoms of disease. Thereafter, the patent can be administered a prophylactic regime.

It is especially advantageous to provide the formulations of the invention in unit dosage form for ease of administration and uniformity of dosage. Formulations of the invention may be presented in capsules, ampules, lyophilized form, or in multi-dose containers. The term "container" refers to something, for example, a holder, receptacle, or vessel, into which an object or liquid can be placed or contained, for example, for storage. The unit dosage form may comprise any formulation described herein including suspensions, solutions or emulsions of the active ingredient together with formulating agents such as suspending, stabilizing and/or dispersing agents. In an exemplary embodiment, the pharmaceutical dosage unit form may be added to an intravenous drip bag (for example a 50 ml, 100 ml, or 250 ml, or 500 ml drip bag) with a suitable diluent, for example, sterile pyrogen-free water or saline solution, before administration to the patient, for example, by intravenous infusion. Some pharmaceutical unit dosage forms may require reconstitution with a suitable diluent prior to addition to an intravenous drip bag, particularly lyophilized forms. In exemplary embodiments, the pharmaceutical unit dosage form is a container containing a formulation described herein. For example, the container may be a 10 mL glass, type I, tubing vial. Generally, the container should maintain the sterility and stability of the formulation. For example, the vial may be closed with a serum stopper. Furthermore, in various embodiments, the container should be designed so as to allow for withdrawal of about 100 mg of formulation or active ingredient (for example, for single use). Alternatively, the container may be suitable for larger amounts of formulation or active ingredient, for example, from about 10 mg to about 5000 mg, from about 100 mg to about 1000 mg, and from about 100 mg to about 500 mg, about 40 mg to about 250 mg, about 60 mg to about 80 mg, about 80 mg to about 120 mg, about 120 mg to about 160 mg, or ranges or intervals thereof, for example, about 100 mg to about 200 mg. Ranges intermediate to the above recited amounts, for example, from about 25 mg to about 195 mg, are also intended to be part of this invention. For example, ranges of values using a combination of any of the above recited values as upper and/or lower limits are intended to be included. In a particular embodiment, the formulation often is supplied as a liquid in unit dosage form.

In another aspect, the present invention provides a kit including a pharmaceutical dosage unit form (for example, a container with a formulation disclosed herein), and instructions for use. Accordingly, the container and the kit may be designed to provide enough formulation for multiple uses. In various embodiments, the kit may further include diluent. The diluent may include excipients, separate or combined. For example, the diluent may include a tonicity modifier such as mannitol, a buffering agent such as histidine, a stabilizer such as polysorbate 80, an anti-oxidant such as methionine, and/or combinations thereof. The diluent may contain other excipients, for example, lyoprotectant, as deemed necessary by one skilled in the art.

Additional useful embodiments of the invention are set forth in the section of this application entitled "Summary of the Invention".

This invention is further illustrated by the following examples which should not be construed as limiting. The contents of all references, patents and published patent applications cited throughout this application, as well as the figures, are incorporated herein by reference.

EXAMPLES

In general, the practice of the present invention employs, unless otherwise indicated, conventional techniques of chemistry, molecular biology, recombinant DNA technology, immunology (especially, for example, antibody technology), and standard techniques of polypeptide preparation. See, for example, Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Example I

Cloning and Expression of Humanized Anti A Beta Antibody

An exemplary antibody for formulation according to the methods of the instant invention is 3D6. The 3D6 mAb is specific for the N-terminus of Aβ and has been shown to mediate phagocytosis (for example, induce phagocytosis) of amyloid plaque. 3D6 does not recognize secreted APP or full-length APP, but detects only Aβ species with an amino-terminal aspartic acid. Therefore, 3D6 is an end-specific antibody. The cell line designated RB96 3D6.32.2.4 producing the antibody 3D6 has the ATCC accession number PTA-5130, having been deposited on Apr. 8, 2003. The cloning, characterization and humanization of 3D6 antibody is described in U.S. Patent Application Publication No. 20030165496 A1. Briefly, humanization of the anti Aβ peptide murine monoclonal antibody (designated as m3D6) was carried out by isolating the DNA sequences for m3D6 light chain and heavy chain variable regions ($V_L$ and $V_H$) by reverse transcription-polymerase chain reaction (RT-PCR). Based on the determined m3D6 $V_L$ and $V_H$ DNA sequences, homologous human framework regions were identified. To insure that the humanized antibody retained the ability to interact with the Aβ peptide antigen, critical murine $V_L$ and $V_H$ framework residues were retained in the humanized 3D6 sequence to preserve the overall structure of the constant domain regions (CDRs) in the context of human kappa light chain and IgG1 heavy chain sequences. DNA sequences encoding the humanized 3D6 VL and VH sequences identified by this process (including the 5' signal peptide sequence and 3' intron splice-donor sequence) were generated by annealing synthesized overlapping DNA oligonucleotides followed by DNA polymerase fill-in reactions. The integrity of each of the humanized variable region sequences was verified by DNA sequencing. FIG. 1 depicts a schematic representation of the predicted structure of an exemplary humanized anti Aβ peptide 3D6 antibody termed h3D6v2. FIG. 2 identifies the complete amino acid sequences of the h3D6v2 light and heavy chains.

Humanized 3D6 antibody was expressed by transfection of a Chinese Hamster Ovary (CHO) host cell lineage with expression plasmids encoding anti Aβ antibody light chain and heavy chain genes. CHO cells expressing the antibody were isolated using standard methotrexate-based drug selection/gene amplification procedures. A clonal CHO cell line exhibiting the desired productivity and growth phenotypes was selected and used to establish an antibody expressing cell line using chemically defined medium free of animal or human-derived components.

Example II

Manufacturing Humanized Anti Aβ Antibody Drug Substance

The polypeptide manufacturing process began with the thawing of a starter culture of clonal cells stably expressing the anti-Aβ antibody. Cells were cultured using a chemically defined medium containing no animal or human-derived proteins. Cultures were then expanded and used to inoculate a seed bioreactor, which in turn was used to inoculate multiple production bioreactor cycles. The production bioreactor was operated in fed-batch mode. At the end of the production cycle, the conditioned medium harvest was clarified by microfiltration in preparation for further downstream processing.

The purification processes consisted of standard chromatographic steps followed by filtration. Purified antibody was concentrated by ultrafiltration and diafiltered into formulation buffer absent polysorbate-80. Optionally, polysorbate 80 (vegetable derived) is added to the ultrafiltration/diafiltration retentate pool, followed by bacterial retention filtration. The drug substance was stored frozen at −80° C. and held for further manufacture into drug product, including stabilized liquid formulations described herein.

Example III

Preparation of Antibody Formulation and Placebo

Two batches of antibody drug product were manufactured. An initial batch was manufactured by compounding drug substance into an animal and human protein-free formulation containing 20 mg anti Aβ antibody active substance per mL, 10 mM histidine, 10 mM methionine, 4% mannitol, 0.005% polysorbate-80, pH 6.0. The drug product was aseptically filled into vials, at 100 mg anti Aβ antibody active substance/ vial. The finished drug product vial contained no preservative and was intended for single-use only.

A second batch of drug product was manufactured by a similar method using a formulation buffer without polysorbate-80.

Example IV

Stability Analysis of Formulations with and without Polysorbate-80

The stability and, in particular, the physicochemical integrity (such as aggregation, deamidation, hydrolysis, and/or disulfide bond rearrangement) of the formulation were assessed by the following methods well known in the art: appearance; pH; protein concentration (A280); ELISA, in part, as a test of bioactivity; sodium dodecyl sulfate polyacrylamide gel electrophoresis (SDS-PAGE), in part as a test of aggregation; size exclusion high performance liquid chromatography (SEC-HPLC), in part, as a test of aggregation and stability in general; cation exchange high performance liquid chromatography (CEX-HPLC), in part, as a test of deamidation and stability in general; and peptide mapping. These methods assessed the recovery and integrity of the protein under test conditions at various temperatures.

Appearance analysis of the formulations was conducted in order to determine the quality of the formulations at various time points. Analysis was conducted based on visual inspection for clarity, color and the presence of particulates. For example, the degree of opalescence was analyzed in terms of reference suspensions. Appearance analysis of the formulations made with and without polysorbate 80 in accordance with the present invention demonstrated that both formulations were acceptable when stored at each of −80° C., 5° C., 25° C., and 40° C. at each of the following timepoints: initial, 1 month, 2 months, 3 months, 6 months, 9 months, and 12 months.

A pH analysis was carried out to determine the maintenance of the formulation's pH within an acceptable range of about 5.5 to about 6.5. pH analysis of formulations made with and without polysorbate 80 in accordance with the present invention demonstrated that both formulations were acceptable when stored at each of −80° C., 5° C., 25° C., and 40° C. at each of the following timepoints: initial, 1 month, 2 months, 3 months, 6 months, 9 months, and 12 months. Generally, the pH never ranged below 5.8 or above 6.2.

Protein concentration analysis by A280 assays was performed to determine the maintenance of the formulation's protein concentration within an acceptable range of about 17 mg/ml to about 23 mg/ml. Protein concentration analysis of formulations made with and without polysorbate 80 in accordance with the present invention demonstrated that both formulations were generally acceptable when stored at each of −80° C., 5° C., 25° C., and 40° C. at each of the following timepoints: initial, 1 month, 2 months, 3 months, 6 months, 9 months, and 12 months. With the exception of the protein concentrations ranging slightly above 23 mg/ml for the formulation without polysorbate 80 when stored at 5° C., 25° C., and 40° C. at the 3 month timepoints, the protein concentration otherwise remained within the acceptable ranges. Accordingly, the protein concentration analysis demonstrated no detectable loss of protein occurring, even at accelerated conditions, particularly for the formulations with polysorbate 80. Moreover, protein concentration generally failed to demonstrate a significant time or temperature dependent change subsequent to the initial time point.

Maintenance of biological activity was assayed, in part, by ELISA techniques. Biological activity was analysed as binding units (BU)/mg with acceptable activity being ≧2500 BU/mg or 50% (i.e., 5000 BU/mg equates to 100%). ELISA analysis of formulations made with and without polysorbate 80 in accordance with the present invention demonstrated that both formulations were generally acceptable when stored at each of −80° C., 5° C., 25° C., and 40° C. at each of the following timepoints: initial, 1 month, 2 months, 3 months, 6 months, 9 months, and 12 months. With the exception of the biological activity ranging slightly below 50% at the 12 month time point for both formulations when stored at 40° C., the biological activity otherwise remained within the acceptable ranges.

SEC-HPLC analysis was conducted as a test of aggregation, purity and stability in general. SEC-HPLC runs under conditions using mobile phase chromatography with a sodium phosphate dibasic buffer indicated the formulation was acceptable if the SEC-HPLC analysis identified≧90% IgG monomer, compared to percentage of high molecular weight product and low molecular weight product. SEC-HPLC analysis of formulations made with and without polysorbate 80 in accordance with the present invention demonstrated that both formulations were generally acceptable when stored at each of −80° C., 5° C., 25° C., and 40° C. at each of the following timepoints: initial, 1 month, 2 months, 3 months, 6 months, 9 months, and 12 months. With the exception of the percentage monomer ranging below 90% for both formulations when stored at 40° C. at each time point at and after 6 months (where the analysis identified greater than at least 10% low molecular weight product for both formulations at each time point), percentage monomer was otherwise within the acceptable range. SEC-HPLC analysis generally demonstrated that although the high molecular weight and low molecular weight profiles were different over time in samples with and without polysorbate, the monomeric form of the antibody generally remained constant, for example at the 12 month time point, when the formulation was stored at 5° C.

CEX-HPLC analysis was conducted as a test of amination and stability in general. CEX-HPLC runs under conditions using mobile phase chromatography with a NaCl buffer produced elution profile and retention times of predominant peaks which were analyzed as being comparable or not comparable to reference standard profiles. CEX-HPLC analysis of formulations made with and without polysorbate 80 in accordance with the present invention demonstrated that both formulations were generally acceptable when stored at each of −80° C., 5° C., 25° C., and 40° C. at each of the following timepoints: initial, 1 month, 2 months, 3 months, 6 months, 9 months, and 12 months. With the exception of the elution profile and retention time of the predominant peaks not being comparable for both formulations when stored at 40° C. at each time point at and after 3 months, the predominant peaks were otherwise comparable to the reference peaks.

Figure 6:
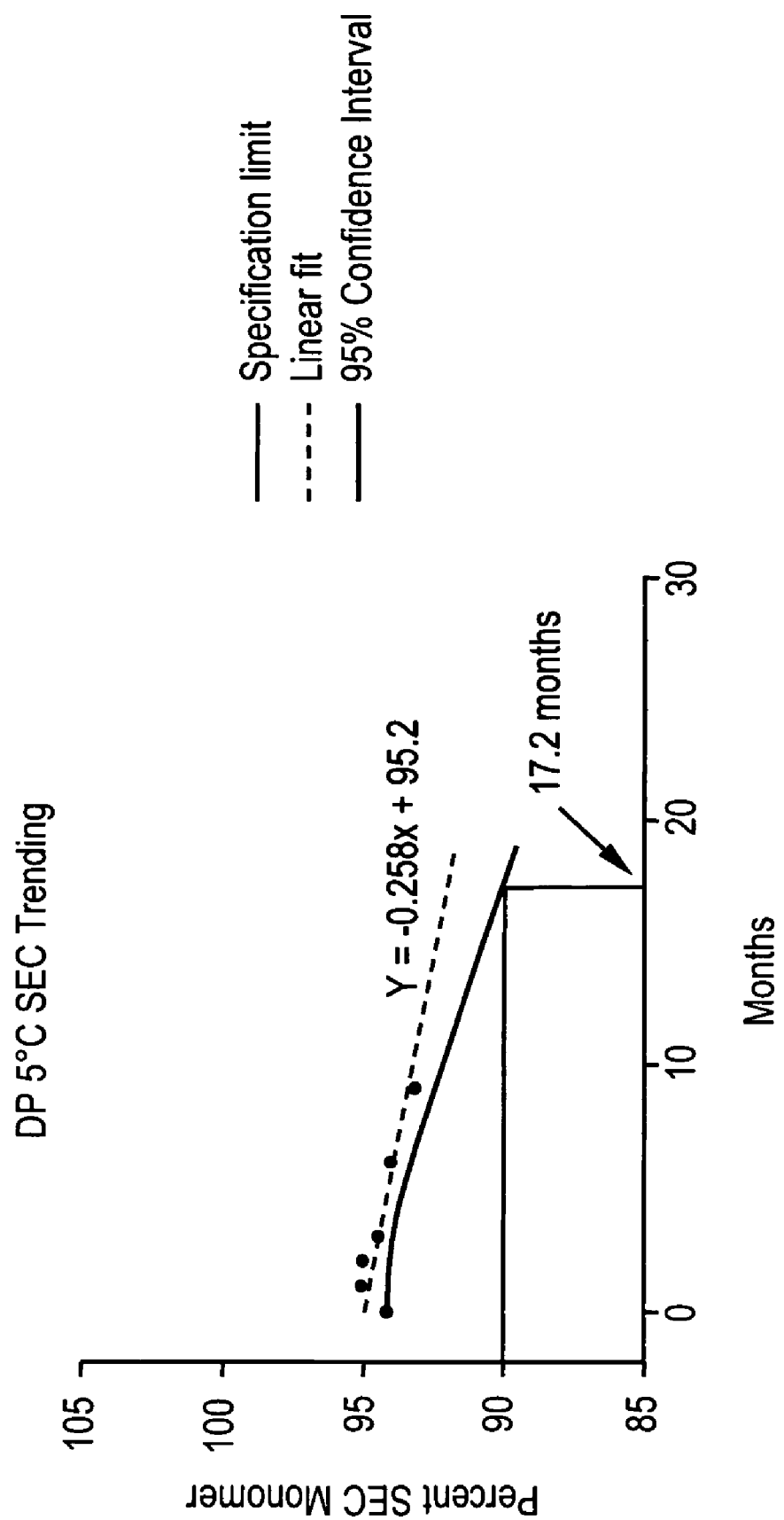
FIG. 6 graphically depicts the degradation predictions of formulations with PS80 made in accordance with the present invention and stored at 5° C.
Figure 7B:
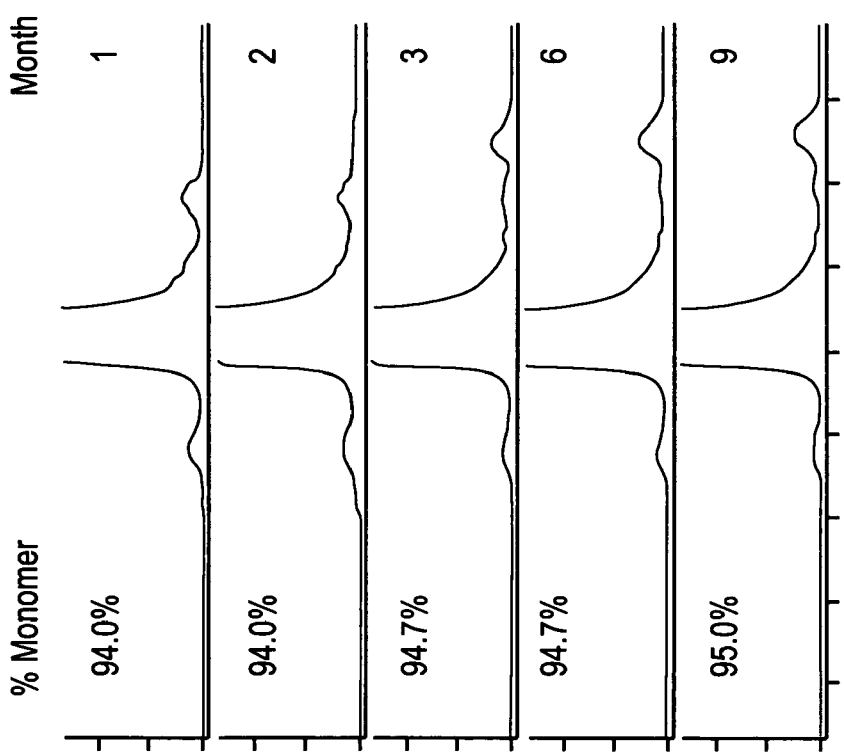
FIG. 7 graphically depicts the size exclusion chromatography (SEC) analysis of formulations with PS80 made in accordance with the present invention, stored at 5° C., and reprocessed to minimize assay variability.
Figure 7A:
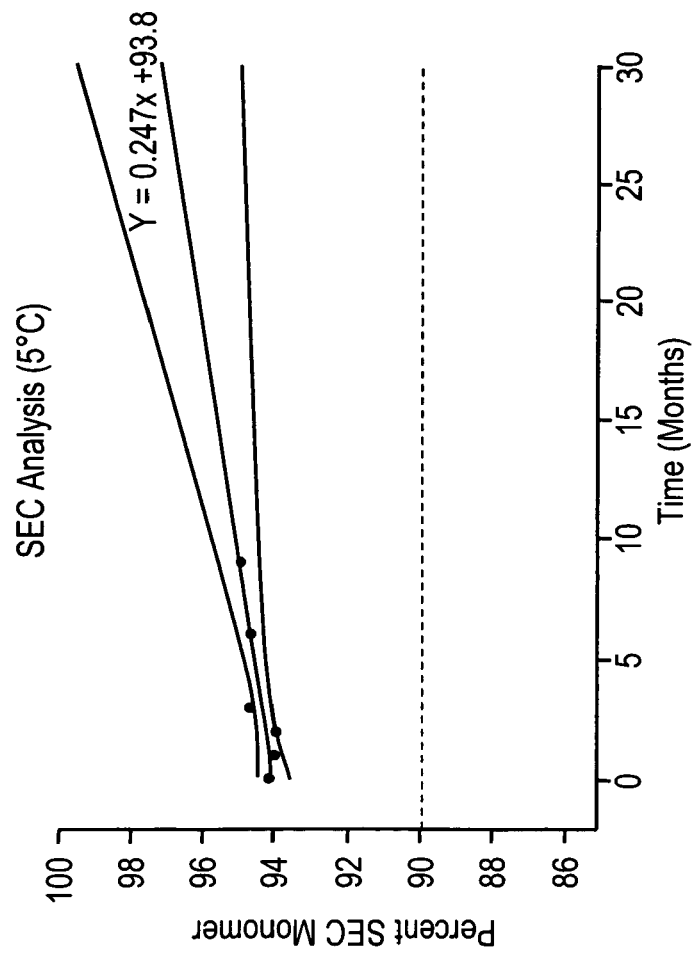
Figure 9:
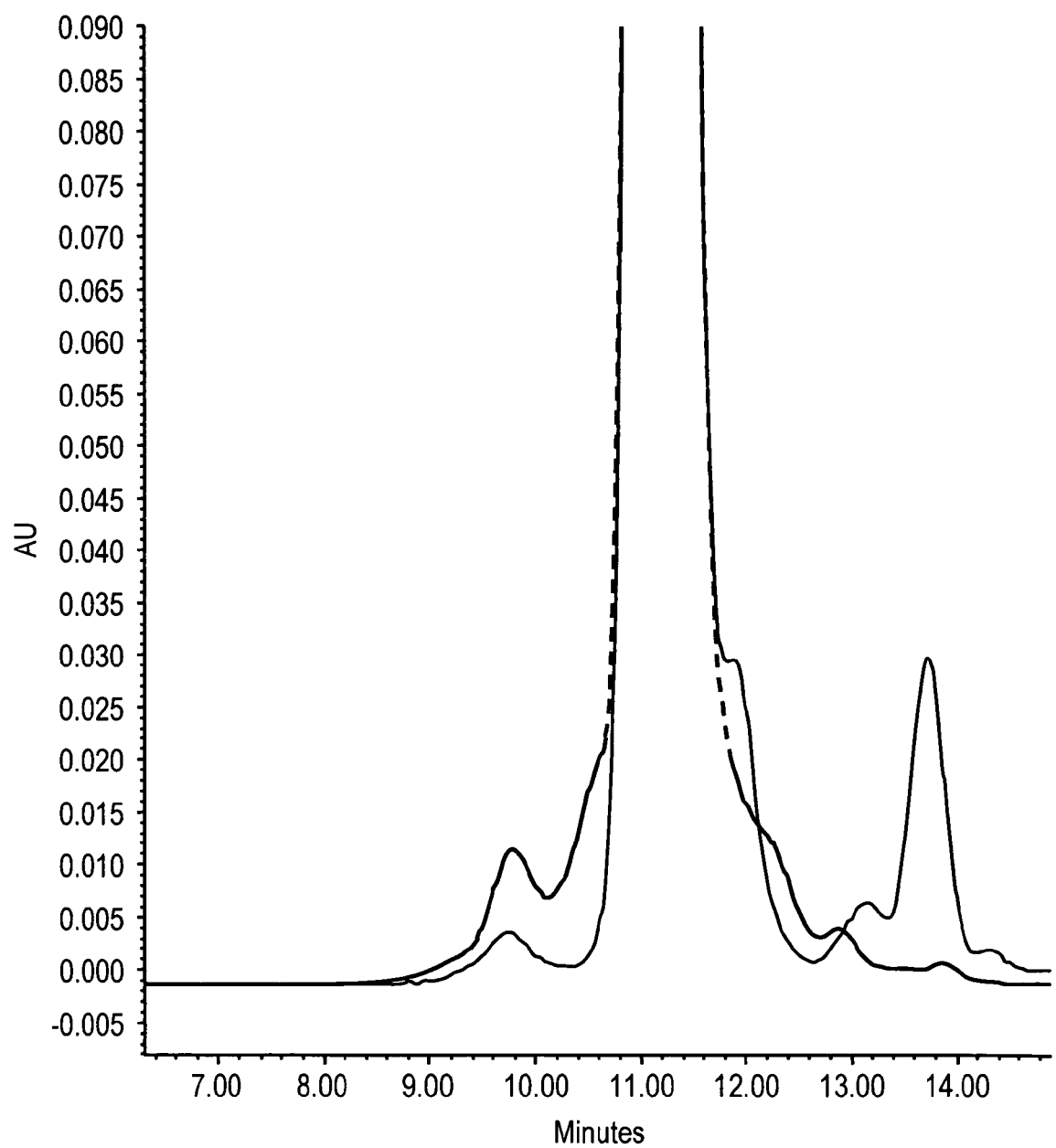
FIG. 9 depicts a chromatogram which indicates that the presence of PS80 shifts the by-products found within the stabilized polypeptide formulation from a high molecular weight species to a low molecular weight species without changing the monomer antibody profile.

Generally, analysis of the formulations with polysorbate 80 stored at 5° C. allow for the following particularly important conclusions: 1) opalescence, pH, ELISA, CEX-HPLC, SEC-HPLC and SDS PAGE analysis all showed minimal changes in the formulation over 9 months; 2) formulations stored at 5° C. appeared more like reference samples over 9 months than the accelerated samples; 3) peptide mapping showed changes at 5° C.; and 4) SEC-HPLC trending data at 5° C. predicted at least 17.2 months of stability (see FIG. 6), however, upon removing column, instrument and buffer variability, the data allowed for a prediction of greater than 30 months of stability (see FIG. 7). Additionally, accelerated samples with polysorbate 80 stored at 25° C. passed all specifications at 9 months (FIG. 4).

Moreover, analysis of the formulations without polysorbate 80 stored at 5° C. allow for the following particularly important conclusions: 1) opalescence, pH and ELISA analysis all showed minimal changes in the formulation over 9 months; 2) results of the CEX-HPLC and SDS PAGE showed comparable findings to reference samples or the −80° C. control at 9 months; 3) SEC-HPLC analysis showed minor changes over 9 months while changes were more pronounced at accelerated temperatures; and 4) SEC-HPLC trending data predicted at least 18 months of stability, even with assay variability issues (see FIG. 8).

Figure 3A:
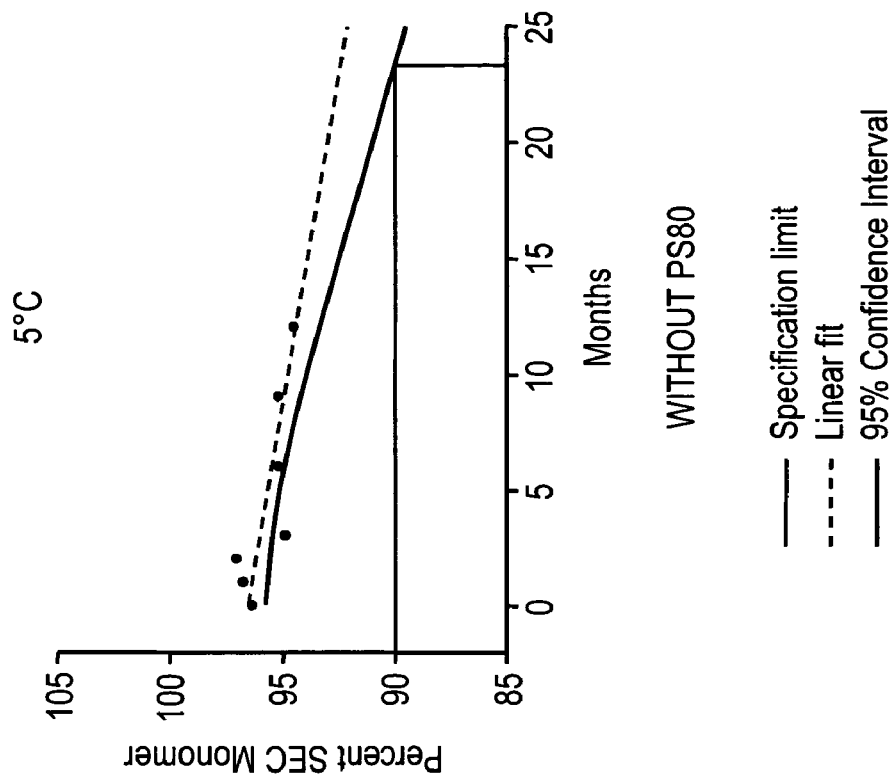
FIG. 3 graphically depicts the shelf life predictions for antibody formulations (with and without polysorbate 80 (PS80)) made in accordance with the present invention and stored at 5° C.
Figure 3B:
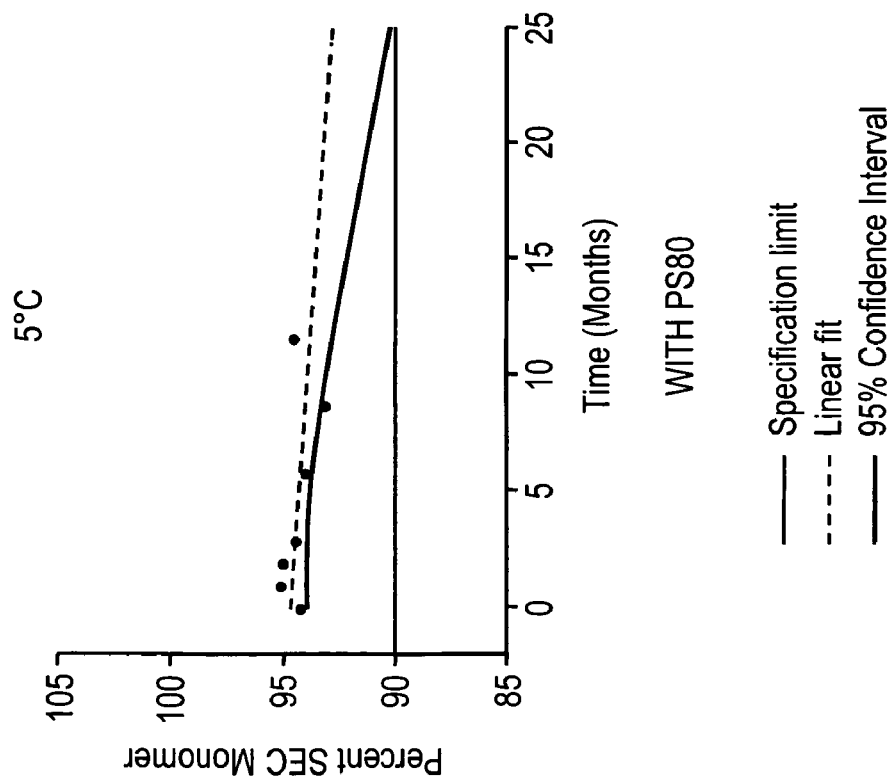
Figure 4A:
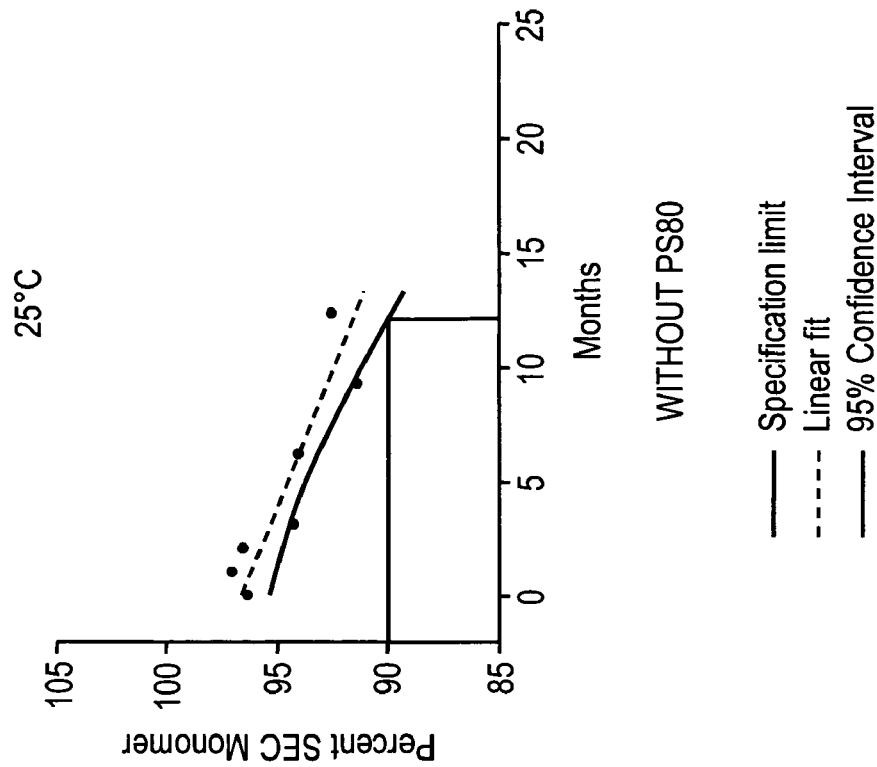
FIG. 4 graphically depicts the shelf life predictions for antibody formulations (with and without PS80) made in accordance with the present invention and stored at 25° C.
Figure 4B:
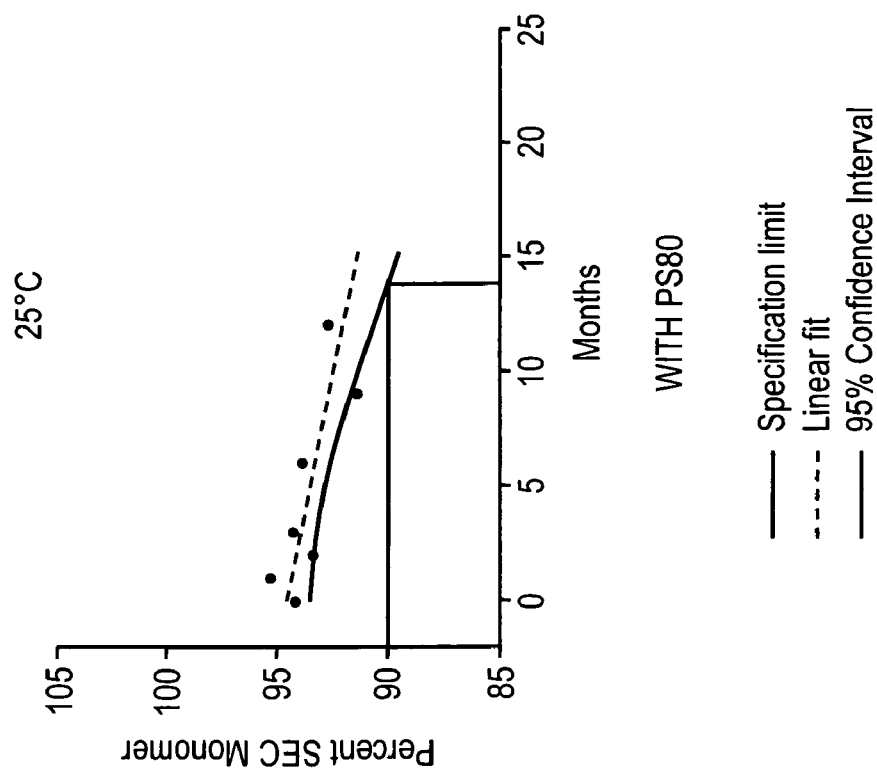
Figure 5A:
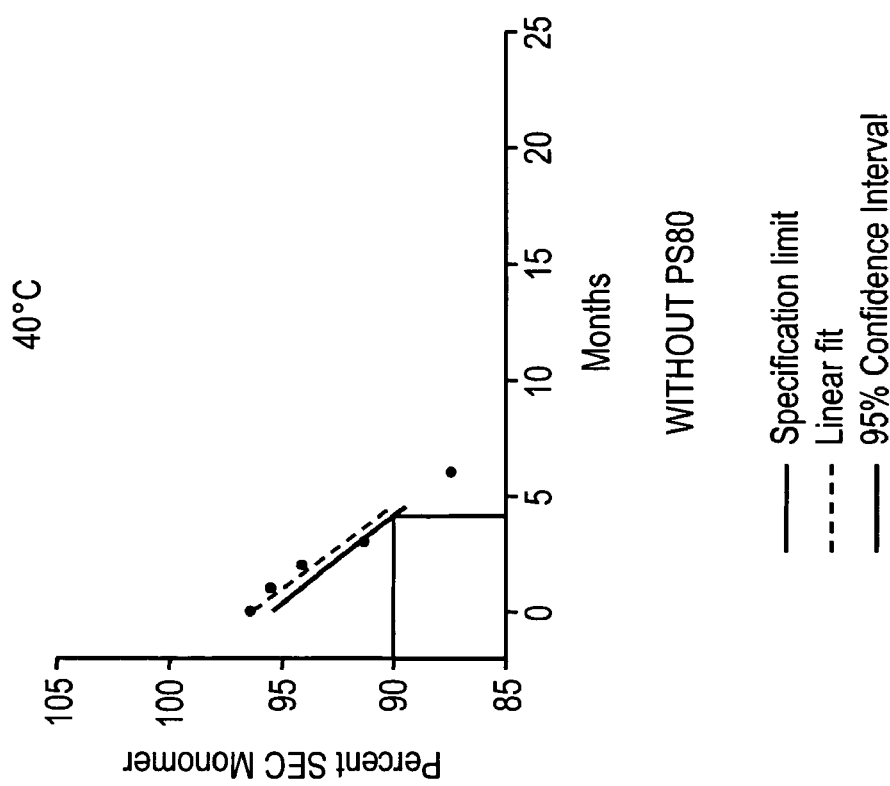
FIG. 5 graphically depicts the shelf life predictions for antibody formulations (with and without PS80) made in accordance with the present invention and stored at 40° C.
Figure 5B:
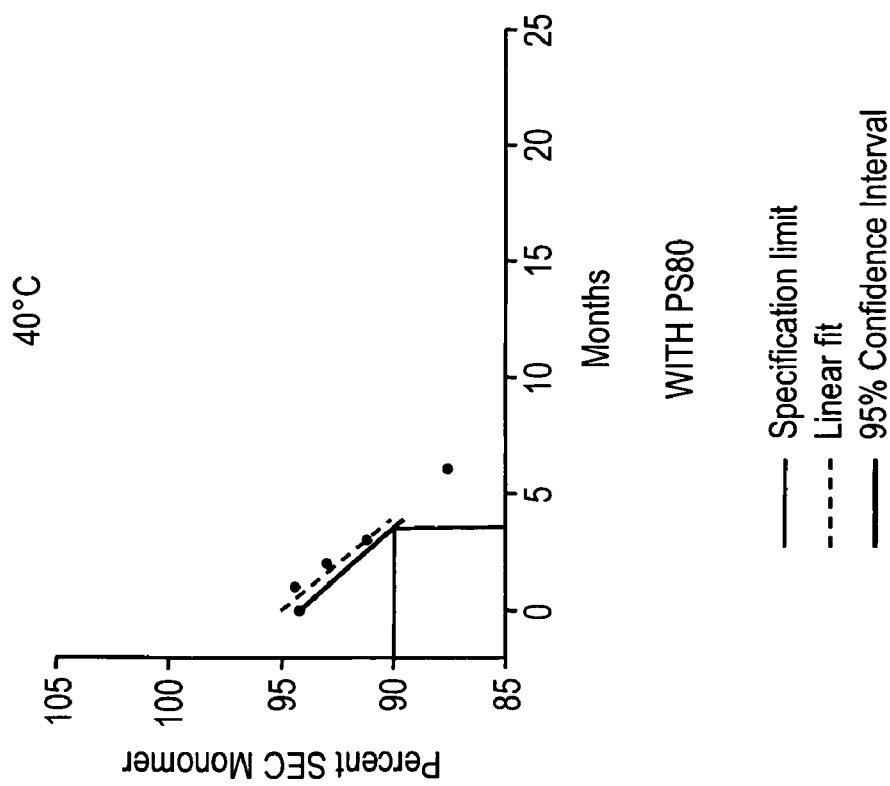

FIGS. 3-5 are graphical depictions of the shelf life predictions for the formulations (with and without PS80) made in accordance with the present invention and stored at 5° C., 25° C., and 40° C., respectively. Generally, FIGS. 3-5 indicate that storage of the formulations of the present invention at higher temperatures reduces the expected shelf life. FIG. 3, in particular, indicates that the formulation has an expected shelf life of at least 18 months when the formulation is stored at 5° C. FIG. 4 indicates that storage of the formulation at room temperature (25° C.) may serve to reduce expected shelf life to about 12 months. FIG. 5 further demonstrates that storage of the formulation at 40° C. may serve to reduce expected shelf life to about 4 months.

Example V

Stability Studies on use of Methionine as an Anti-Oxidant

Figure 10:
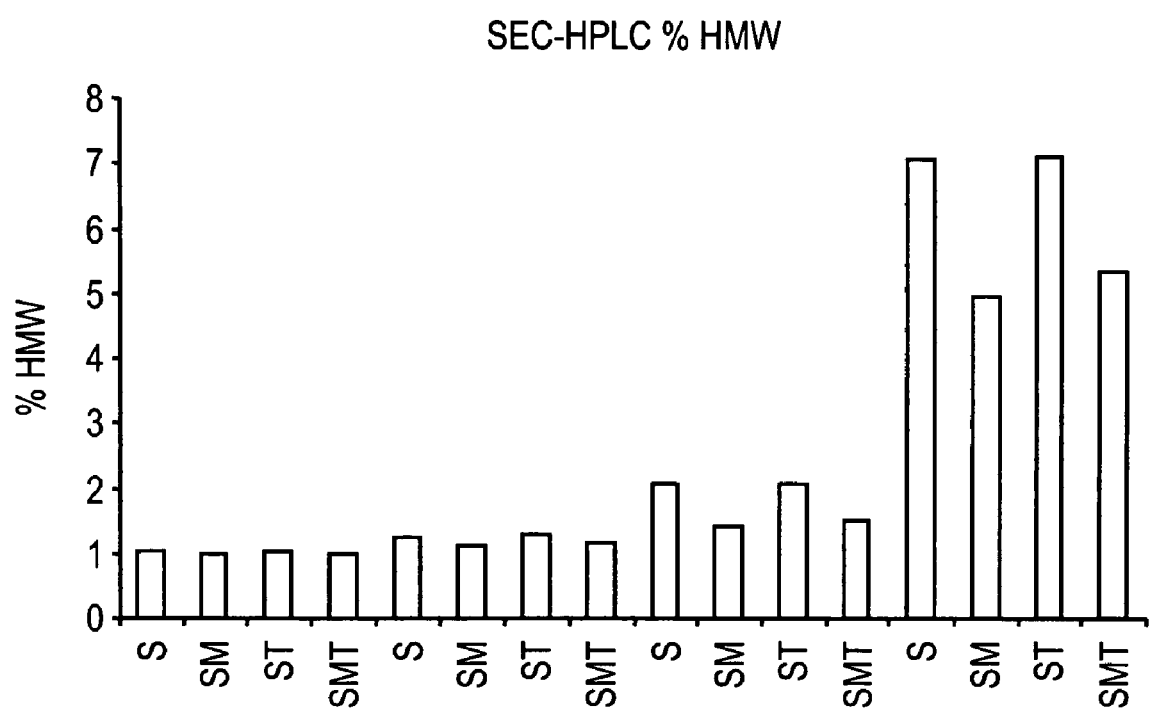
FIG. 10 graphically depicts the inhibition of the formation of undesired by-products in a polypeptide formulation comprising IgG4, in particular, high molecular weight polypeptide aggregates, upon the addition of an antioxidant such as free methionine.

Studies were conducted to determine the effect of methionine on maintaining the stability of the antibody in antibody formulations. SEC-HPLC analysis was conducted over 6 months at various temperatures on four antibody samples (using an anti-CD22 IgG$_4$ antibody): an antibody formulation with 20 mM succinate at a pH of 6.0; an antibody formulation with 20 mM succinate and 10 mM methionine; an antibody formulation with 20 mM succinate and 0.01% PS80; and an antibody formulation with 20 mM succinate, 10 mM methionine and 0.01% PS80. Generally, the results indicated that methionine desirably lessens high molecular weight (HMW) formation. Moreover, methionine decreases temperature dependent increase in the percent of HMW (See FIG. 10).

Figure 11A:
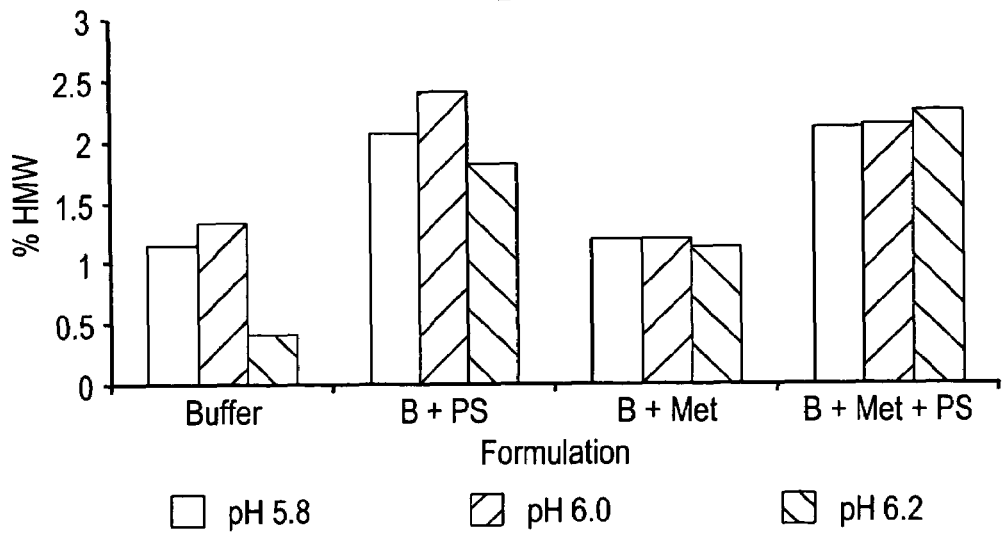
FIG. 11 graphically depicts the inhibition of the formation of undesired by-products in a polypeptide formulation comprising IgG2, in particular, high molecular weight polypeptide aggregates, upon the addition of an antioxidant such as free methionine.
Figure 11B:
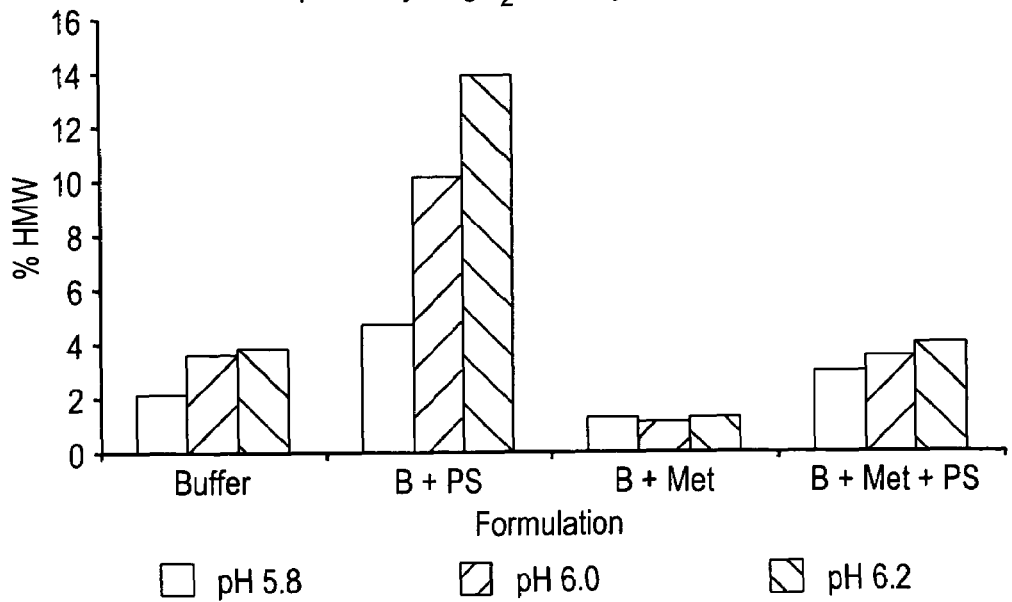

Furthermore, a pH stability study (at pH 5.8, 6.0 and 6.2) was conducted over 6 weeks at various temperatures (5° C. and 40° C.) on the following four antibody (an anti-B7.2 IgG$_2$ antibody) samples: (1) a sample including antibody, 10 mM histidine and 150 mM NaCl; (2) a sample including antibody, 10 mM histidine, 150 mM NaCl and 0.01% PS80; (3) a sample including antibody, 10 mM histidine, 150 mM NaCl and 10 mM methionine; and (4) a sample including antibody, 10 mM histidine, 150 mM NaCl, 10 mM methionine and 0.01% PS80. SEC-HPLC analysis was conducted. The results demonstrated that methionine decreases the temperature dependent increase in percent of by-product formation (for example, HMW by-products) over the indicated pH range, for example, from about pH 5.8 to about pH 6.2 (see FIG. 11). As shown in FIG. 11, samples containing methionine displayed a low amount of aggregation when maintained at 40° C. for six weeks, which was similar to that for samples maintained at 5° C. for six weeks.

Example VI

Excipient Analysis of an IgG1 Antibody by Differential Scanning Calorimetry

A primary goal of protein drug formulation is to stabilize a protein in its native, biologically active form. Typically this can be done by screening various excipients in a base formulation and monitoring their effect on the molecule's molecular weight and activity. These parameters are indicative of stability. Another measurement of stability is thermal denaturation which can be monitored using a variety of biophysical techniques. Generally, increased levels of protein stability have been attributed to high melting, denaturation or decomposition temperatures. Accordingly, thermal properties of a representative IgG1 monoclonal antibody were monitored in the presence of various excipients using a VP-Capillary Differential Scanning Calorimeter. Specifically, the apparent $T_m$s were determined for formulations containing 10 mM histidine (pH 6.0) with various excipients. Several excipients were shown to provide increased or decreased thermal stability. Because increased levels of protein stability have been attributed to a high melting temperature, excipients in samples imparting an increased $T_m2$ or $T_m3$, as compared to control $T_m2/T_m3$ values (respectively, 74.9° C. and 83.4° C.), were deemed to be especially desirable excipients (see Table 1 below).

Accordingly, it was concluded that excipients such as glucose (formulated at a concentration of 4% and 10%), sucrose (formulated at a concentration of 4% and 10%), sorbitol (formulated at a concentration of 4% and 10%), and mannitol (formulated at a concentration of 4% and 10%), performed especially well in stabilizing a liquid polypeptide formulation, in particular, an antibody IgG formulation.

TABLE 1

Excipient Analysis Results

| Excipient | Concentration | $T_m1$* | $T_m2$* | $T_m3$* |
|---|---|---|---|---|
| Histidine (Control) | 10 mM | — | 74.9 | 83.4 |
| NaCl | 10 mM | 69.3 | 74.8 | 82.9 |
|  | 100 mM | 67.9 | 74.4 | 82.4 |
|  | 500 mM | 66.5 | 74.5 | 81.9 |
|  | 1 M | 65.4 | 74.9 | 82.3 |
| CaCl2 | 10 mM | 68.7 | 74.6 | 82.7 |
|  | 100 mM | 68.5 | 74.5 | 82.4 |
| Methionine | 30 mM | — | 74.5 | 83.7 |
| Vitamin C | ~30 mM | 52.2 | 68.7 | — |
| Polysorbate 20 | 0.005% | — | 74.5 | 83.7 |
|  | 0.01% | — | 74.5 | 83.8 |
|  | 0.1% | — | 74.4 | 83.7 |
| Polysorbate 80 | 0.005% | — | 74.6 | 83.8 |
|  | 0.01% | — | 74.5 | 83.7 |
|  | 0.1% | — | 74.5 | 83.7 |
| Glucose | 0.5% | — | 74.7 | 83.8 |
|  | 2% | — | 74.9 | 83.9 |
|  | 4% | — | 75.0 | 84.3 |
|  | 10% | — | 75.8 | 84.9 |
| Sucrose | 0.5% | — | 74.6 | 83.6 |
|  | 2% | — | 74.8 | 83.8 |
|  | 4% | — | 75.0 | 83.9 |
|  | 10% | — | 75.5 | 84.4 |
| Sorbitol | 0.5% | — | 74.8 | 83.6 |
|  | 2% | — | 75.0 | 83.8 |
|  | 4% | — | 75.2 | 84.1 |
|  | 10% | — | 75.9 | 84.8 |
| Mannitol | 0.5% | — | 74.8 | 83.6 |
|  | 2% | — | 74.9 | 83.8 |
|  | 4% | — | 75.2 | 84.1 |
|  | 10% | — | 75.9 | 84.8 |

*In the control (10 mM histidine, pH 6.0) two transitions were observed, $T_m2$ and $T_m3$. An earlier transition ($T_m1$) was seen in the presence of some excipients.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A stable formulation, comprising:
   (a) a humanized version of monoclonal antibody 3D6 at a concentration of from about 1 mg/ml, to about 50 mg/ml, wherein the humanized 3D6 antibody comprises a light chain comprising the amino acid sequence of SEQ ID NO:1 and a heavy chain comprising the amino acid sequence of residues 1-448 of SEQ ID NO:2;
   (b) histidine at a concentration of from about 5 mM to about 15 mM;
   (c) mannitol in an amount of from about 2% w/v to about 6% w/v;
   (d) methionine at a concentration of from about 5 mM to about 15 mM; and
   (e) polysorbate in an amount of from about 0.001% w/v to about 0.01% w/v, wherein the formulation has a pH of from about 5.5 to about 6.5.

2. The formulation of claim 1, wherein the antibody is present at a concentration of from about 17 mg/ml to about 23 mg/ml.

3. The formulation of claim 2, wherein the histidine is present at a concentration of from 8 mM to 12 mM.

4. The formulation of claim 3, wherein the mannitol is present in an amount of from 3% w/v to 5% w/v.

5. The formulation of claim 4, wherein the methionine is present at a concentration of from 8 mM to 12 mM.

6. The formulation of claim 5, wherein the polysorbate is present in an amount of from 0.003% w/v to 0.007% w/v.

7. The formulation of claim 6, wherein the pH is from 5.8 to 6.2.

8. A stable unit dosage form, comprising:
   (a) a humanized version of monoclonal antibody 3D6 in an amount of from about 10 mg to about 250 mg, wherein the humanized 3D6 antibody comprises a light chain comprising the amino acid sequence of SEQ ID NO:1 and a heavy chain comprising the amino acid sequence of residues 1-448 of SEQ ID NO:2;
   (b) histidine at a concentration of from about 5 mM to about 15 mM;
   (c) mannitol in an amount of from about 2% w/v to about 6% w/v;

(d) methionine at a concentration of from about 5 mM to about 15 mM; and
(e) polysorbate in an amount of from about 0.001% w/v to about 0.01% w/v, wherein the formulation has a pH of from about 5.5 to about 6.5.

9. The unit dosage form of claim 8, wherein the antibody is present in an amount of from 80 mg to 120 mg.

10. The unit dosage form of claim 9, wherein the histidine is present at a concentration of from 8 mM to 12 mM.

11. The unit dosage form of claim 10, wherein the mannitol is present in an amount of from 3% w/v to 5% w/v.

12. The unit dosage form of claim 11, wherein the methionine is present at a concentration of from 8 mM to 12 mM.

13. The unit dosage form of claim 12, wherein the polysorbate is present in an amount of from 0.003% w/v to 0.007% w/v.

14. The unit dosage form of claim 13, wherein the pH is from 5.8 to 6.2.

15. The unit dosage form of claim 8, wherein the 3D6 antibody is present at a concentration of from 17 mg/ml to about 23 mg/ml.

16. A pharmaceutical product, comprising:
(i) a glass vial comprising a stable humanized 3D6 antibody formulation, the formulation comprising:
(a) a humanized version of monoclonal antibody 3D6 in an amount of from about 10 mg to about 250 mg, wherein the humanized 3D6 antibody comprises a light chain comprising the amino acid sequence of SEQ ID NO: 1 and a heavy chain comprising the amino acid sequence of residues 1-448 of SEQ ID NO:2;
(b) histidine at a concentration of from about 5 mM to about 15 mM;
(c) mannitol in an amount of from about 2% w/v to about 6% w/v;
(d) methionine at a concentration of from about 5 mM to about 15 mM; and
(e) polysorbate in an amount of from about 0.001% w/v to about 0.01% w/v, wherein the formulation has a pH of from about 5.5 to about 6.5; and
(ii) labeling for use comprising instructions to use the appropriate volume of the antibody formulation necessary to achieve a dose of from about 0.15 mg to about 5 mg per kg of patient body weight.

17. The pharmaceutical product of claim 16, wherein the antibody is present in an amount of from 80 mg to 120 mg.

18. The pharmaceutical product of claim 17, wherein the histidine is present at a concentration of from 8 mM to 12 mM.

19. The pharmaceutical product of claim 18, wherein the mannitol is present in an amount of from 3% w/v to 5% w/v.

20. The pharmaceutical product of claim 19, wherein the methionine is present at a concentration of from 8 mM to 12 mM.

21. The pharmaceutical product of claim 20, wherein the polysorbate is present in an amount of from 0.003% w/v to 0.007% w/v.

22. The pharmaceutical product of claim 21, wherein the pH is from 5.8 to 6.2.

23. The pharmaceutical product of claim 22, wherein the dose is from about 0.5 mg to about 3 mg per kg of patient body weight.

24. The pharmaceutical product of claim 23, wherein the dose is from about 1 mg to about 2 mg per kg of patient body weight.

25. The pharmaceutical product of claim 16, wherein the 3D6 antibody is present at a concentration of from about 17 mg/ml to about 23 mg/ml.

26. A stable formulation, comprising:
(a) a humanized version of monoclonal antibody 3D6 at a concentration of about 20 mg/ml, wherein the humanized 3D6 antibody comprises a light chain comprising the amino acid sequence of SEQ ID NO:1 and a heavy chain comprising the amino acid sequence of residues 1-448 of SEQ ID NO:2;
(b) L-histidine at a concentration of about 10 mM;
(c) D-mannitol in an amount of about 4% w/v;
(d) methionine at a concentration of about 10 mM; and
(e) polysorbate-80 in an amount of about 0.005% w/v, wherein the formulation has a pH of about 6.0.

27. A stable unit dosage form, comprising:
(a) a humanized version of monoclonal antibody 3D6 in an amount of about 100 mg, wherein the humanized 3D6 antibody comprises a light chain comprising the amino acid sequence of SEQ ID NO:1 and a heavy chain comprising the amino acid sequence of residues 1-448 of SEQ ID NO:2;
(b) L-histidine at a concentration of about 10 mM;
(c) D-mannitol in an amount of about 4% w/v;
(d) methionine at a concentration of about 10 mM; and
(e) polysorbate-80 in an amount of about 0.005% w/v, wherein the formulation has a pH of about 6.0.

28. A pharmaceutical product, comprising:
(i) a glass vial comprising a stable humanized 3D6 antibody formulation, the formulation comprising:
(a) a humanized version of monoclonal antibody 3D6 in an amount of about 100 mg, wherein the humanized 3D6 antibody comprises a light chain comprising the amino acid sequence of SEQ ID NO:1 and a heavy chain comprising the amino acid sequence of residues 1-448 of SEQ ID NO:2;
(b) L-histidine at a concentration of about 10 mM;
(c) D-mannitol in an amount of about 4% w/v;
(d) methionine at a concentration of about 10 mM; and
(e) polysorbate-80 in an amount of about 0.005% w/v, wherein the formulation has a pH of from about 5.5 to about 6.5;and
(ii) labeling for use comprising instructions to use the appropriate volume of the antibody formulation necessary to achieve a dose of from about 0.5 mg to about 3 mg per kg of patient body weight.

* * * * *

UNITED STATES PATENT AND TRADEMARK OFFICE
CERTIFICATE OF CORRECTION

PATENT NO. : 7,635,473 B2
APPLICATION NO. : 11/342353
DATED : December 22, 2009
INVENTOR(S) : Warne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 522 days.

Signed and Sealed this

Ninth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,635,473 B2 | |
| APPLICATION NO. | : 11/342353 | |
| DATED | : December 22, 2009 | |
| INVENTOR(S) | : Nicholas W. Warne, Donna Luisi and Angela Kantor | |

It is certified that error appears in the above-identified patent and that said Letters Patent is hereby corrected as shown below:

On the title page, item (73) Assignees, insert --LLC-- after "Wyeth"

Claim 8, Column 97, Line 4, delete "formulation" and insert --unit dosage form--

Claim 27, Column 98, Line 35, delete "formulation" and insert --unit dosage form--

Signed and Sealed this
Fifteenth Day of March, 2011

David J. Kappos
*Director of the United States Patent and Trademark Office*

SEQUENCE LISTING

<160> NUMBER OF SEQ ID NOS: 47

<210> SEQ ID NO 1
<211> LENGTH: 219

<212> TYPE: PRT
<213> ORGANISM: Artificial Sequence
<220> FEATURE:
<223> OTHER INFORMATION: Description of Artificial Sequence: Synthetic construct

<400> SEQUENCE: 1

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 2
<211> LENGTH: 449
<212> TYPE: PRT
<213> ORGANISM: Artificial Sequence
<220> FEATURE:
<223> OTHER INFORMATION: Description of Artificial Sequence: Synthetic construct

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (1)
```

```
<223> OTHER INFORMATION: Asp or Tyr
<220> FEATURE:
<221> NAME/KEY: MOD_RES
<222> LOCATION: (7)
<223> OTHER INFORMATION: Ser or Thr
<220> FEATURE:
<221> NAME/KEY: MOD_RES
<222> LOCATION: (10)
<223> OTHER INFORMATION: Ser or Thr
<220> FEATURE:
<221> NAME/KEY: MOD_RES
<222> LOCATION: (15)
<223> OTHER INFORMATION: Leu, Ile, or Val
<220> FEATURE:
<221> NAME/KEY: MOD_RES
<222> LOCATION: (50)
<223> OTHER INFORMATION: Arg or Lys
<220> FEATURE:
<221> NAME/KEY: MOD_RES
<222> LOCATION: (88)
<223> OTHER INFORMATION: Val or Leu
<220> FEATURE:
<221> NAME/KEY: MOD_RES
<222> LOCATION: (109)
<223> OTHER INFORMATION: Val or Leu

<400> SEQUENCE: 3

Xaa Val Val Met Thr Gln Xaa Pro Leu Xaa Leu Pro Val Thr Xaa Gly
 1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Xaa Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Trp Gln Gly
                85                  90                  95

Thr His Phe Pro Arg Thr Phe Gly Gly Gly Thr Lys Xaa Glu Ile Lys
            100                 105                 110

Arg

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (3)
<223> OTHER INFORMATION: Gln, Lys, or Arg
<220> FEATURE:
<221> NAME/KEY: MOD_RES
<222> LOCATION: (78)
<223> OTHER INFORMATION: Ser or Thr
<220> FEATURE:
<221> NAME/KEY: MOD_RES
<222> LOCATION: (87)
<223> OTHER INFORMATION: Arg or Lys
<220> FEATURE:
<221> NAME/KEY: MOD_RES
<222> LOCATION: (88)
<223> OTHER INFORMATION: Ala, Ser, or Thr
<220> FEATURE:
<221> NAME/KEY: MOD_RES
<222> LOCATION: (114)
<223> OTHER INFORMATION: Leu, Thr, Ile, or Val
```

```
<400> SEQUENCE: 4

Glu Val Xaa Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Xaa Leu Tyr
65                  70                  75                  80

Leu Gln Met Asn Ser Leu Xaa Xaa Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Xaa Val Thr Val Ser Ser
        115

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 5

Asp Val Val Met Thr Gln Ser Pro Leu Ser Leu Pro Val Thr Leu Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gln Gly Thr Lys Val Glu Ile Lys
            100                 105                 110

Arg

<210> SEQ ID NO 6
<211> LENGTH: 119
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
```

```
                35                  40                  45
Ala Ser Ile Arg Ser Gly Gly Arg Thr Tyr Tyr Ser Asp Asn Val
 50                  55                  60

Lys Gly Arg Phe Thr Ile Ser Arg Glu Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Arg Tyr Asp His Tyr Ser Gly Ser Ser Asp Tyr Trp Gly Gln Gly
                100                 105                 110

Thr Leu Val Thr Val Ser Ser
            115

<210> SEQ ID NO 7
<211> LENGTH: 219
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 7

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Gln Gln Arg Pro Gly Gln Ser
         35                  40                  45

Pro Arg Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Gln Ala Glu Asp Val Gly Val Tyr Tyr Cys Trp Gln Gly
                 85                  90                  95

Thr His Phe Pro Arg Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 8
<211> LENGTH: 449
<212> TYPE: PRT
<213> ORGANISM: Artificial Sequence
<220> FEATURE:
<223> OTHER INFORMATION: Description of Artificial Sequence: Synthetic
      humanized antibody
```

<400> SEQUENCE: 8

Glu Val Gln Leu Val Glu Ser Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

-continued

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 9
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (3)
<223> OTHER INFORMATION: Val or Leu
<220> FEATURE:
<221> NAME/KEY: MOD_RES
<222> LOCATION: (7)
<223> OTHER INFORMATION: Ser or Thr
<220> FEATURE:
<221> NAME/KEY: MOD_RES
<222> LOCATION: (14)
<223> OTHER INFORMATION: Thr or Ser
<220> FEATURE:
<221> NAME/KEY: MOD_RES
<222> LOCATION: (17)
<223> OTHER INFORMATION: Gln, Asp, or Asn
<220> FEATURE:
<221> NAME/KEY: MOD_RES
<222> LOCATION: (30)
<223> OTHER INFORMATION: Ile or Val
<220> FEATURE:
<221> NAME/KEY: MOD_RES
<222> LOCATION: (50)
<223> OTHER INFORMATION: Arg or Lys
<220> FEATURE:
<221> NAME/KEY: MOD_RES
<222> LOCATION: (88)
<223> OTHER INFORMATION: Val or Leu
<220> FEATURE:
<221> NAME/KEY: MOD_RES
<222> LOCATION: (105)
<223> OTHER INFORMATION: Gly or Ala
<220> FEATURE:
<221> NAME/KEY: MOD_RES
<222> LOCATION: (109)
<223> OTHER INFORMATION: Val or Leu

<400> SEQUENCE: 9

Asp Val Xaa Met Thr Gln Xaa Pro Leu Ser Leu Pro Val Xaa Leu Gly
1               5                   10                  15

Xaa Pro Ala Ser Ile Ser Cys Arg Ser Ser Gln Asn Ile Xaa His Ser
            20                  25                  30

Asn Gly Asn Thr Tyr Leu Glu Trp Tyr Leu Gln Lys Pro Gly Gln Ser
        35                  40                  45

Pro Xaa Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Phe Gln Gly
                85                  90                  95

Ser His Val Pro Leu Thr Phe Gly Xaa Gly Thr Lys Xaa Glu Ile Lys
            100                 105                 110

Arg

```
<210> SEQ ID NO 10
<211> LENGTH: 123
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (1)
<223> OTHER INFORMATION: Gln or Glu
<220> FEATURE:
<221> NAME/KEY: MOD_RES
<222> LOCATION: (2)
<223> OTHER INFORMATION: Val or Ala
<220> FEATURE:
<221> NAME/KEY: MOD_RES
<222> LOCATION: (64)
<223> OTHER INFORMATION: Ser or Thr
<220> FEATURE:
<221> NAME/KEY: MOD_RES
<222> LOCATION: (77)
<223> OTHER INFORMATION: Lys or Arg
<220> FEATURE:
<221> NAME/KEY: MOD_RES
<222> LOCATION: (78)
<223> OTHER INFORMATION: Ser or Thr
<220> FEATURE:
<221> NAME/KEY: MOD_RES
<222> LOCATION: (83)
<223> OTHER INFORMATION: Thr or Ser
<220> FEATURE:
<221> NAME/KEY: MOD_RES
<222> LOCATION: (84)
<223> OTHER INFORMATION: Met, Ile, or Leu
<220> FEATURE:
<221> NAME/KEY: MOD_RES
<222> LOCATION: (86)
<223> OTHER INFORMATION: Asn, Ser, or Thr
<220> FEATURE:
<221> NAME/KEY: MOD_RES
<222> LOCATION: (87)
<223> OTHER INFORMATION: Met, Val, or Leu
<220> FEATURE:
<221> NAME/KEY: MOD_RES
<222> LOCATION: (118)
<223> OTHER INFORMATION: Leu or Ser

<400> SEQUENCE: 10

Xaa Xaa Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Xaa
    50                  55                  60

Leu Lys Ser Arg Leu Thr Ile Ser Lys Asp Thr Ser Xaa Xaa Gln Val
65                  70                  75                  80

Val Leu Xaa Xaa Thr Xaa Xaa Asp Pro Val Asp Thr Ala Thr Tyr Tyr
                85                  90                  95

Cys Val Arg Arg Pro Ile Thr Pro Val Leu Val Asp Ala Met Asp Tyr
            100                 105                 110

Trp Gly Gln Gly Thr Xaa Val Thr Val Ser Ser
        115                 120

<210> SEQ ID NO 11
<211> LENGTH: 113
<212> TYPE: PRT
```

<213> ORGANISM: Artificial Sequence
<220> FEATURE:
<223> OTHER INFORMATION: Description of Artificial Sequence: Synthetic humanized antibody

<400> SEQUENCE: 11

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg

<210> SEQ ID NO 12
<211> LENGTH: 123
<212> TYPE: PRT
<213> ORGANISM: Artificial Sequence
<220> FEATURE:
<223> OTHER INFORMATION: Description of Artificial Sequence: Synthetic humanized antibody

<400> SEQUENCE: 12

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Arg Pro Ile Thr Pro Val Leu Val Asp Ala Met Asp Tyr
            100                 105                 110

Trp Gln Gln Gly Thr Leu Val Thr Val Ser Ser
        115                 120

<210> SEQ ID NO 13
<211> LENGTH: 219
<212> TYPE: PRT
<213> ORGANISM: Artificial Sequence
<220> FEATURE:
<223> OTHER INFORMATION: Description of Artificial Sequence: Synthetic humanized antibody

<400> SEQUENCE: 13

Asp Val Val Met Thr Gln Ser Pro Leu Ser Leu Pro Val Thr Leu Gly
1               5                   10                  15

```
Gln Pro Ala Ser Ile Ser Cys Arg Ser Ser Gln Asn Ile Ile His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Gly Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Tyr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 14
<211> LENGTH: 453
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 14

Glu Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Val Arg Arg Pro Ile Thr Pro Val Leu Val Asp Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
            165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
    355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Gln Asn Asn Tyr Lys Thr Tyr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
            435                 440                 445
Leu Ser Pro Gly Lys
    450

<210> SEQ ID NO 15
<211> LENGTH: 132
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: SIGNAL
<222> LOCATION: (1)..(20)
<220> FEATURE:
<221> NAME/KEY: mat_peptide
<222> LOCATION: (21)..(132)

<400> SEQUENCE: 15

Met Arg Leu Pro Ala Gln Leu Leu Gly Leu Leu Met Leu Trp Val Ser
-20                 -15                 -10                 -5
Gly Ser Ser Gly Asp Val Val Met Thr Gln Ser Pro Leu Ser Leu Pro
```

```
              -1   1                 5                      10
Val Thr Pro Gly Glu Pro Ala Ser Ile Ser Cys Arg Ser Ser Gln Asn
            15                  20                  25

Ile Val His Ser Asn Gly Asn Thr Tyr Leu Glu Trp Tyr Leu Gln Lys
        30                  35                  40

Pro Gly Gln Ser Pro Gln Leu Leu Ile Tyr Lys Val Ser Asn Arg Phe
45                  50                  55                  60

Ser Gly Val Pro Asp Arg Phe Ser Gly Ser Gly Ser Gly Thr Asp Phe
                65                  70                  75

Thr Leu Lys Ile Ser Arg Val Glu Ala Glu Asp Val Gly Val Tyr Tyr
            80                  85                  90

Cys Phe Gln Gly Ser His Val Pro Leu Thr Phe Gly Gln Gly Thr Lys
                95                  100                 105

Leu Glu Ile Lys
        110

<210> SEQ ID NO 16
<211> LENGTH: 142
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: SIGNAL
<222> LOCATION: (1)..(19)
<220> FEATURE:
<221> NAME/KEY: mat_peptide
<222> LOCATION: (20)..(142)

<400> SEQUENCE: 16

Met Lys His Leu Trp Phe Phe Leu Leu Leu Val Ala Ala Pro Arg Trp
                -15                 -10                 -5

Val Leu Ser Gln Val Gln Leu Gln Glu Ser Gly Pro Gly Leu Val Lys
        -1   1                 5                      10

Pro Ser Glu Thr Leu Ser Leu Thr Cys Thr Phe Ser Gly Phe Ser Leu
            15                  20                  25

Ser Thr Asn Gly Met Gly Val Ser Trp Ile Arg Gln Pro Pro Gly Lys
30                  35                  40                  45

Gly Leu Glu Trp Leu Ala His Ile Tyr Trp Asp Glu Asp Lys Arg Tyr
                50                  55                  60

Asn Pro Ser Leu Lys Ser Arg Leu Thr Ile Ser Lys Asp Thr Ser Lys
            65                  70                  75

Asn Gln Val Ser Leu Lys Leu Ser Ser Val Thr Ala Ala Asp Thr Ala
            80                  85                  90

Val Tyr Tyr Cys Ala Arg Arg Ile Ile Tyr Asp Val Glu Asp Tyr
            95                  100                 105

Phe Asp Tyr Trp Gly Gln Gly Thr Thr Val Thr Val Ser Ser
110                 115                 120

<210> SEQ ID NO 17
<211> LENGTH: 131
<212> TYPE: PRT
<213> ORGANISM: Mus musculus
<220> FEATURE:
<221> NAME/KEY: SIGNAL
<222> LOCATION: (1)..(19)
<220> FEATURE:
<221> NAME/KEY: mat_peptide
<222> LOCATION: (20)..(131)
```

-continued

```
<400> SEQUENCE: 17

Met Lys Leu Pro Val Arg Leu Leu Val Leu Met Phe Trp Ile Pro Ala
            -15                 -10                 -5

Ser Ser Ser Asp Val Leu Met Thr Gln Thr Pro Leu Ser Leu Pro Val
        -1   1               5                  10

Ser Leu Gly Asp Gln Ala Ser Ile Ser Cys Arg Ser Ser Gln Asn Ile
         15                 20                  25

Val His Ser Asn Gly Asn Thr Tyr Leu Glu Trp Tyr Leu Gln Lys Pro
 30              35                  40                      45

Gly Gln Ser Pro Lys Leu Leu Ile Tyr Lys Val Ser Asn Arg Phe Ser
             50                  55                  60

Gly Val Pro Asp Arg Phe Ser Gly Ser Gly Ser Gly Thr Asp Phe Thr
             65                  70                  75

Leu Lys Ile Ser Arg Val Glu Ala Glu Asp Leu Gly Val Tyr Tyr Cys
         80                  85                  90

Phe Gln Gly Ser His Val Pro Leu Thr Phe Gly Ala Gly Thr Lys Leu
     95                 100                 105

Glu Leu Lys
110

<210> SEQ ID NO 18
<211> LENGTH: 142
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: SIGNAL
<222> LOCATION: (1)..(19)
<220> FEATURE:
<221> NAME/KEY: mat_peptide
<222> LOCATION: (20)..(142)

<400> SEQUENCE: 18

Met Lys His Leu Trp Phe Phe Leu Leu Leu Val Ala Ala Pro Arg Trp
            -15                 -10                 -5

Val Leu Ser Gln Leu Gln Leu Gln Glu Ser Gly Pro Gly Leu Val Lys
        -1   1               5                  10

Pro Ser Glu Thr Leu Ser Leu Thr Cys Thr Phe Ser Gly Phe Ser Leu
         15                 20                  25

Ser Thr Asn Gly Met Gly Val Ser Trp Ile Arg Gln Pro Pro Gly Lys
 30              35                  40                      45

Gly Leu Glu Trp Ile Gly His Ile Tyr Trp Asp Glu Asp Lys Arg Tyr
             50                  55                  60

Asn Pro Ser Leu Lys Ser Arg Val Thr Ile Ser Lys Asp Thr Ser Lys
             65                  70                  75

Asn Gln Phe Ser Leu Lys Leu Ser Ser Val Thr Ala Ala Asp Thr Ala
             80                  85                  90

Val Tyr Tyr Cys Ala Arg Arg Arg Ile Ile Tyr Asp Val Glu Asp Tyr
         95                 100                 105

Phe Asp Tyr Trp Gly Gln Gly Thr Thr Val Thr Val Ser Ser
110              115                 120

<210> SEQ ID NO 19
<211> LENGTH: 142
<212> TYPE: PRT
<213> ORGANISM: Artificial Sequence
<220> FEATURE:
```

```
<223> OTHER INFORMATION: Description of Artificial Sequence: Synthetic
      humanized antibody
<220> FEATURE:
<221> NAME/KEY: SIGNAL
<222> LOCATION: (1)..(19)
<220> FEATURE:
<221> NAME/KEY: mat_peptide
<222> LOCATION: (20)..(142)

<400> SEQUENCE: 19

Met Lys His Leu Trp Phe Phe Leu Leu Leu Val Ala Ala Pro Arg Trp
                -15                 -10                  -5

Val Leu Ser Gln Leu Gln Leu Gln Glu Ser Gly Pro Gly Leu Val Lys
         -1  1               5                   10

Pro Ser Glu Thr Leu Ser Leu Thr Cys Thr Phe Ser Gly Phe Ser Leu
     15              20                  25

Ser Thr Asn Gly Met Gly Val Ser Trp Ile Arg Gln Pro Pro Gly Lys
 30              35                  40                  45

Gly Leu Glu Trp Leu Gly His Ile Tyr Trp Asp Glu Asp Lys Arg Tyr
                 50                  55                  60

Asn Pro Ser Leu Lys Ser Arg Val Thr Ile Ser Lys Asp Thr Ser Lys
             65                  70                  75

Asn Gln Val Ser Leu Lys Leu Ser Ser Val Thr Ala Ala Asp Thr Ala
         80                  85                  90

Val Tyr Tyr Cys Ala Arg Arg Arg Ile Ile Tyr Asp Val Glu Asp Tyr
     95                 100                 105

Phe Asp Tyr Trp Gly Gln Gly Thr Thr Val Thr Val Ser Ser
110                 115                 120

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 20

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ser
                 85                  90                  95

Ser His Val Pro Leu Thr Phe Gly Gln Gly Thr Lys Leu Glu Ile Lys
            100                 105                 110

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody
```

```
<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 23

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
```

```
                  35                  40                  45
Trp Val Ala His Ile Trp Trp Asp Asp Lys Tyr Tyr Asn Pro Ser
 50                  55                  60

Leu Lys Ser Arg Phe Thr Ile Ser Lys Asp Asn Ser Lys Asn Thr Leu
 65                  70                  75                  80

Tyr Leu Gln Met Asn Ser Leu Arg Ala Glu Asp Thr Ala Val Tyr Tyr
                     85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 24

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
 50                  55                  60

Leu Lys Ser Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                     85                  90                  95

Cys Ala Arg Arg Thr Thr Thr Ala Asp Tyr Phe Ala Tyr Trp Gly Gln
                100                 105                 110

Gly Thr Thr Val Thr Val Ser Ser
            115                 120

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 25

Gln Val Gln Leu Val Glu Ser Gly Gly Gly Val Val Gln Pro Gly Arg
 1               5                  10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
 50                  55                  60

Leu Lys Ser Arg Phe Thr Ile Ser Lys Asp Asn Ser Lys Asn Thr Leu
 65                  70                  75                  80

Tyr Leu Gln Met Asn Ser Leu Arg Ala Glu Asp Thr Ala Val Tyr Tyr
```

85                  90                  95
Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 28
<211> LENGTH: 120
<212> TYPE: PRT
<213> ORGANISM: Artificial Sequence
<220> FEATURE:
<223> OTHER INFORMATION: Description of Artificial Sequence: Synthetic humanized antibody

<400> SEQUENCE: 28

```
Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120
```

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Synthetic humanized antibody

<400> SEQUENCE: 29

```
Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120
```

<210> SEQ ID NO 30
<211> LENGTH: 120
<212> TYPE: PRT
<213> ORGANISM: Artificial Sequence
<220> FEATURE:
<223> OTHER INFORMATION: Description of Artificial Sequence: Synthetic humanized antibody

<400> SEQUENCE: 30

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 31
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 31

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 32
<211> LENGTH: 121
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
     50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
             100                 105                 110

Gly Thr Thr Val Thr Val Ser Ser Val
             115                 120

<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
     50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
             100                 105                 110

Gly Thr Thr Val Thr Val Ser Ser Val
             115                 120

<210> SEQ ID NO 34
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
     50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                 85                  90                  95

```
Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 35

Gln Val Gln Leu Val Glu Ser Gly Gly Val Val Gln Pro Gly Arg
1               5                   10                  15

Ser Leu Arg Leu Ser Cys Ala Phe Ser Gly Phe Ser Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 36
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 36

Gln Val Gln Leu Val Glu Ser Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 37
```

```
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Val Ala His Ile Trp Trp Asp Asp Lys Tyr Tyr Asn Pro Ser
        50                  55                  60

Leu Lys Ser Arg Leu Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 38

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
                20                  25                  30

Gly Met Ser Val Gly Trp Ile Arg Gln Ala Pro Gly Lys Gly Leu Glu
            35                  40                  45

Trp Leu Ala His Ile Trp Trp Asp Asp Lys Tyr Tyr Asn Pro Ser
        50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
            115                 120

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 39
```

```
Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45

Trp Val Ala His Ile Trp Trp Asp Asp Lys Tyr Tyr Asn Pro Ser
    50                  55                  60

Leu Lys Ser Arg Phe Thr Ile Ser Lys Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 40

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Thr Leu Ser Thr Ser
            20                  25                  30

Gly Met Ser Val Gly Trp Val Arg Gln Ala Pro Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 41

Gln Val Gln Leu Val Glu Ser Gly Gly Gly Val Val Gln Pro Gly Arg
1               5                   10                  15

Ser Leu Arg Leu Ser Cys Ala Phe Ser Gly Phe Ser Leu Ser Thr Ser
            20                  25                  30

Gly Met Ser Val Gly Trp Ile Arg Gln Ala Pro Gly Lys Gly Leu Glu
        35                  40                  45
```

```
Trp Leu Ala His Ile Trp Trp Asp Asp Lys Tyr Tyr Asn Pro Ser
 50                  55                  60

Leu Lys Ser Arg Leu Thr Ile Ser Lys Asp Asn Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Ala Arg Arg Thr Thr Thr Ala Asp Tyr Phe Ala Tyr Trp Gly Gln
            100                 105                 110

Gly Thr Thr Val Thr Val Ser Ser
        115                 120

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (2)
<223> OTHER INFORMATION: Val or Ile
<220> FEATURE:
<221> NAME/KEY: MOD_RES
<222> LOCATION: (7)
<223> OTHER INFORMATION: Ser or Thr
<220> FEATURE:
<221> NAME/KEY: MOD_RES
<222> LOCATION: (14)
<223> OTHER INFORMATION: Thr or Ser
<220> FEATURE:
<221> NAME/KEY: MOD_RES
<222> LOCATION: (15)
<223> OTHER INFORMATION: Leu or Pro
<220> FEATURE:
<221> NAME/KEY: MOD_RES
<222> LOCATION: (30)
<223> OTHER INFORMATION: Ile or Val
<220> FEATURE:
<221> NAME/KEY: MOD_RES
<222> LOCATION: (50)
<223> OTHER INFORMATION: Arg, Gln, or Lys
<220> FEATURE:
<221> NAME/KEY: MOD_RES
<222> LOCATION: (88)
<223> OTHER INFORMATION: Val or Leu
<220> FEATURE:
<221> NAME/KEY: MOD_RES
<222> LOCATION: (105)
<223> OTHER INFORMATION: Gln or Gly
<220> FEATURE:
<221> NAME/KEY: MOD_RES
<222> LOCATION: (108)
<223> OTHER INFORMATION: Lys or Arg
<220> FEATURE:
<221> NAME/KEY: MOD_RES
<222> LOCATION: (109)
<223> OTHER INFORMATION: Val or Leu

<400> SEQUENCE: 42

Asp Xaa Val Met Thr Gln Xaa Pro Leu Ser Leu Pro Val Xaa Xaa Gly
 1               5                  10                  15

Gln Pro Ala Ser Ile Ser Cys Arg Ser Ser Gln Ser Leu Xaa Tyr Ser
                 20                  25                  30

Asp Gly Asn Ala Tyr Leu His Trp Phe Leu Gln Lys Pro Gly Gln Ser
             35                  40                  45

Pro Xaa Leu Leu Ile Tyr Lys Val Ser Asn Arg Phe Ser Gly Val Pro
     50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Xaa Gly Val Tyr Tyr Cys Ser Gln Ser
                 85                  90                  95

Thr His Val Pro Trp Thr Phe Gly Xaa Gly Thr Xaa Xaa Glu Ile Lys
            100                 105                 110

Arg

<210> SEQ ID NO 43
<211> LENGTH: 112
<212> TYPE: PRT
<213> ORGANISM: Artificial Sequence
<220> FEATURE:
<223> OTHER INFORMATION: Description of Artificial Sequence: Synthetic
      humanized antibody
<220> FEATURE:
<221> NAME/KEY: MOD_RES
<222> LOCATION: (1)
<223> OTHER INFORMATION: Glu or Gln
<220> FEATURE:
<221> NAME/KEY: MOD_RES
<222> LOCATION: (7)
<223> OTHER INFORMATION: Ser or Leu
<220> FEATURE:
<221> NAME/KEY: MOD_RES
<222> LOCATION: (46)
<223> OTHER INFORMATION: Glu, Val, Asp, or Ser
<220> FEATURE:
<221> NAME/KEY: MOD_RES
<222> LOCATION: (63)
<223> OTHER INFORMATION: Thr or Ser
<220> FEATURE:
<221> NAME/KEY: MOD_RES
<222> LOCATION: (75)
<223> OTHER INFORMATION: Ala, Ser, Val, or Thr
<220> FEATURE:
<221> NAME/KEY: MOD_RES
<222> LOCATION: (76)
<223> OTHER INFORMATION: Lys or Arg
<220> FEATURE:
<221> NAME/KEY: MOD_RES
<222> LOCATION: (89)
<223> OTHER INFORMATION: Glu or Asp
<220> FEATURE:
<221> NAME/KEY: MOD_RES
<222> LOCATION: (107)
<223> OTHER INFORMATION: Leu or Thr

<400> SEQUENCE: 43

Xaa Val Gln Leu Val Glu Xaa Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Xaa Leu Val
        35                  40                  45

Ala Gln Ile Asn Ser Val Gly Asn Ser Thr Tyr Tyr Pro Asp Xaa Val
     50                  55                  60

Lys Gly Arg Phe Thr Ile Ser Arg Asp Asn Xaa Xaa Asn Thr Leu Tyr
 65                  70                  75                  80

Leu Gln Met Asn Ser Leu Arg Ala Xaa Asp Thr Ala Val Tyr Tyr Cys
                 85                  90                  95

Ala Ser Gly Asp Tyr Trp Gly Gln Gly Thr Xaa Val Thr Val Ser Ser
            100                 105                 110

<210> SEQ ID NO 44
<211> LENGTH: 113
<212> TYPE: PRT
```

```
<213> ORGANISM: Artificial Sequence
<220> FEATURE:
<223> OTHER INFORMATION: Description of Artificial Sequence: Synthetic
      humanized antibody

<400> SEQUENCE: 44

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Thr Tyr Cys Ser Gln Ser
                85                  90                  95

Thr His Val Pro Trp Thr Phe Gly Gln Gly Thr Lys Val Glu Ile Lys
            100                 105                 110

Arg

<210> SEQ ID NO 45
<211> LENGTH: 112
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Leu Val Thr Val Ser Ser
            100                 105                 110

<210> SEQ ID NO 46
<211> LENGTH: 219
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 46

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30
```

```
Asp Gly Asn Ala Tyr Leu His Trp Phe Leu Gln Lys Pro Gly Gln Ser
        35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 47
<211> LENGTH: 442
<212> TYPE: PRT
<213> ORGANISM: Artificial Sequence
<220> FEATURE:
<223> OTHER INFORMATION: Description of Artificial Sequence: Synthetic
      humanized antibody

<400> SEQUENCE: 47

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Ser Met Ser Trp Val Arg Gln Ala Pro Gly Lys Gly Leu Glu Leu Val
        35                  40                  45

Ala Gln Ile Asn Ser Val Gly Asn Ser Thr Tyr Tyr Pro Asp Thr Val
    50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175
```

```
Leu Ser Ser Val Val Thr Val Pro Ser Ser Leu Gly Thr Gln Thr
            180             185             190
Tyr Ile Cys Asn Val Asn His Lys Pro Ser Asn Thr Lys Val Asp Lys
        195             200             205
Lys Val Glu Pro Lys Ser Cys Asp Lys Thr His Thr Cys Pro Pro Cys
        210             215             220
Pro Ala Pro Glu Leu Leu Gly Gly Pro Ser Val Phe Leu Phe Pro Pro
225             230             235             240
Lys Pro Lys Asp Thr Leu Met Ile Ser Arg Thr Pro Glu Val Thr Cys
            245             250             255
Val Val Val Asp Val Ser His Glu Asp Pro Glu Val Lys Phe Asn Trp
            260             265             270
Tyr Val Asp Gly Val Glu Val His Asn Ala Lys Thr Lys Pro Arg Glu
            275             280             285
Glu Gln Tyr Asn Ser Thr Tyr Arg Val Val Ser Val Leu Thr Val Leu
        290             295             300
His Gln Asp Trp Leu Asn Gly Lys Glu Tyr Lys Cys Lys Val Ser Asn
305             310             315             320
Lys Ala Leu Pro Ala Pro Ile Glu Lys Thr Ile Ser Lys Ala Lys Gly
            325             330             335
Gln Pro Arg Glu Pro Gln Val Tyr Thr Leu Pro Pro Ser Arg Asp Glu
            340             345             350
Leu Thr Lys Asn Gln Val Ser Leu Thr Cys Leu Val Lys Gly Phe Tyr
            355             360             365
Pro Ser Asp Ile Ala Val Glu Trp Glu Ser Asn Gly Gln Pro Glu Asn
370             375             380
Asn Tyr Lys Thr Thr Pro Pro Val Leu Asp Ser Asp Gly Ser Phe Phe
385             390             395             400
Leu Tyr Ser Lys Leu Thr Val Asp Lys Ser Arg Trp Gln Gln Gly Asn
            405             410             415
Val Phe Ser Cys Ser Val Met His Glu Ala Leu His Asn His Tyr Thr
            420             425             430
Gln Lys Ser Leu Ser Leu Ser Pro Gly Lys
            435             440
```